US008884051B2

(12) United States Patent
Malofsky et al.

(10) Patent No.: US 8,884,051 B2
(45) Date of Patent: Nov. 11, 2014

(54) SYNTHESIS OF METHYLENE MALONATES USING RAPID RECOVERY IN THE PRESENCE OF A HEAT TRANSFER AGENT

(75) Inventors: Bernard M. Malofsky, Bloomfield, CT (US); Adam G. Malofsky, Loveland, OH (US); Tanmoy Dey, Stamford, CT (US); Jeffrey M. Sullivan, Goshen, OH (US); Yangbin Chen, Lima, NY (US); Stanley C. Wojciak, New Britain, CT (US); Michael C. Cockrem, Madison, WI (US)

(73) Assignee: Bioformix Inc., Loveland, OH (US)

( * ) Notice: Subject to any disclaimer, the term of this patent is extended or adjusted under 35 U.S.C. 154(b) by 0 days.

(21) Appl. No.: 13/880,471

(22) PCT Filed: Oct. 19, 2011

(86) PCT No.: PCT/US2011/056926
§ 371 (c)(1),
(2), (4) Date: Jul. 8, 2013

(87) PCT Pub. No.: WO2012/054633
PCT Pub. Date: Apr. 26, 2012

(65) Prior Publication Data
US 2013/0281580 A1 Oct. 24, 2013

Related U.S. Application Data

(60) Provisional application No. 61/523,705, filed on Aug. 15, 2011, provisional application No. 61/523,311, filed on Aug. 13, 2011, provisional application No. 61/405,056, filed on Oct. 20, 2010, provisional application No. 61/405,033, filed on Oct. 20, 2010, provisional application No. 61/405,078, filed on Oct. 20, 2010, provisional application No. 61/405,049, filed on Oct. 20, 2010, provisional application No. 61/405,029, filed on Oct. 20, 2010.

(51) Int. Cl.
*C07C 67/343* (2006.01)
*C08F 136/20* (2006.01)
*C08G 63/00* (2006.01)
*C08L 47/00* (2006.01)
*C07C 69/602* (2006.01)
*C08L 35/02* (2006.01)
*C08F 122/14* (2006.01)

(52) U.S. Cl.
CPC ............ *C07C 69/602* (2013.01); *C08F 136/20* (2013.01); *C07C 67/343* (2013.01); *C08G 63/00* (2013.01); *C08L 47/00* (2013.01); *C08L 35/02* (2013.01); *C08F 122/14* (2013.01)
USPC ....................................................... 560/212

(58) Field of Classification Search
CPC .................................................. C07C 67/327
See application file for complete search history.

(56) References Cited

U.S. PATENT DOCUMENTS

| 2,313,501 | A | | 3/1943 | Bryant |
| 2,330,033 | A | * | 9/1943 | D Alelio .................. 560/203 |
| 3,197,318 | A | * | 7/1965 | Halpern et al. ............ 106/205.2 |
| 3,221,745 | A | | 12/1965 | Coover, Jr. |
| 3,523,097 | A | | 8/1970 | Coover, Jr. |
| 3,557,185 | A | | 1/1971 | Ito |
| 3,758,550 | A | | 9/1973 | Eck et al. |
| 3,975,422 | A | | 8/1976 | Buck |
| 4,049,698 | A | | 9/1977 | Hawkins et al. |
| 4,056,543 | A | | 11/1977 | Ponticello |
| 4,083,751 | A | * | 4/1978 | Choi et al. ...................... 202/99 |
| 4,160,864 | A | | 7/1979 | Ponticello et al. |
| 4,931,584 | A | | 6/1990 | Bru-Magniez et al. |
| 5,142,098 | A | | 8/1992 | Bru-Magniez et al. |
| 5,550,172 | A | | 8/1996 | Regula et al. |
| 6,106,807 | A | | 8/2000 | Albayrak et al. |
| 6,211,273 | B1 | | 4/2001 | Bru-Magniez et al. |
| 6,245,933 | B1 | | 6/2001 | Malofsky et al. |

(Continued)

FOREIGN PATENT DOCUMENTS

WO    WO 2012/054616    4/2012

OTHER PUBLICATIONS

Takagi et al, Kogyo Kagaku Zasshi, Reaction of Active Methylene Radicals with Formaldehyde. I. Synthesis of Diethyl Methylenemalonate, 1953, 56, pp. 901-903, English abstract.*
McNab, Kirk-Othmer Encyclopedia of Chemical Technology, Pyrolysis, Flash Vacuum, 2009, John Wiley & Sons, Inc., pp. 1-26.*
M. Ware et al.: "DBU: An Efficient Catalyst for Knoeveganel Condensation under Solvent-free Condition," Bulletin of the Catalysis Society of India, (2007), vol. 6, pp. 104-106.
V. G. Nenajdenko et al.: "Reaction of 2-Methylene-1,3-Dicarbonyl Compounds Containing a CF3-Group with 1,3-Dienes," Tetrahedron, (2000), vol. 56, pp. 6549-6556.

(Continued)

*Primary Examiner* — Paul A Zucker
(74) *Attorney, Agent, or Firm* — Edwards Wildman Palmer LLP; Barry Kramer; Nicholas J. DiCeglie, Jr.

(57) ABSTRACT

The present invention provides a method of making a methylene malonate monomer that includes the steps of reacting a malonic acid ester with a source of formaldehyde optionally in the presence of an acidic or basic catalyst and optionally in the presence of an acidic or non-acidic solvent to form reaction complex. The reaction is optionally performed in the presence of or contacted with an energy transfer means such as a heat transfer agent, a heat transfer surface, a source of radiation or a laser such that reaction complex is substantially vaporized to produce a vapor phase comprising methylene malonate monomer which may be isolated. The present invention further provides methylene malonate monomers prepared by the method of the invention, as well as compositions and products formed from the methylene malonate monomers, including monomer-based products (e.g., inks, adhesives, coatings, sealants or reactive molding) and polymer-based products (e.g., fibers, films, sheets, medical polymers, composite polymers and surfactants).

18 Claims, 36 Drawing Sheets

(56) References Cited

U.S. PATENT DOCUMENTS

| | | |
|---|---|---|
| 6,420,468 B2 | 7/2002 | Bru-Magniez et al. |
| 6,440,461 B1 | 8/2002 | Bru-Magniez et al. |
| 6,512,023 B1 | 1/2003 | Malofsky et al. |
| 6,610,078 B1 | 8/2003 | Bru-Magniez et al. |
| 6,699,928 B2 | 3/2004 | Cobbley et al. |
| 6,750,298 B1 | 6/2004 | Breton et al. |
| 2004/0076601 A1 | 4/2004 | Bru-Magniez et al. |
| 2008/0227919 A9 | 9/2008 | Li et al. |

OTHER PUBLICATIONS

J. S. Yadav et al.,: "Phosphane-Catalyzed Knoevenagel Condensation: a Facile Synthesis of α-Cyanoacrylates and α-Cyanoacrylonitriles," Eur. J. Org. Chem. (2004), pp. 546-551.

B. C. Ranu et al.: "Ionic Liquid as Catalyst and Reaction Medium—a Simple, Efficient and Green Procedure for Knoevenagel Condensation of Aliphatic and Aromatic Carbonyl Compounds Using a Task-Specific Basic Ionic Liquid," Euro. J. Org. Chem., (2006), pp. 3767-3770.

H. A. Oskooie et al.: "On Water: an Efficient Knoevenagel Condensation using 12-Tungstophosphoric Acid as a Reusable Green Catalyst," Synthetic Communications, (2006), vol. 36, pp. 2819-2823.

H. Jiang et al.: "Inorganic Zinc Salts Catalyzed Knoevenagel Condensation at Room Temperature without Solvent," Preparative Biochemistry & Biotechnology, (2009), vol. 39, pp. 194-200.

B. M. Reddy et al.: "An Easy-to-use Heterogeneous Promoted Zirconia Catalyst for Knoevenagel Condensation in liquid Phase under Solvent-Free Conditions," Journal of Molecular Catalysis A: Chemical, (2006), vol. 258, pp. 302-307.

D. H. Jung et al.: "New and General Methods for the Synthesis of Arylmethylene Bis(3-Hydroxy-2-Cyclohexene-1-Ones) and Xanthenediones by EDDA and in(OTf)3-Catalyzed One-Pot Domino Knoevenagel/Michael or Koevenagel/Michael/Cyclodehydration Reactions," Bull. Korean Chem. Soc. (2009) vol. 30, No. 9, pp. 1989-1995.

P. Klemarczyk: "Adhesion Studies of Mixtures of Ethyl Cyanoacrylate with a Difunctional Cyanoacrylate Monomer and with other Electron-deficient Olefins," J. Adhesion, (1999), vol. 69, pp. 293-306.

P. Klemarczyk: "A General Synthesis of 1,1 Disubstituted Electron Deficient Olefins and their Polymer Properties," Polymer, (1998), vol. 39, No. 1, pp. 173-181.

P. Ballesteros et al.: "DI-tert-Butyl Methylenemalonate [Propanedioic Acid, Methylene-, bis(1,1-dimethylethyl)ester]," Organic Syntheses. Coll. (1990), vol. 7, p. 142 ; (1986) vol. 64, p. 63.

A. M. Vetrova et al.: "Improvement of the Thermal Stability of Cyanoacrylate Adhesives," Polymer Science, Series D, (2009), vol. 2, No. 1, pp. 27-30.

A. C. Cope: "Condensation Reactions. I. The Condensation of Ketones with Cyanoacetic Esters and the Mechanism of the Knoevenagel Reaction," Condensation of Ketones with Cyanoacetic Esters, (1937), vol. 59, pp. 2327-2330.

G. Lai et al.: "Ionic Liquid Functionalized Silica Gel: Novel Catalyst and Fixed Solvent," Tetrahedron Letters (2006), vol. 47, pp. 6951-6953.

J. R. Harjani et al.: "Lewis Acidic Ionic Liquids for the Synthesis of Electrophilic Alkenes via the Knoevenagel Condensation," Tetrahedron Letters, (2002), vol. 43, pp. 1127-1130.

P. Ballesteros et al.: "Synthesis of DI-tert-Butyl Methylenemalonate, a Sterically Hindered 1,1-Dicarbonyl Alkene," J. Org. Chem, (1983), vol. 48, pp. 3603-3605.

T. Doi et al.: "Synthesis of Dimethyl gloiosiphne A by Way of Palladium-Catalyzed Domino Cyclization," J. Org. Chem., (2007), vol. 72, pp. 3667-3671.

\* cited by examiner

SSH Process
Catalyst: Zn(OAc)$_2$, 2H$_2$O
Paraform: 1.5 moles

SYNTHESIS OF METHYLENE MALONATES USING RAPID RECOVERY IN THE PRESENCE OF A HEAT TRANSFER AGENT

CROSS REFERENCE TO RELATED APPLICATIONS

This application is a U.S. National Stage application under 35 U.S.C. §371 of International Patent Application Serial No. PCT/US2011/056926, filed Oct. 19, 2011, which Application claims the benefit of priority of U.S. Provisional Patent Application No. 61/405,029, filed Oct. 20, 2010, U.S. Provisional Patent Application No. 61/405,049, filed Oct. 20, 2010, U.S. Provisional Patent Application No. 61/405,078, filed Oct. 20, 2010, U.S. Provisional Patent Application No. 61/405,033, filed Oct. 20, 2010, U.S. Provisional Patent Application No. 61/405,056, filed Oct. 20, 2010, U.S. Provisional Patent Application No. 61/523,311, filed Aug. 13, 2011, and U.S. Provisional Patent Application No. 61/523,705, filed Aug. 15, 2011, the disclosures of each of which are expressly incorporated by reference in their entireties.

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

BACKGROUND OF THE INVENTION

1. Field of the Invention

The invention relates to improved methods for producing methylene malonate monomers and to the use or application of methylene malonate monomers prepared by the methods of the invention as commercial products and compositions, including, for example, monomer-based products (e.g., inks, adhesives, coatings, sealants or reactive molding) and polymer-based products (e.g., fibers, films, sheets, medical polymers, composite polymers and surfactants).

2. Background

Methylene malonates are compounds having the general formula (I):

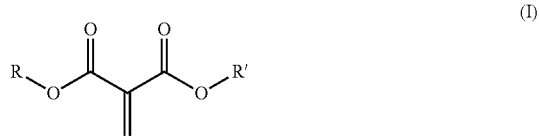

(I)

wherein R and R' may be the same or different and may represent nearly any substituent or side-chain. Such compounds have been known since 1886 where the formation of diethyl methylene malonate was first demonstrated by W. H. Perkin, Jr. (Perkin, Ber. 19, 1053 (1886)).

These compounds have the potential to form the basis of a highly valuable novel large-scale platform for the chemical synthesis of a new order of raw materials for the generation of a wide variety of new chemical products, including inks, adhesives, coatings, sealants, molding, fibers, films, sheets, medical polymers, composites, surfactants and the like. While the potential is there for such materials, methylene malonates or materials made therefrom have found very limited commercial success owing to the difficulty of their production, including poor and erratic yields, lack of reactivity, and general instability of the monomer products. These difficulties stem from the deficiencies in the methods developed over the years which have proposed various schemes for synthesizing methylene malonates.

However, while such earlier methods for producing methylene malonates have been known for many years, these prior methods suffer significant deficiencies which preclude their use in obtaining commercially viable monomers. Such deficiencies include unwanted polymerization of the monomers during synthesis (e.g., formation of polymers or oligomers or alternative complexes), formation of undesirable side products (e.g., ketals or other latent acid-forming species which impede rapid polymerization), degradation of the product, insufficient and/or low yields, and ineffective and/or poorly functioning monomer product (e.g., poor adhesive characteristics, stability, or other functional characteristics), among other problems. The overall poorer yield, quality, and chemical performance of the monomer products formed by prior methods has impinged on their practical use in the production of the above commercial and industrial products. No viable solutions to solve the aforementioned problems have yet been proposed, accepted and/or recognized and certainly do not exist currently in the industry.

For example, in U.S. Pat. No. 2,330,033 to Gaetano D'Alelio ("the '033 patent"), methylene malonic esters are prepared by condensing a malonic ester with formaldehyde under alkaline conditions, acidifying with acetic acid and dehydrating the mass and distilling the methylene malonic ester. In each example of the '033 patent, the condensation reaction is acidified using acetic acid. Furthermore, the ester is described as polymerizing spontaneously in the absence of inhibitors. Thus, the reaction conditions described in the '033 patent would have led to the undesirable premature polymerization of the monomer and the production of deleterious side products. Further, the reference does not even recognize the formation of such deleterious side products, let alone does it provide any teachings or suggestions as to how to avoid or eliminate the formation of these impurities. Accordingly, the methylene malonates purportedly formed by this process are impractical for use in the production of viable commercial and industrial products.

Similarly, in U.S. Pat. No. 2,313,501 to Bachman et al. ("the '501 patent"), methylene dialkyl malonates are prepared by the reaction of dialkyl malonates with formaldehyde in the presence of an alkali metal salt of a carboxylic acid in a substantially anhydrous carboxylic acid solvent. The method of the '501 patent purports to provide higher yields than the prior methods of condensing formaldehyde with a dialkyl malonate in the presence of a base. In the '501 patent, methylene diethyl malonate is distilled directly from the reaction mixture under sub-atmospheric pressure. The ester is described as forming a soft waxy white polymer upon standing, indicating the presence of a high degree of deleterious side products. The '501 patent does not even recognize the formation of such deleterious side products, let alone does it provide any teachings or suggestions as to how to avoid or eliminate the formation of such impurities. Thus, the methylene malonates purportedly formed by this process are highly unstable and are impractical for use in the production of viable commercial and industrial products.

Furthermore, in U.S. Pat. No. 3,197,318 to Halpern et al. ("the '318 patent"), dialkyl methylene malonic acid esters are prepared by condensing dimethylmalonate with formaldehyde in the presence of acetic acid and an acetate of a heavy metal at 100-110° C. The reaction mixture is directly distilled under reduced pressure. The '318 patent states that in the anhydrous composition, the reaction either fails to occur or is greatly delayed by the inhibitor up to the time when the effectiveness of the inhibitor is reduced by contact of moisture therewith (from occluded surface water on glass, metal or the like). The unfavorable reaction conditions described in this reference would have led to the production of deleterious side products. The '318 patent does not even recognize the formation or presence of these impurities, let alone offer teachings or suggestions as to how to avoid or eliminate their formation. Accordingly, the methylene malonates purportedly formed by the process of the '318 patent would have been impractical for their use in the production of viable commercial products.

Also, in U.S. Pat. No. 3,221,745 to Coover et al. ("the '745 patent"), monomeric dialkyl esters of methylene malonic acid are purportedly prepared in high purity because even with small amounts of impurities that influence polymerization the adhesive utility will be impaired. The '745 patent describes removing all impurities to levels below 100 parts-per-million preferably below 10 parts-per-million. The monomers are prepared by hydrogenating the olefinic bond of a dialkyl alkoxy-methylenemalonate in the presence of a hydrogenation catalyst and pyrolyzing the reaction product. The '745 patent states that these high purity materials polymerize and form firm bonds in situ rapidly, within seconds. Indeed, the '745 patent, like related U.S. Pat. No. 3,523,097 to Coover et al. ("the '097 patent"), requires the use of an acidic stabilizer to enhance shelf-life and to prevent premature polymerization. However, the high temperature conditions of the pyrolysis reaction invariably results in the formation of unwanted and deleterious side products and is a much more expensive and difficult synthesis process for preparing methylene malonate as compared to the Knovenagel reaction with formaldehyde. Thus, the monomer purportedly formed by the processes of the '745 and '097 patents is impractical for use in the production of viable commercial and industrial products.

Still further, in U.S. Pat. No. 3,758,550 to Eck et al. ("the 550 patent") report on a general process for producing methylene malonic esters of the general formula $CH_2$=C($CO_2R$)$_2$, by reacting paraformaldehyde in glacial acetic acid in the presence of a catalyst to form a product in the form of a "gel" which is then "cracked" at high temperature distillation. The reaction is conducted over long periods of time, including up to 15 hours, and produces a substantial amount of deleterious side products, as evidenced by the gelatinous characteristics of the product. Further, the '550 patent contains no support showing the functionality of the monomers produced. Due to the likely presence of high levels of impurities, the functionality of the monomers produced by the '550 patent would likely be substantially compromised.

Citing numerous disadvantages of the foregoing processes, which disadvantages were said to make them difficult, if not impossible, to provide commercially viable monomers, Bru-Magniez. et. al. (U.S. Pat. No. 4,932,584 and U.S. Pat. No. 5,142,098) ("the '584 and '098 patents") developed a process whereby anthracene adducts were prepared by reacting mono- or di-malonic acid ester with formaldehyde in the presence of anthracene, most preferably in a non-aqueous solvent medium in the presence of select catalysts. According to these patents, the anthracene adducts were said to be readily produced in high yields with the desired methylene malonates obtained by stripping them from the anthracene adduct by any of the known methods including heat treatment, thermolysis, pyrolysis or hydrolysis; preferably heat treatment in the presence of maleic anhydride. The resultant crude products were then subjected to multiple distillations, preferably lower temperature distillations under vacuum, to recover the purified methylene malonates. Despite the claim to high yields, their crude yields were generally in the range of 21-71%, and more importantly, nothing is taught with respect to the purity of the material obtained.

While the use of intermediate adducts promoted higher yields and allowed greater versatility, particularly with respect to the broader variety of methylene malonates capable of being produced, lingering problems persisted, namely batch-to-batch inconsistency and the general instability of the process as well as the so-formed crude and final products, especially in bulk storage, and of formulated products, such as adhesives, made with the same. Additionally, the adduct routes involve considerable added expense, particularly in light of the need for the additional reactants and other materials, added production steps and time, new energy requirements and environmental concerns, and the like. Furthermore, despite their advances, these processes have yet to fully or even adequately address, particularly from a commercial viability standpoint, the underlying and critical problems evidenced by the continuing inconsistency in the production of the methylidene malonates, particularly as reflected by the ongoing instability of the reaction mix particularly during the distillation and recovery of the desired product as well as of the recovered product. It is this erratic nature of the production process and resultant product and the attendant costs associated therewith that compromises and overshadows the commercial value and opportunity for these products.

Similar conclusions may be drawn from other representative prior references that purport to teach the synthesis of methylene malonates, including, for example, U.S. Pat. Nos. 3,557,185; 3,975,422; 4,049,698; 4,056,543; 4,160,864; and 6,106,807. None of these references, however, recognize the same problems discussed above, including the formation of deleterious side products, such as, ketals and other latent acid-forming species which impede monomer performance, the occurrence of unwanted polymerization (e.g., unintended formation of polymers, oligomers or alternative complexes) and the general degradation and instability of the monomer products which together substantially impedes the production of high-quality methylene malonate monomers having commercial viability.

In view of the above art, there remains no known single viable commercially suitable method or process for the chemical synthesis of methylene malonate monomers which may be utilized to produce these important raw materials for the generation of a wide variety of commercial and industrial products. Thus, a need exists for improved methods for synthesizing methylene malonate monomers that are capable of being viably used in commercial and industrial applications.

The present invention solves the aforementioned problems in the synthesis of methylene malonate monomers and paves the way to a commercially viable source of an important raw material.

SUMMARY OF THE INVENTION

The purpose and advantages of the present invention will be set forth in and apparent from the description that follows. Additional advantages of the invention will be realized and attained by the methods and systems particularly pointed out in the written description and claims hereof, as well as from the appended drawings.

In a first aspect, the invention provides a method of making a methylene malonate monomer comprising:
  (a) reacting a malonic acid ester with a source of formaldehyde; optionally in the presence of an acidic or basic catalyst; and optionally in the presence of an acidic or non-acidic solvent, to form a reaction complex; and (b) contacting the reaction complex or a portion thereof with an energy transfer means to produce a vapor phase comprising methylene malonate monomer; and (c) isolating the methylene malonate monomer from the vapor phase.

In one embodiment, the first aspect of the invention further comprises the step of repeating steps (b) and (c) on additional portions of the reaction complex.

In certain embodiments of the first aspect of the invention, the reaction complex, or a portion thereof, is substantially vaporized in less than 15 minutes; less than 10 minutes; less than 1 minute; less than 30 seconds; less than 10 seconds; or less than 1 second.

In other embodiments of the first aspect of the invention, the reaction complex, or a portion thereof, is substantially vaporized prior to the formation of latent acid forming impurities or irreversible complex impurities.

In another embodiments of the first aspect of the invention wherein step (b) is performed on discrete portions of the reaction complex, each portion of reaction complex is substantially vaporized in step (b) prior to the contacting of another portion of reaction complex with the energy transfer means. In other embodiments of the second aspect of the invention, the reaction complex is vaporized continuously upon formation in step (a).

In certain embodiments of the first aspect of the invention, the energy transfer means is a heat transfer agent.

In other embodiments of the first aspect of the invention, the energy transfer means is a heat exchanger. In particular embodiments the heat exchanger is a shell and tube heat exchanger, a plate heat exchanger, an adiabatic wheel heat exchanger, a finned pipe heat exchanger, a plate fin heat exchanger, or a scraped surface heat exchanger.

In still other embodiments of the first aspect of the invention, the energy transfer means is a laser.

In yet other embodiments of the second aspect of the invention, the energy transfer means is a source of radiation. In particular embodiments, the radiation is microwave radiation.

In a second aspect, the invention provides a method of making a methylene malonate monomer comprising:

(a) reacting a malonic acid ester with a source of formaldehyde in the presence of heat transfer agent; optionally in the presence of an acidic or basic catalyst; and optionally in the presence of an acidic or non-acidic solvent, to form a reaction complex; and (b) producing a vapor phase comprising methylene malonate monomer from the reaction complex by heating the reaction complex to between about 150° C. and about 300° C.; and (c) isolating the methylene malonate monomer from the vapor phase.

In one embodiment of the second aspect of the invention, the step of producing a vapor phase (b) is performed by heating the reaction complex from about 130° C. to between about 150° C. and about 300° C. in less than 15 minutes. In certain other embodiments of the first aspect of the invention, the step of producing a vapor phase (b) is performed by heating the reaction complex from about 130° C. to between about 150° C. and about 300° C. in less than 10 minutes.

In certain embodiments of the first and second aspects of the invention utilizing a heat transfer agent, the heat transfer agent is a heated inert gas, one or more metal beads, one or more glass beads, one or more porcelain beads, sand, silica, silicone oil, mineral oil, a petroleum based heat transfer oil, a synthetic chemical based heat transfer oil, or a pre-formed portion of reaction complex.

In certain embodiments of the invention the reacting step (a) is performed at about 60° C. to about 130° C.

In other embodiments of the invention, the isolation of methylene malononate monomer from the vapor phase, step (c), is achieved by fractional distillation after condensation of the vapor phase. In still other embodiments, the isolation of methylene malononate monomer from the vapor phase, step (c), is achieved by gas chromatography. In yet other embodiments, the isolation of methylene malononate monomer from the vapor phase, step (c), is achieved by liquid chromatography after condensation of the vapor phase.

In certain embodiments of the invention, the method further comprises the step of (d) redistilling the methylene malonate monomer under reduced pressure within about 60 minutes of recovery, within about 30 minutes of recovery, within about 10 minutes, of recovery or immediately after recovery.

In another embodiment, the reacting step (a) of the methods of the invention is performed in the absence of a catalyst.

In yet another embodiment, the reacting step (a) of the methods of the invention is performed in the presence of an acidic catalyst. In some embodiments, the acidic catalyst is paratoluene sulfonic acid, dodecylbenzene sulfonic acid, borontrifluoride, zinc perchlorate, sulfated zirconium oxide, sulfated titanium oxide, lithium chloride, boron trifluoride etherate, ferric sulfate, zirconium oxychloride, cupric chloride, titanium tetrachloride, or zinc chloride. In other embodiments, the reacting step (a) of the methods of the invention is performed in the presence of a basic catalyst. In some embodiments, the basic catalyst is potassium acetate, sodium acetate, zinc acetate, zinc acetate dihydrate, aluminum acetate, calcium acetate, magnesium acetate, magnesium oxide, copper acetate, lithium acetate, aluminum oxide, or zinc oxide.

In certain embodiments of the invention in which the reacting step (a) of the methods of the invention is performed in the presence of a catalyst, the methods of the invention further comprise the step of inactivating the catalyst prior to production of the vapor phase. In certain embodiments, the step of inactivating the catalyst comprises forming an insoluble precipitate of the catalyst and removing the precipitate from the reaction mixture. In other embodiments, the precipitate is formed by the addition of sulfuric acid, phosphoric acid or a combination thereof. In still other embodiments, the precipitate is formed by reducing the solubility of the catalyst in the reaction mixture.

In another embodiment of the invention, the methods of the invention further comprise the step of minimizing the recovery of volatile latent acid forming impurities. In some embodiments, the step of minimizing the impurities, comprises:

(a) adding to the reaction mixture water and an acid having a pKa range of −8 to 5;

(b) adding to the reaction mixture a sterically hindered organic acid; or (c) adding to the reaction mixture a non-volatile organic acid, or any combination of (a), (b) or (c).

In other embodiments, the step of minimizing the impurities comprises adding to the reaction mixture water and an acid having a pKa range of −8 to 5.

In one embodiment of the invention, the methods of the invention are performed in the absence of a solvent. In other embodiments, the methods of the invention are performed in the presence of an acidic solvent. In still other embodiments, the methods of the invention are performed in the presence of a non-acidic solvent. In some embodiments, the non-acidic solvent is tetrahydrofuran, chloroform, dichloromethane, toluene, heptane, ethyl acetate, n-butyl acetate or hexane.

In a specific embodiment, the methods of the invention are performed in the absence of a catalyst and in the absence of a solvent.

In another specific embodiment, the methods of the invention are performed in the presence of a basic catalyst and in the absence of a solvent.

In some embodiments of the invention, wherein a redistilling step (d) is utilized, the redistilling step is by simple distillation, fractional distillation, flash distillation, steam distillation, vacuum distillation, short path distillation, thin-film distillation, reactive distillation, perevaporation, extractive distillation, flash evaporation, or rotary evaporation.

In one embodiment of the invention, the malonic acid ester reactant has the formula:

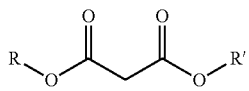

wherein R and R' are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl-($C_1$-$C_{15}$ alkyl), heteroaryl or heteroaryl-($C_1$-$C_{15}$ alkyl), or alkoxy-($C_{1-15}$ alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester; or
wherein R and R' are taken together with the atoms to which they are bound to form a 5-7 membered heterocyclic ring which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

In another embodiment of the invention, the malonic acid ester reactant the malonic acid ester is monofunctional.

In still another embodiment of the invention, the malonic acid ester reactant is difunctional.

In still another embodiment of the invention, the malonic acid ester reactant is multifunctional.

In certain embodiments of the invention, the reaction complex comprises one or more oligomeric complexes. In such embodiments, the one or more oligomeric complexes are capable of forming methylene malonate monomer as a result of conducting step (b). In other such embodiments the one or more oligomeric complexes independently comprise between 2 and 12 units of methylene malonate monomer.

A third aspect of the invention, the invention provides a methylene malonate monomer prepared by:
(a) reacting a malonic acid ester with a source of formaldehyde; optionally in the presence of an acidic or basic catalyst; and optionally in the presence of an acidic or non-acidic solvent, to form a reaction complex; and
(b) contacting the reaction complex or a portion thereof with an energy transfer means to produce a vapor phase comprising methylene malonate monomer; and
(c) isolating the methylene malonate monomer from the vapor phase.

A fourth aspect of the invention, the invention provides a methylene malonate monomer prepared by:
(a) reacting a malonic acid ester with a source of formaldehyde in the presence of heat transfer agent; optionally in the presence of an acidic or basic catalyst; and optionally in the presence of an acidic or non-acidic solvent, to form a reaction complex; and (b) producing a vapor phase comprising methylene malonate monomer from the reaction complex by heating the reaction complex to between about 150° C. and about 300° C.; and
(c) isolating the methylene malonate monomer from the vapor phase.

In a fifth aspect, the invention provides a composition comprising a methylene malonate monomer which is substantially free of acetic acid.

In a sixth aspect, the invention provides a composition comprising a methylene malonate monomer having specific functional properties without the addition of a stabilizer or other preservative compound. In certain embodiments, said composition of the invention is capable of bonding glass to a substrate in less than about 90 seconds, less than about 60 seconds, less than about 30 seconds or less than about 15 seconds. In other embodiments, said composition of the invention is capable of bonding polycarbonate to a substrate in less than about 90 seconds, less than about 60 seconds, less than about 45 seconds or less than about 30 seconds. In still other embodiments, said composition solidifies upon addition of 3% tertiary butyl ammonium fluoride (TBAF) in Dibutyl Phthalate solution in less than about 15 seconds, less than about 10 seconds, or less than about 7 seconds. In yet other embodiments, said composition remains stable at 25° C. and at atmospheric pressure for more than 10 days, more than 15 days, more than 20 days, more than 25 days or more than 30 days. In still yet other embodiments, said composition remains stable at 82° C. and at atmospheric pressure for more than about 2 hours, more than about 3 hours, or more than about 4 hours. In particular embodiments, the compositions described herein are further is substantially free of acetic acid.

In a seventh aspect, the invention provides a product comprising a methylene malonate monomer prepared according to a method of the invention, wherein the product is an adhesive, a coating, a sealant, a composite, or a surfactant.

In certain embodiments, the product of the invention further comprises an acidic stabilizer, a free radical stabilizer, a sequestering agent, a cure accelerator, a rheology modifier, a plasticizing agent, a thixotropic agents, a natural rubber, a synthetic rubbers, a filler agent, a reinforcing agent or a combination thereof.

In certain embodiments, the product of the invention further comprises a plasticizer.

In one embodiment, wherein a product of the invention comprises an acidic stabilizer, the acid stabilizer has a pKa in the range of −15 to 5; in the range of −15 to 3; or in the range of −15 to 1.

In other embodiments, wherein a product of the invention comprises an acidic stabilizer, the acid stabilizer is a volatile acid stabilizer, which has a boiling point less than 200° C.; less than 170° C.; or less than 130° C.

In still other embodiments, wherein a product of the invention comprises an acidic stabilizer, the acid stabilizer is a an acidic gas. In certain embodiments, the acidic gas is $SO_2$ or $BF_3$.

In yet other embodiments, wherein a product of the invention comprises an acidic stabilizer, the acid stabilizer is present in a concentration of 0.1 ppm to 100 ppm; 0.1 ppm to 25 ppm; or 0.1 ppm to 15 ppm.

In one embodiment, wherein a product of the invention comprises a free radical stabilizer, the free radical stabilizer is a phenolic free radical stabilizer. In other embodiments, wherein a product of the invention comprises a free radical stabilizer, the free radical stabilizer is present in a concentration of 0.1 ppm to 10000 ppm; 0.1 ppm to 3000 ppm; or 0.1 ppm to 1500 ppm. In certain other embodiments, wherein a product of the invention comprises an free radical stabilizer, the free radical stabilizer is present in a concentration of 0.1 ppm to 1000 ppm; 0.1 ppm to 300 ppm; or 0.1 ppm to 150 ppm.

In another embodiment, wherein a product of the invention comprises a sequestering agent, the sequestering agent is a crown ether, a silyl crown, a calixarene, a polyethylene glycol, or a combination thereof.

In yet another embodiment, wherein a product of the invention comprises a cure accelerator, the cure accelerator is sodium acetate, potassium acetate, tetrabutyl ammonium fluoride, tetrabutyl ammonium chloride, tetrabutyl ammonium hydroxide, a benzoate salt, a 2,4-pentanedionate salt, a sorbate salt, a propionate salt or combinations thereof.

In still yet another embodiment, wherein a product of the invention comprises the rheology modifier, the rheology modifier is hydroxyethylcellulose, ethyl hydroxyethylcellulose, methylcellulose, a polymeric thickener, pyrogenic silica or a combination thereof.

In certain embodiments, the product of the invention is stable for at least one year. In other embodiments, the level of ketals in the product of the invention is less than about 100 ppm. In still other embodiments, the levels of other latent acid-forming impurities in the product of the invention is less than about 100 ppm.

In an eighth aspect, the invention provides an adhesive product comprising a methylene malonate monomer prepared according to the methods of the invention. In certain embodiments, the adhesive composition is stable for at least one year. In other embodiments, the level of ketals in the adhesive composition is less than about 100 ppm. In still other embodiments, the levels of other latent acid-forming impurities in the adhesive composition is less than about 100 ppm.

In a ninth aspect, the invention provides a polymer comprising one or more units of a methylene malonate monomer prepared according to the methods of the invention.

In a tenth aspect, the invention provides a polymer product comprising a polymer comprising one or more units of a methylene malonate monomer prepared according to the methods of the invention. In certain embodiments, the polymer product of the invention is a sealant, a thermal barrier coating, a textile fiber, a water-treatment polymer, an ink carrier, a paint carrier, a packaging film, a molding, a medical polymer, a polymer film, a polymer fiber or a polymer sheet. In certain other embodiments, the polymer product of the invention is stable for at least one year. In other embodiments, the level of ketals in the polymer product of the invention is less than about 100 ppm. In still other embodiments, the levels of other latent acid-forming impurities in the polymer product of the invention is less than about 100 ppm.

In an eleventh aspect, the invention provides a polymer having repeat units of the formula:

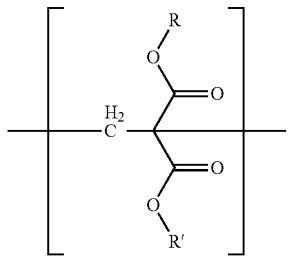

wherein R and R' are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl-($C_1$-$C_{15}$ alkyl), heteroaryl or heteroaryl-($C_1$-$C_{15}$ alkyl), or alkoxy-($C_{1\text{-}15}$ alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

In a twelfth aspect, the invention provides an oligomeric complex having a GC/MS profile which shows greater than 80% concentration of a methylene malonate monomer.

In a thirteenth aspect, the invention provides oligomeric complex having a MALDI-TOF analysis spectrum comprising peaks at: 131, 153, 176, 192, 194, 470, 472, 675, and 758.

In a fourteenth aspect, the invention provides an oligomeric complex having a proton NMR spectrum in $CDCl_3$ at 400 MHz: comprising the following peaks: a singlet at 4.66 ppm and narrow peaks located between 4.32-3.8 ppm.

In a fifteenth aspect, the invention provides an oligomeric complex having the following physiochemical properties:
1.) a GC/MS profile which shows greater than 80% concentration of a methylene malonate monomer;
2.) a MALDI-TOF analysis spectrum comprising peaks at: 131, 153, 176, 192, 194, 470, 472, 675, and 758; and
3.) a proton NMR spectrum in $CDCl_3$ at 400 MHz comprising the following peaks: a singlet at 4.66 ppm and narrow peaks located between 4.32-3.8 ppm.

In a sixteenth aspect, the invention provides an oligomeric complex prepared by reacting a malonic acid ester with a source of formaldehyde; optionally in the presence of heat transfer agent; optionally in the presence of an acidic or basic catalyst; and optionally in the presence of an acidic or non-acidic solvent.

In a seventeenth aspect, the invention provides an oligomeric complex prepared by reacting a malonic acid ester with a source of formaldehyde in a substantial absence of acidic solvent; optionally in the presence of heat transfer agent; optionally in the presence of an acidic or basic catalyst; and optionally in the presence of a non-acidic solvent. In certain embodiments, the substantial absence of acidic solvent represents less than 1.0%, less than 0.5%, less than 0.2% or less than 0.1% by weight acidic solvent as compared to the total composition of the reaction mixture.

In an eighteenth aspect, the invention provides an oligomeric complex prepared by reacting a malonic acid ester with a source of formaldehyde; optionally in the presence of heat transfer agent; optionally in the presence of an acidic or basic catalyst; and optionally in the presence of an acidic or non-acidic solvent and having one or more of the following physiochemical properties:
1.) a GC/MS profile which shows greater than 80% concentration of a methylene malonate monomer;
2.) a MALDI-TOF analysis spectrum comprising peaks at: 131, 153, 176, 192, 194, 470, 472, 675, and 758; or
3.) a proton NMR spectrum in $CDCl_3$ at 400 MHz comprising the following peaks: a singlet at 4.66 ppm and narrow peaks located between 4.32-3.8 ppm.

In a nineteenth aspect, the invention provides and oligomeric complex prepared by reacting a malonic acid ester with a source of formaldehyde; optionally in the presence of heat transfer agent; optionally in the presence of an acidic or basic catalyst; and optionally in the presence of an acidic or non-acidic solvent and having the following physiochemical properties:
1.) a GC/MS profile which shows greater than 80% concentration of a methylene malonate monomer;
2.) a MALDI-TOF analysis spectrum comprising peaks at: 131, 153, 176, 192, 194, 470, 472, 675, and 758; and 3.) a proton NMR spectrum in CDCl₃ at 400 MHz comprising the following peaks: a singlet at 4.66 ppm and narrow peaks located between 4.32-3.8 ppm.

In certain embodiments of the invention, the oligomeric complex results in a weight loss of less than 20% below 218° C. as measured by thermogravimetric analysis.

In still other embodiments of the invention, the oligomeric complex has between 2 and 12 units of methylene malonate monomer.

In a twentieth embodiment, the invention provides a methylene malonate monomer having the structure:

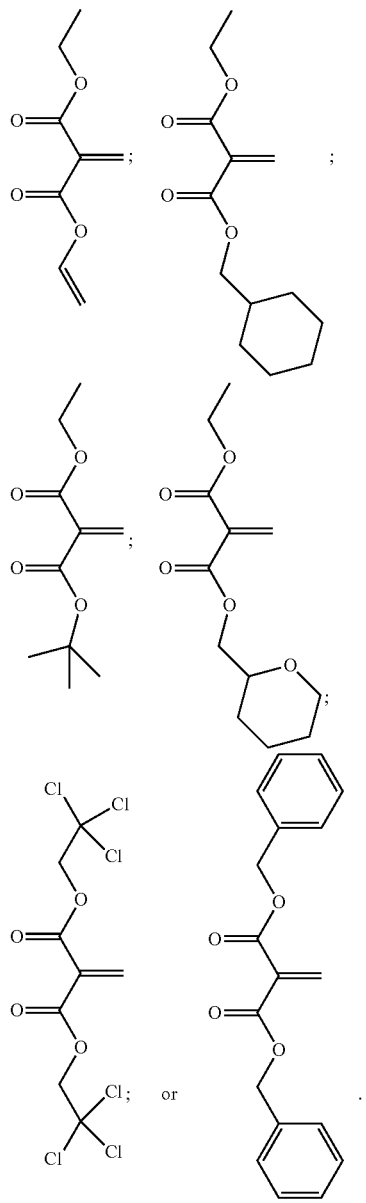

In a related embodiment, the invention provides compositions, products, adhesives, and polymers comprising one or more of these methylene malonate monomers.

BRIEF DESCRIPTION OF THE DRAWINGS

So that those having ordinary skill in the art to which the subject invention pertains will more readily understand how to make and use the invention as described herein, preferred embodiments thereof will be described in detail below, with reference to the drawings, wherein.

DESCRIPTION OF THE INVENTION

Overview

Figure 1:
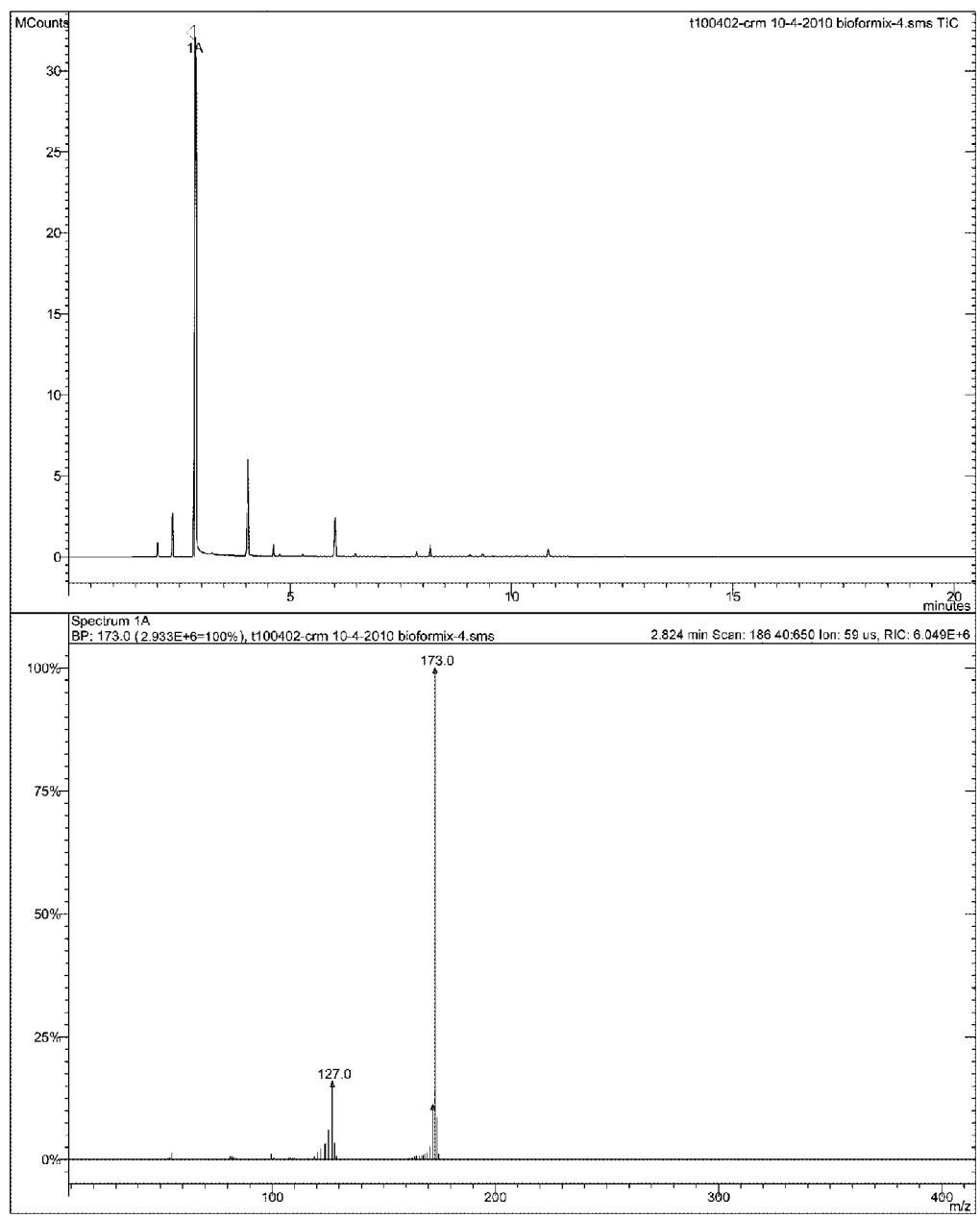
FIG. 1 depicts provides a GC-MS spectrum of crude diethyl methylene malonate monomer containing water, formaldehyde and other impurities.
Figure 2:
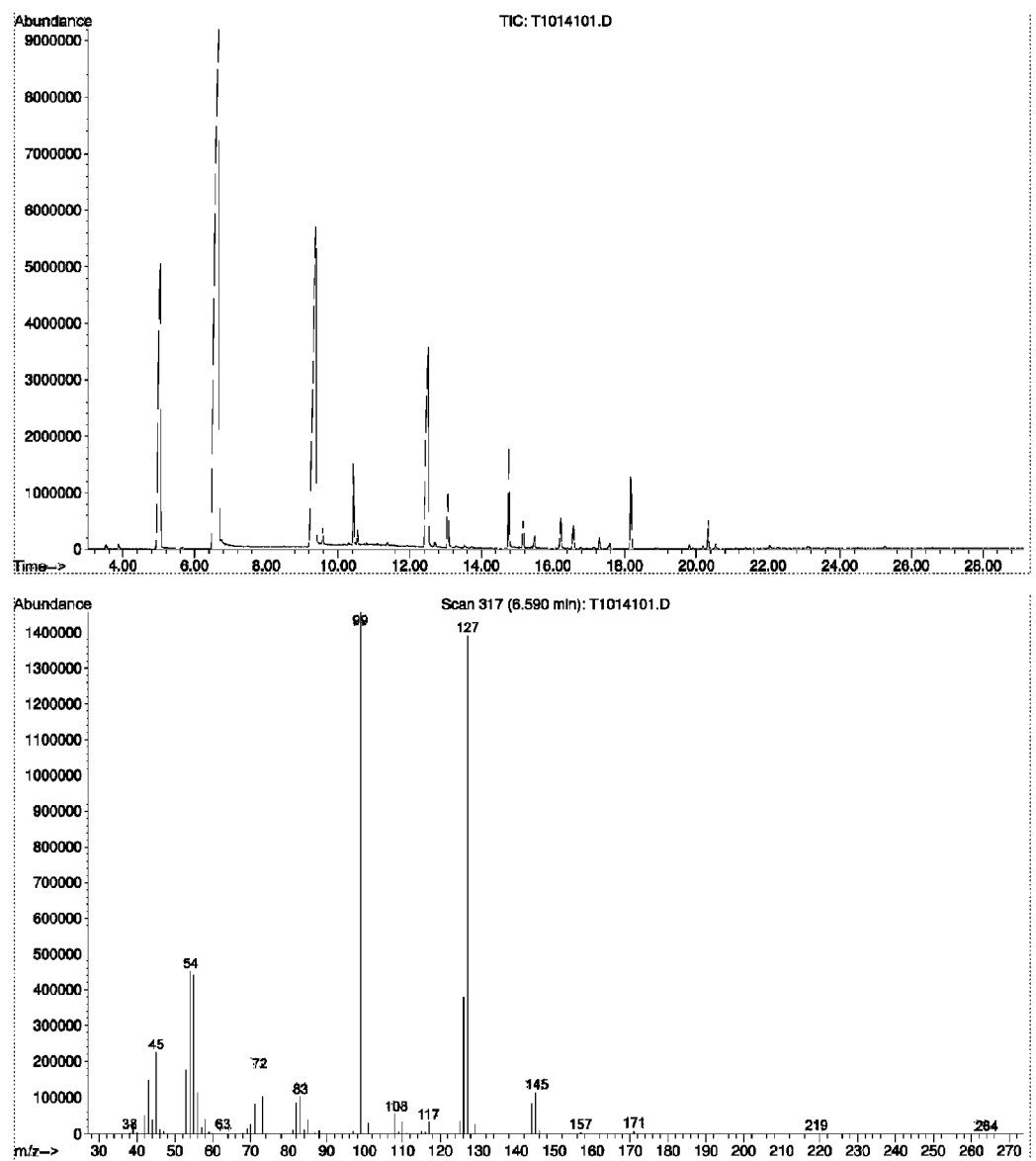
FIG. 2 depicts the depletion of the diethyl methylene malonate monomer of FIG. 1 over the course of storage at room temperature for 7 days, as depicted by GC-MS.
Figure 3:
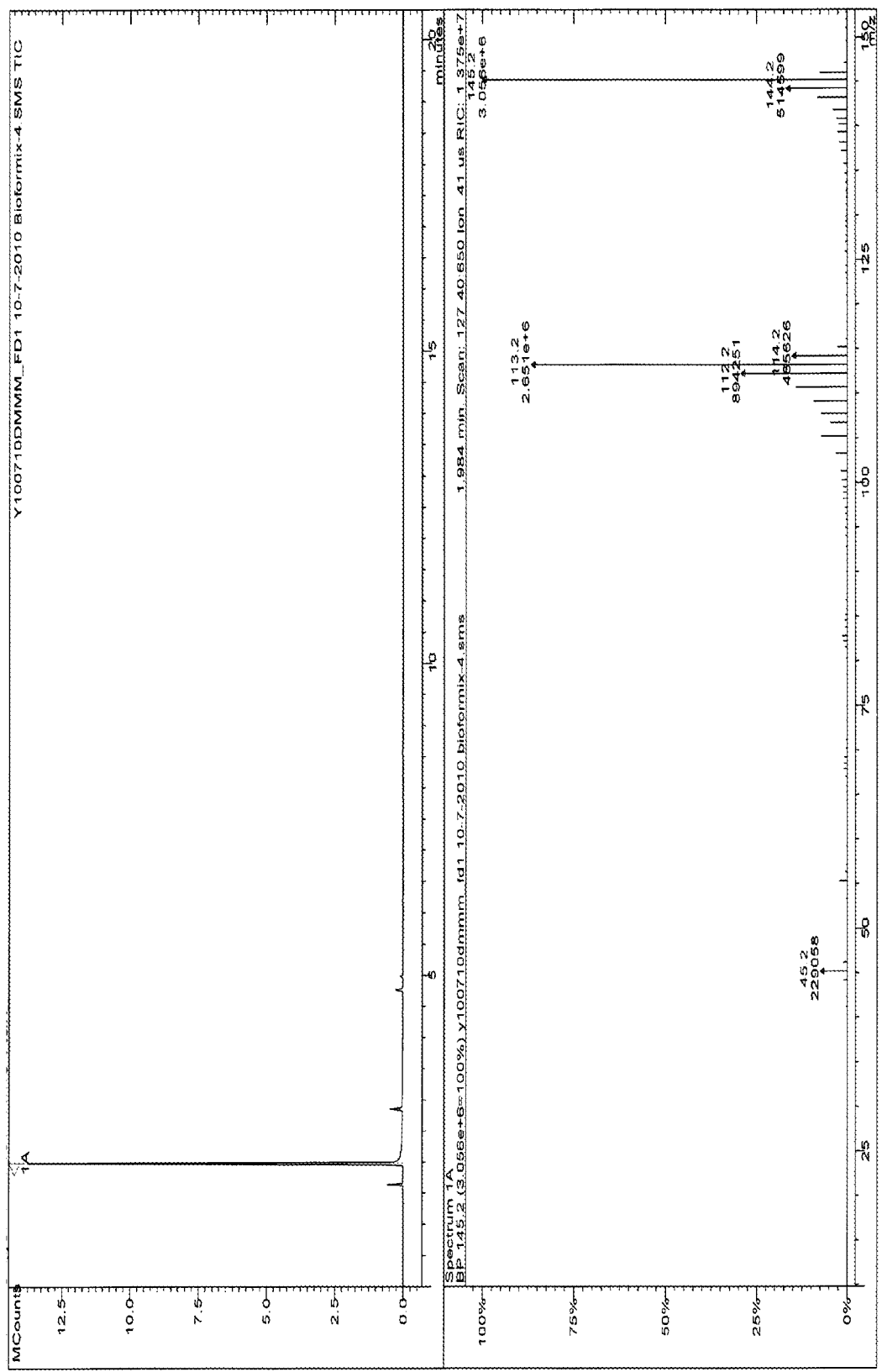
FIG. 3 depicts provides a GC-MS spectrum of crude dimethyl methylene malonate monomer containing water, formaldehyde and other impurities.
Figure 4:
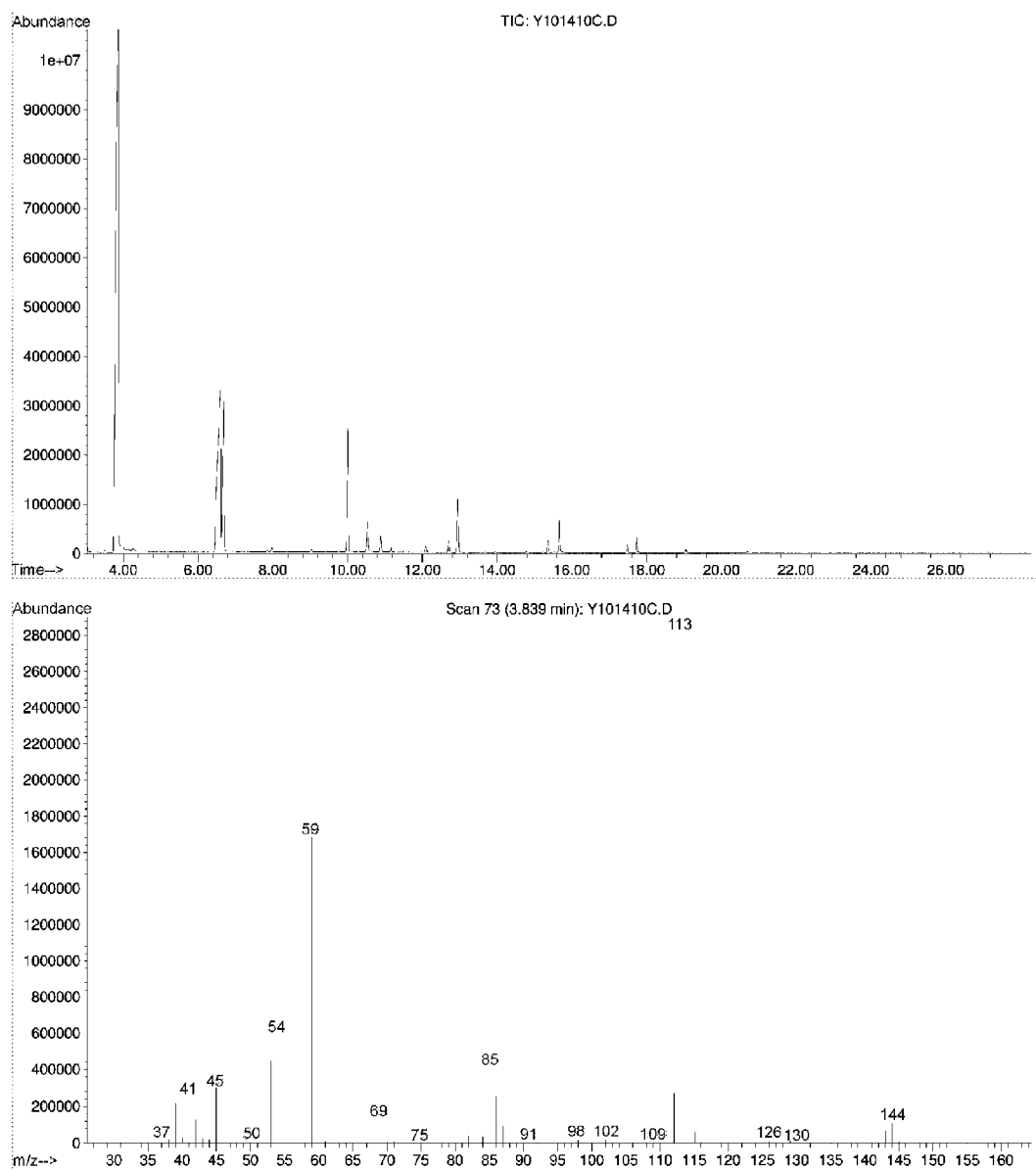
FIG. 4 depicts the depletion of the dimethyl methylene monomer of FIG. 3 over the course of storage at room temperature for 7 days, as depicted by GC-MS.

The present invention provides new and nonobvious improvements in the use and application of the Knovenagel reaction in the synthesis of methylene malonate ("MM") monomers. The inventive method is advantageous over previously known approaches for synthesizing MM monomers, in part, because the methods of the invention, inter alia, (a) significantly reduce or eliminate the formation of alternative products, (b) significantly reduce or eliminate unwanted consumption of MM monomer products, and (c) significantly reduce or eliminate the degradation of MM monomer products. These advantages result in MM monomers, which upon recovery, are of higher quality, greater purity, improved yield and possess overall improved performance characteristics (e.g., improved cure speed, retention of cure speed, improved shelf-life). Without intending to be bound by theory, the improved methods of the invention relate to the surprising discovery that the prior art entirely failed to recognize that alternative product formation, MM monomer consumption and MM degradation were widespread in prior synthesis methods and that these phenomena prevented the production of MM monomers that suitably could be used in the manufacture of MM-based products and materials.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "methylene malonate" refers to a compound having the core formula —O—C(O)—C(=CH$_2$)—C(O)—O—.

As used herein, the term "malonic acid ester" refers to a compound having the core formula —O—C(O)—CH$_2$—C(O)—O—.

As used herein, the term "malonic mono-acid mono-ester" refers to a compound having the core formula —O—C(O)—CH$_2$—C(O)—OH.

As used herein, the term "monofunctional" refers to a malonic acid ester or a methylene malonate having only one core formula.

As used herein, the term "difunctional" refers to a malonic acid ester or a methylene malonate having two core formulas bound through an alkylene linkage between one oxygen atom on each of two core formulas.

As used herein, the term "multifunctional" refers to refers to a malonic acid ester or a methylene malonate having more than one core formula which forms a chain through an alkylene linkage between one oxygen atom on each of two adjacent core formulas. In certain embodiments, the term multifunction refers to a malonic acid ester having 3, 4, 5, 6, 7, 8, 9, or 10 core formulas.

As used herein, the term "inactivating," as in inactivating the catalyst, refers to removing the catalyst or significantly reducing or eliminating the activity of the catalyst from the reaction mixture such that the catalyst no longer participates in the reaction. Such inactivation can be achieved by one of the methods described herein.

As used herein, the term "reaction complex" refers to the materials which result after reacting a malonic acid ester with a source of formaldehyde. Such reaction complexes may comprise, without limitation, methylene malonate monomers, oligomeric complexes, irreversible complex impurities, starting materials, or latent acid-forming impurities. In certain embodiments, the term "reaction complex" refers to the combination or mixture of one or more reactants, solvents, catalysts or other materials in a reaction vessel which are capable of performing a chemical reaction. The use of the term "reaction complex" does not indicate that a chemical reaction is occurring but merely conveys the combination or association of the materials within the reaction vessel. In certain embodiments, the term "reaction complex" refers to the contents of the reaction vessel. In certain embodiments, the term "reaction mixture" and "reaction complex" may be used interchangeably.

As used herein, the term "reaction vessel" refers to any container in which the reactants, solvents, catalysts or other materials may be combined for reaction. Such reaction vessels can be made of any material known to one of skill in the art such as metal, ceramic or glass.

As used herein, the term "vapor phase" as in "vapor phase comprising methylene malonate monomer" refers to a gaseous phase which may comprise, without limitation, vaporized methylene malonate monomer, vaporized starting materials; vaporized solvents, or vaporized impurities.

As used herein, the term "recovering" or "obtaining" or "isolating" as in "isolating the methylene malonate monomer", refers to the removal of the monomer from the reaction mixture, vapor phase, or condensed vapor phase by one of the methods described herein so it is in a substantially pure form.

As used herein, the term "latent acid-forming impurities" or "latent acid-forming impurity" refers to any impurity that, if present along with the recovered methylene malonate monomer, will with time be converted to an acid. The acid formed from these impurities tends to result in overstabilization of the methylene malonate monomer, thereby reducing the overall quality and reactivity of the monomer.

As used herein, the term "irreversible complex impurities" refers to any impurity that, if present in the reaction complex will not convert to a methylene malonate monomer and which may result in overstabilization of the methylene malonate monomer, thereby reducing the overall quality and reactivity of the monomer.

As used herein, the term "ketal" refers to molecule having a ketal functionality; i.e. a molecule containing a carbon bonded to two —OR groups, where O is oxygen and R represents any alkyl group.

As used herein, the term "sterically hindered" refers to a compound in which the size of groups within the molecule prevents chemical reactions that are observed in related smaller molecules.

As used herein, the terms "volatile" and "non-volatile" refers to a compound which is capable of evaporating readily at normal temperatures and pressures, in the case of volatile; or which is not capable of evaporating readily at normal temperatures and pressures, in the case of non-volatile.

As used herein, the term "energy transfer means" refers to a means which is capable of volatizing a reaction complex, usually by, but not limited to, rapidly heating the reaction complex to temperatures from about 150° C. to about 300° C. Such energy transfer means include, but are not limited to, heat transfer agents, heat transfer surfaces, lasers, and sources of radiation.

As used herein, the term "heat transfer agent" refers to a material which is capable of achieving a high temperature and transferring that temperature to a reaction mixture. Such heat transfer agents are typically able to reach temperatures from about 150° C. to about 300° C. and include, but are note limited to silica, silicone oil, mineral oil, a petroleum based heat transfer oil or a synthetic chemical based heat transfer oil. In certain embodiments, the heat transfer agent can be pre-formed reaction complex.

As used herein the term "pre-formed reaction complex" refers to a reaction complex as defined herein which is prepared by reacting step (a) as described herein in advance of the vaporization step (b). Such pre-formed reaction complexes can be formed up to a year, up to six months, up to 3 months, up to 1 month, up to 2 weeks, up to 1 week, up to 3 days, or up to 1 day in advance of the vaporization step (b). In such instances, the vaporization step (b) is performed on a newly prepared reaction complex. In certain aspects the pre-formed reaction complex can refer to an oligomeric complex as defined herein.

As used herein the term "substantial absence" as in "substantial absence of acidic solvent" refers to a reaction mixture which comprises less than 1% by weight of the particular component as compared to the total reaction mixture. In certain embodiments, a "substantial absence" refers to less than 0.7%, less than 0.5%, less than 0.4% m less than 0.3%, less than 0.2% or less than 0.1% by weight of the of the particular component as compared to the total reaction mixture. In certain other embodiments, a "substantial absence" refers to less than 1.0%, less than 0.7%, less than 0.5%, less than 0.4% m less than 0.3%, less than 0.2% or less than 0.1% by volume of the of the particular component as compared to the total reaction mixture.

As used herein, the term "stabilized," e.g., in the context of "stabilized" methylene malonates or compositions comprising same, refers to the tendency of the methylene malonates (or their compositions) of the invention to substantially not polymerize with time, to substantially not harden, form a gel, thicken, or otherwise increase in viscosity with time, and/or to substantially show minimal loss in cure speed (i.e., cure speed is maintained) with time.

As used herein, the term "shelf-life," e.g., as in the context of methylene malonates having an improved "shelf-life," refers to the methylene malonates of the invention which are stabilized for a given period of time, e.g., 1 month, 6 months, or even 1 year or more.

Knovenagel Synthesis

The present invention contemplates an improved Knovenagel synthesis reaction for the synthesis of MM monomers, wherein the method, inter alia, (a) significantly reduces or eliminates the formation of alternative products, (b) significantly reduces or eliminates unwanted consumption of MM monomers and (c) significantly reduces or eliminates the degradation of MM monomers in the reaction and subsequent recovery and storage stages. These advantages are achieved based on the improvements discussed below.

The Knovenagel reaction with formaldehyde for the synthesis of methylene malonate monomers has been previously described. The typical Knovenagel reaction combines one mole of a malonic acid ester (e.g., a mono- or disubstituted malonate) and one mole of formaldehyde to form, via catalytic (chemical reaction) action in the presence of a basic catalyst and an acidic solvent, a methylene malonate monomer, as depicted in Schematic 1, below.

Schematic 1. Knovenagel reaction with formaldehyde for the synthesis of a methylene malonates.

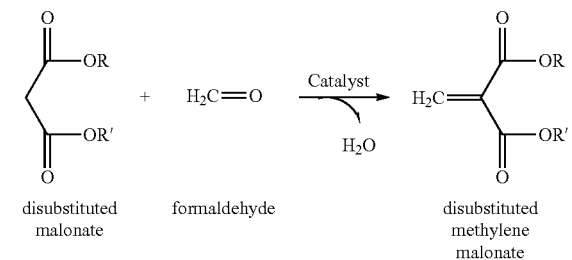

disubstituted malonate     formaldehyde     disubstituted methylene malonate

This reaction scheme is, however, fraught with difficulties. And, in most instances, the prior art did not even recognize its own problems. For instance, prior art use of the Knovenagel synthesis for preparing methylene malonates is typically carried out under conditions that lead to the formation of many different kinds of deleterious side products. In one example, the prior art teaches to conduct the Knovenagel reaction under acidic solvent conditions, for example, in acetic acid. The acetic acid or other weak organic acid then reacts with the formaldehyde to form a ketal, as depicted in the below schematic. The ketals co-distill with the methylene malonates and result in the contamination of the final preparation of the product. Over time, the ketals in the presence of water (spontaneously) hydrolyze and revert back to its acid form thereby increasing the acidic conditions of the product. The increased concentration of acid impinges on the ability of the monomer to polymerize, i.e., causing over stabilization of the monomer such that its overall reactivity and performance are significantly reduced.

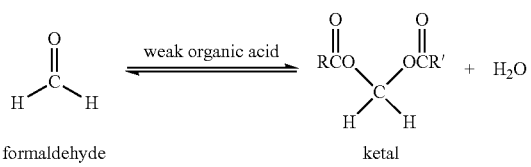

Besides ketal formation, the prior art was similarly unaware that its conditions for Knovenagel synthesis also led to the formation of other latent acid-forming species. These chemical species are formed as a result of various unintended side reactions that occur between reactants, or between reactants and solvent, or between reactants, solvents and products and even intermediate species that may form during the course of the reaction. These additional latent acid-forming species lead to the same result as the ketals, namely, that they are contaminants in the final methylene malonate product and with time they are converted back to an acid. These increasing acidic conditions, like with ketals, lead to the overall reduction in the reactivity and performance of the monomer products.

An example of another impediment to forming high quality monomer through the Knovenagel reaction is the unwanted polymerization of the monomer. These polymerizations can occur via polymerization of the monomers themselves, or of the monomers and various intermediates, or of the monomer and other side products that may be present in the reaction mixture under conditions used in the prior art. These polymerizations not only lead to unwanted consumption of the monomer product, but also may lead to the formation of other side products that may or may not become co-distilled with the methylene monomers themselves, causing the monomer product to become contaminated with unwanted side products that may impinge on the overall performance of the monomers.

Other deleterious events are also possible during the Knovenagel reaction, in particular, those events that result in the consumption of monomer or raw starting materials and the reduction in the yield of the desired methylene malonate product. For example, the methylene group can react with 2 formaldehyde molecules to form a dimethyl-ol material, which consumes raw material and is nonreactive. The malonate raw material can also react with a methylene malonate already formed, instead of formaldehyde, to produce a glutarate, which is also non-reactive and consumes raw material. In addition, the desired products formed can polymerize thereby reducing the yield of desired product.

Exemplary evidence of deleterious side-reaction formation occurring during the Knovenagel reaction with formaldehyde has been observed by the present inventors, it is believed for the first time. The observed phenomenon is that methylene malonate monomers already formed by the Knovenagel reaction with formaldehyde, if left to stand at room temperature for a period of time, form a mixture that varies in composition to include various side products. In several observed cases, crude products still containing some amount of formaldehyde and water after 7 days, were reduced in yield by up to 40% due to the consumption of the already formed methylene malonate monomers in deleterious side reactions with other components of the reaction mixture. See, for example, FIGS. 1, 2, 3 and 4. The methylene malonates prepared under such conditions are unsuitable for use in making commercial products, including reactive formulated products, such as reactive adhesives, and polymer products, such as films, fibers, molded articles and the like.

Importantly, while a substantial amount of prior art exists on the use of the Knovenagel reaction for the preparation of methylene malonates (e.g., see U.S. Pat. Nos. 2,313,501; 2,330,033; 3,221,745; 3,523,097; 3,557,185; 3,758,550; 3,975,422; 4,049,698; 4,056,543; 4,160,864; 4,931,584; 5,142,098; 5,550,172; 6,106,807; 6,211,273; 6,245,933; 6,420,468; 6,440,461; 6,512,023; 6,610,078; 6,699,928; 6,750,298; and 2004/0076601, each of which are incorporated by reference), and the Knovenagel reaction for the synthesis of methylene malonates has been known at least since 1938 (see e.g., U.S. Pat. No. 2,313,501), the prior art did not recognize the above significant limitations. This is further evidenced by the fact that no single commercial product based on methylene malonates has ever been marketed or sold, including where the methylene malonates have been made using the Knovenagel reaction.

The present invention relates to an improved Knovenagel synthesis reaction involving the condensation of malonic acid esters with formaldehyde to form methylene malonate monomers. An important feature of the improved method of the invention is the surprising discovery that catalyst inactivation provides for, inter alia, (a) significantly reduced or eliminated formation of alternative products, (b) significantly reduced or eliminated consumption of MM monomers and (c) significantly reduced or eliminated degradation of MM monomers in the reaction and during subsequent recovery and storage stages. To the inventors' knowledge, catalyst inactivation has not previously been recognized or contemplated in the context of using the Knovenagel reaction with formaldehyde to synthesize methylene malonates.

Accordingly, the present invention relates, in part, to the complete or substantial inactivation of the reaction catalyst to eliminate or significantly reduce the reactivity or subsequent further reaction of the mixture, which can lead to methylene malonate consumption, degradation or the formation of alternate products, all of which can impede yield optimization, methylene malonate purification and methylene malonate polymerization and other aspects of product performance and manufacture. The prior art that employs the Knovenagel reaction to synthesize methylene malonates does not in any way teach, suggest or exemplify this additional step. By contrast, the prior art methods for synthesizing methylene malonates are associated with a variety of problems which preclude their use in making viable MM-based products. Such problems include, for example, large-scale losses in monomer yield due to monomer degradation during the reaction and subsequent recovery stages, generation of unwanted, deleterious alternate products during the reaction and downstream processes, and the production of metal and acid/base residues from the catalyst, which become concentrated during recovery. These problems can significantly impinge on the overall quality of the monomers, their reactivity, stability and capacity for forming viable commercial products. For example, in the case of adhesives, these kinds of problems lead to a significant reduction in the cure speed and an overall reduction in shelf-life of the product.

While the invention generally relates to an improved Knovenagel reaction with formaldehyde to synthesize methylene malonate monomers, the general concepts of the invention can be applied by those having ordinary skill in the art to any approach to chemically synthesize methylene malonates. Namely, the general discovery that methylene malonate product and monomer performance is particularly sensitive to the presence of unwanted alternative products, monomer degradation and monomer consumption is widely applicable to any type of synthesis that can be used to generate methylene malonates. Prior to the present invention, the significance and nature of these types of impurities and their effects on the performance and quality of methylene malonates was not previously recognized. Thus, for the first time, the present invention provides a viable approach to producing methylene malonate monomers that can be utilized as the basis for viable consumer and industrial monomer-based (e.g., adhesives) and polymer-based (e.g., fibers) products.

In certain embodiments of the invention, the reacting step is performed at about 60° C. to about 130° C. Depending on the source of formaldehyde used, the reaction step can be performed at about 20° C. to about 50° C., or about 30° C. to about 40° C. In still other instances, particularly, though not limited to, instances when the source of formaldehyde is a gas, the reaction step can be performed at about 0° C. to about 25° C.—provided the reaction mixture is a liquid at such temperatures.

Reactants

The Knovenagel reaction for making methylene malonates of the invention includes at least two basic reactants: a malonic acid ester and a source of formaldehyde.

In certain embodiments, the present invention contemplates the use of malonic acid esters having the following formula:

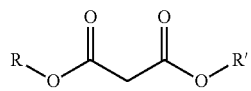

wherein R and R' are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl-($C_1$-$C_{15}$ alkyl), heteroaryl or heteroaryl-($C_1$-$C_{15}$ alkyl), or alkoxy-($C_{1-15}$ alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester; or
wherein R and R' are taken together with the atoms to which they are bound to form a 5-7 membered heterocyclic ring which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

In certain other embodiments, the present invention contemplates the following specifically identified malonic acid esters: dimethyl, diethyl, ethylmethyl, dipropyl, dibutyl, diphenyl, and ethyl-ethylgluconate, among others.

In certain other embodiments, the present invention contemplates the use of malonic acid esters having the following formula:

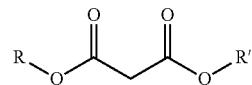

wherein R and R' are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl-($C_1$-$C_{15}$ alkyl), heteroaryl or heteroaryl-($C_1$-$C_{15}$ alkyl), or alkoxy-($C_{1-15}$ alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

The malonic acid esters may be derived or obtained from any source, including any commercial source, derived from nature, other compounds, synthesized by other processes, etc. In certain embodiments, the malonic acid esters are obtained from "green" sources. For example, the malonic acid esters can be derived from biological sources, such as via fermentation production systems whereby microorganisms generate the malonic acid esters as direct metabolic by-products of fermentation—or whereby the microorganisms generate metabolic by-products of fermentation that can be then converted inexpensively to the desired malonic acid esters. These fermentation production systems are well-known in the art and may utilize either—or both—microorganisms derived from nature or engineered microorganisms that are specifically designed to produce the desired malonic acid ester products, e.g., recombinant or engineered *Escherichia coli*.

In another embodiment of the invention, the malonic acid ester reactant is mono functional.

In still another embodiment of the invention, the malonic acid ester reactant is difunctional.

In still another embodiment of the invention, the malonic acid ester reactant is multifunctional.

In certain embodiments, the present invention contemplates the use of malonic mono-acid mono-esters having the following formula:

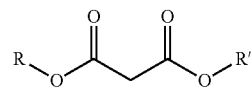

wherein one of R and R' is hydrogen and the other is are $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl-($C_1$-$C_{15}$ alkyl), heteroaryl or heteroaryl-($C_1$-$C_{15}$ alkyl), or alkoxy-($C_{1-15}$ alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

In another embodiment of the invention, the malonic mono-acid mono-ester reactant is monofunctional.

In still another embodiment of the invention, the malonic mono-acid mono-ester reactant is difunctional.

In still another embodiment of the invention, the malonic mono-acid mono-ester reactant is multifunctional.

The malonic mono-acid mono-esters may be derived or obtained from any source, including any commercial source, derived from nature, other compounds, synthesized by other processes, etc. In certain embodiments, the malonic mono-acid mono-esters are obtained from "green" sources. For example, the malonic mono-acid mono-esters can be derived from biological sources, such as via fermentation production systems whereby microorganisms generate the malonic mono-acid mono-esters as direct metabolic by-products of fermentation—or whereby the microorganisms generate metabolic by-products of fermentation that can be then converted inexpensively to the desired malonic mono-acid mono-esters. These fermentation production systems are well-known in the art and may utilize either—or both—microorganisms derived from nature or engineered microorganisms that are specifically designed to produce the desired malonic mono-acid mono-esters products, e.g., recombinant or engineered *Escherichia coli*.

In certain other embodiments, the present invention contemplates the use of malonic di-acids having the following formula:

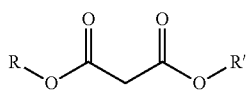

wherein R and R' are both hydrogen.

The malonic di-acids may be derived or obtained from any source, including any commercial source, derived from nature, other compounds, synthesized by other processes, etc. In certain embodiments, the malonic di-acids are obtained from "green" sources. For example, the malonic di-acids can be derived from biological sources, such as via fermentation production systems whereby microorganisms generate the malonic di-acids as direct metabolic by-products of fermentation—or whereby the microorganisms generate metabolic by-products of fermentation that can be then converted inexpensively to the desired malonic di-acids. These fermentation production systems are well-known in the art and may utilize either—or both—microorganisms derived from nature or engineered microorganisms that are specifically designed to produce the desired malonic di-acids products, e.g., recombinant or engineered *Escherichia coli*.

Further reference to the methods, materials and procedures for preparing and/or obtaining monofunctional, difunctional and multifunctional malonic acids, malonic di-acids, or malonic mono-acid mono-esters can be found in U.S. Pat. No. 7,663,000 (Quinoneimines of malonic acid diamides); U.S. Pat. No. 7,553,989 (Malonic acid monoesters and process for producing the same); U.S. Pat. No. 7,208,621 (Malonic acid monomethyl derivatives and production process thereof); U.S. Pat. No. 7,109,369 (Malonic acid monomethyl derivatives and production process thereof); U.S. Pat. No. 6,794,365 (Malonic acid derivatives, processes for their preparation their use and pharmaceutical compositions containing them); U.S. Pat. No. 6,673,957 (Method for producing alkoxy malonic acid dinitriles); U.S. Pat. No. 6,613,934 (Enantiomerically enriched malonic acid monoesters substituted by a tertiary hydrocarbon radical, and their preparation); U.S. Pat. No. 6,559,264 (Malonic acid ester/triazole mixed blocked HDI trimer/formaldehyde stabilization); U.S. Pat. No. 6,395,931 (Malonic acid and esters thereof); U.S. Pat. No. 6,395,737 (Malonic acid derivatives, processes for their preparation, for their use and pharmaceutical compositions containing them); U.S. Pat. No. 6,284,915 (Process for preparing 2-amino malonic acid derivatives and 2-amino-1,3-propanediol derivatives, and intermediates for preparing the same); U.S. Pat. No. 6,238,896 (Process for producing malonic acid derivatives); U.S. Pat. No. 5,886,219 (Process for preparing malonic acid and alkylmalonic acids); U.S. Pat. No. 5,817,870 (Process for the production of malonic acid or a salt thereof); U.S. Pat. No. 5,817,742 (Polymer-conjugated malonic acid derivatives and their use as medicaments and diagnostic agents); U.S. Pat. No. 5,693,621 (Malonic acid derivatives having antiadhesive properties); U.S. Pat. No. 5,426,203 (Platinum complexes of malonic acid derivatives and process for the preparation thereof); U.S. Pat. No. 5,334,747 (Method of preparing substituted malonic ester anilides and malonic acid mono-anilides); U.S. Pat. No. 5,292,937 (Use of malonic acid derivative compounds for retarding plant growth); U.S. Pat. No. 5,210,222 (Process for the production of malonic acid anhydride); U.S. Pat. No. 5,162,545 (Malonic acid dyes and polycondensation products thereof); U.S. Pat. No. 5,039,720 (Aqueous electrophoretic enamel coating materials, which can be deposited at the cathode crosslinked with methane tricarboxylic acid amides of malonic acid derivatives); U.S. Pat. No. 5,021,486 (Hindered amine-substituted malonic acid derivatives of s-triazine); U.S. Pat. No. 4,914,226 (Malonic acid derivatives and methods for their synthesis); U.S. Pat. No. 4,835,153 (Malonic acid derivatives); U.S. Pat. No. 4,736,056 (Process for the production of malonic acid derivative compounds); U.S. Pat. No. 4,698,333 (Use of substituted malonic acid derivatives as agents for combating pests); U.S. Pat. No. 4,578,503 (Alkylated or alkenylated malonic acid or its derivatives having a fluorine); U.S. Pat. No. 4,556,649 (Substituted malonic acid diamide insecticides, compositions and use); U.S. Pat. No. 4,539,423 (Process for preparing diesters of malonic acid); U.S. Pat. No. 4,517,105 (Metalworking lubricant composition containing a novel substituted malonic acid diester); U.S. Pat. No. 4,504,658 (Epimerization of malonic acid esters); U.S. Pat. No. 4,444,928 (Polymeric malonic acid derivatives); U.S. Pat. No. 4,443,624 (Method of preparing malonic acid dialkyl esters); U.S. Pat. No. 4,399,300 (Method of preparing malonic acid dialkyl esters); U.S. Pat. No. 4,329,479 (Process for producing 1,3-dithiol-2-ylidene malonic acid dialkyl esters); U.S. Pat. No. 4,256,908 (Process for preparing diesters of malonic acid); U.S. Pat. No. 4,237,297 (Piperidine containing malonic acid derivatives); U.S. Pat. No. 4,198,334 (Substituted malonic acid derivatives and their use as stabilizers); U.S. Pat. No. 4,154,914 (Process for producing acrylic rubber by copolymerizing acrylic ester and malonic acid derivative having active methylene group); U.S. Pat. No. 4,105,688 (Process for the production of malonic acid dinitrile and purification thereof); U.S. Pat. No. 4,102,809 (Malonic acid composition for thermoparticulating coating); U.S. Pat. No. 4,079,058 (Process of performing cyclization reactions using benzyl or pyridylamino malonic acid derivatives); U.S. Pat. No. 4,046,943 (Malonic acid derivative composition for forming thermoparticulating coating); U.S. Pat. No. 4,036,985 (Mono substituted malonic acid diamides and process of preparing them); U.S. Pat. No. 3,995,489 (Malonic acid derivative composition for forming thermoparticulating coating); U.S. Pat. No. 3,936,486 (Process for the production of malonic acid dinitrile), each of which are incorporated by reference in their entireties by reference herein.

The methods of the invention also contemplate any suitable source of formaldehyde. For example, the formaldehyde may be synthesized, derived from another chemical species (e.g., paraformaldehyde), or obtained from nature or from some other suitable source. In certain embodiments, the formaldehyde is introduced in the form of a gas. In certain embodiments, the formaldehyde is obtained from paraformaldehyde. Commercial sources of formaldehyde and paraformaldehyde are readily available, which may include, for example, trioxane and formalin (e.g., aqueous formaldehyde).

Catalysts

The present invention contemplates the use of any suitable acidic or basic catalyst. In certain preferred aspects, it has been surprisingly found that no catalyst at all is required to conduct the reaction.

In certain embodiments, catalysts that are typically used for Knovenagel reactions with formaldehyde to make MM monomers are contemplated. Such catalysts include, for example, basic catalyst salts, such as, potassium acetate and the neutral co-catalyst copper acetate.

In certain other embodiments, the present invention contemplates catalysts that hetetofore were previously unused in the context of the Knovenagel reaction with formaldehyde to synthesize MM monomers. Such catalysts include various acidic, basic, neutral, or even amphoteric catalysts.

Acidic catalysts can include, for example, lithium chloride, boron trifluoride etherate, ferric sulfate, zirconium oxychloride, cupric chloride, titanium tetrachloride, zinc chloride, aluminum oxide, or zinc oxide. Accordingly, the acidic catalysts of the invention may include, but are not limited to, paratoluene sulfonic acid, dodecylbenzene sulfonic acid, borontrifluoride, zinc perchlorate, sulfated zirconium oxide, sulfated titanium oxide, lithium chloride, boron trifluoride etherate, ferric sulfate, zirconium oxychloride, cupric chloride, titanium tetrachloride, and zinc chloride.

Neutral catalysts can also include silica and other insoluble surface active agents.

In certain other embodiments, the inventive methods utilize a basic catalyst. Basic catalysts of the invention may include, but are not limited to, potassium acetate, sodium acetate, zinc acetate, zinc acetate dihydrate, aluminum acetate, calcium acetate, magnesium acetate, magnesium oxide, copper acetate, lithium acetate, aluminum oxide, and zinc oxide.

In still further embodiments, the amphoteric catalysts can include, but are not limited to, aluminum oxide, aluminum acetate, zinc acetate, magnesium acetate, and zinc oxide.

In still other embodiments, the present inventors have surprisingly and unexpectedly found that no catalyst is required to conduct the Knovenagel synthesis reaction of the invention. Specifically, in this embodiment, the reaction can be conducted with all of the reactants added to the reaction vessel at the start of the reaction prior to adding heat. The source of formaldehyde in this embodiment is preferably solid paraformaldehyde, and is added along with the other reactants, including the malonic ester, prior to adding heat. This reaction surprisingly can be run rapidly and in a continuous mode and unexpectedly avoids the formation of—or substantially minimizes the formation of—deleterious side products, unwanted polymerization complexes and degradation of the monomer products.

Catalyst Inactivation

In the context of the Knovenagel reaction with formaldehyde, the advantages of the inventive method, including, (a) significantly reduced or eliminated formation of alternative products, (b) significantly reduced or eliminated consumption of MM monomers and (c) significantly reduced or eliminated degradation of MM monomers in the reaction and during subsequent recovery and storage stages, are achieved, in part, by the inactivation of the catalyst used in the reaction.

Where a catalyst is utilized in the improved Knovenagel reaction of the invention, the present invention can include the step of catalyst inactivation.

Any suitable method or approach for inactivating the catalyst is contemplated by the present invention. In certain embodiments, it is desirable that the method for inactivating the catalyst fully eliminates the activity of the catalyst, i.e., 100% elimination of catalytic activity. In other embodiments, it is preferred that the activity of the catalyst is reduced by at least 50%, or at least by 55%, or at least by 60%, or at least by 65%, or at least by 70%, or at least by 75%, or at least by 80%, or at least by 85%, or at least by 90%, or at least by 95%, or at least by 99% relative to the activity of the catalyst absent the conditions that cause the inactivation, i.e., relative to 100% catalytic activity.

In one embodiment, catalyst inactivation can be achieved by the addition of an agent that leads to formation of an insoluble precipitate that can be filtered or otherwise physically separated from the reaction mixture or methylene malonates. The agent can be, for example, an acid that is added in an equimolar amount or in some excess (e.g., about 2×, or 3×, or 4× equimolar) to the molar amount of catalyst used. Additional solvents or other ingredients may be added to facilitate filtration. Additional agents can include chelating agents or sequestering agents that complex the catalyst to remove it from active participation in the reaction, or agents that would form micelles (i.e., small regions or particles of another liquid phase that would remove the catalyst from active participation in the reaction) to inactivate the catalyst. For example, in certain embodiments where acidic catalysts are used, the agent used to precipitate the catalyst can be sulfuric acid, phosphoric acid, sulfurous acid, $P_2O_5$, phosphorous acid, perchloric acid, hydrochloric acid, or acidic ion exchange resins. In certain embodiments where basic catalysts are used, the agent used to precipitate the catalyst can be sulfuric acid, phosphoric acid, sulfurous acid, $P_2O_5$, phosphorous acid, perchloric acid, hydrochloric acid, or acidic ion exchange resins.

In another embodiment, catalyst inactivation can be achieved by adjusting the relative solubility of the catalyst, for example, by changing the reaction mixture composition or using temperature or both to facilitate precipitation or phase transfer or both of the catalyst and/or its components. Additional solvents or other ingredients may be added to facilitate filtration or the chosen separation method (for example, lowering viscosity). Additional solvents can include, for example, hydrocarbon solvents, ethers, long chain esters, solvents that are non-polar, etc.

In a particular embodiment, wherein the reaction utilizes a copper and/or potassium acetate catalyst in an acetic acid/hydrocarbon solvent, the catalyst may be removed by the addition of sulfuric acid in a slight molar excess to the catalyst used in the reaction mixture after the reaction is complete. The product can then be distilled at low pressure (1 mm Hg) or so. Chlorodifluoroacetic acid can be added (10 ppm) along with 1000 ppm of hydroquinone (or butylated hydroxytoluene which is by comparison more soluble). The purified product can then be distilled again at low pressure (1 mm Hg or so). Chlorodifluoroacetic acid can be added (10 ppm) along with 1000 ppm of hydroquinone (or butylated hydroxytoluene which is by comparison more soluble), either after or prior to distillation, to either the reaction mixture or the collection flask or both.

In certain embodiments, wherein the catalyst is copper acetate and potassium acetate, catalyst inactivation can be accomplished by the following procedure:

1. Paraformaldehyde is placed in toluene/acetic acid solvent with the copper acetate and potassium acetate catalysts and heated to 60° C. to produce formaldehyde and entrain it in the solvent.
2. Diethyl malonate is added gradually to the reaction mixture over a period of 30 minutes while allowing the water being formed to escape or be collected in a dean stark trap. The exotherm is observed around 80° C.-85° C. and the reaction mixture becomes transparent blue after consumption of all paraformaldehyde.

3. The reaction is allowed to continue for 60 minutes.
4. Sulfuric acid in a slight molar excess to the catalyst is added to neutralize and precipitate the catalyst and stabilize the produced methylene malonate.
5. Filtration can be done by using a glass funnel with integral fritted disc.
6. The solvent is removed by rotary evaporation under reduced pressure.
7. The methylene malonate product is collected by distillation at about 1 mm and a temperature of 60° C. and stabilized with strong acid and other traditional stabilizers in the collection flasks such that the final concentration is about (10 ppm) sulfuric acid. The purified product is then optionally distilled again at low pressure (1 mm or so). As a typical example, sulfuric acid is added (10 ppm), either after or prior to distillation, to either the reaction mixture or the collection flask or both.

Further options for catalyst inactivation could include:
1. A solvent might be used that would azeotrope the water for more rapid removal
2. With monomeric formaldehyde it might be possible to run the reaction at lower temperature.
3. Without solvent or with a higher boiling solvent higher reaction temperature would allow more rapid reaction In yet another embodiment entirely, the reaction can be conducted completely in the absence of any reaction catalyst. An advantage of this condition is the avoidance or minimization of the formation of impurities, e.g., ketals and other latent acid-forming species.

In still another embodiment, the reaction can be conducted in the presence of a reaction catalyst. An advantage of this condition is the avoidance or minimization of the formation of impurities, e.g., ketals and other latent acid-forming species.

Solvents

The present invention contemplates that the Knovenagel reaction can include an acidic or non-acidic solvent, or optionally no solvent at all.

Non-acidic solvents can include, but are not limited to, tetrahydrofuran, chloroform, dichloromethane, toluene, heptane, ethyl acetate, n-butyl acetate, dibutyl ether and hexane.

Acidic solvents can include, but are not limited to acetic acid and propionic acid.

In certain embodiments, the acidic solvent is added just prior to recovery.

In certain other embodiments, optionally no solvent is needed. This zero-solvent approach will not only decrease the overall cost of production but will also help to lessen any negative impact on the environment caused by the methods of the invention, i.e., provides an environmentally-friendly approach to the synthesis of methylene malonates. An advantage of this condition is the avoidance or minimization of the formation of impurities, e.g., ketals and other latent acid-forming species.

In still other embodiments, the present inventors have surprisingly and unexpectedly found that the Knovenagel reaction of the invention may be conducted in the absence of both a solvent and a catalyst. Specifically, in this embodiment, the reaction can be conducted with all of the reactants added to the reaction vessel at the start of the reaction prior to adding heat and in the absence of a solvent. The source of formaldehyde in this embodiment is preferably solid paraformaldehyde, and is added along with the other reactants, including the malonic ester, prior to adding heat. This reaction surprisingly can be run rapidly and in a continuous mode and unexpectedly avoids the formation of—or substantially minimizes the formation of—deleterious side products, unwanted polymerization complexes and degradation of the monomer products.

Reduction of Side Products

Prior art involving the Knovenagel reaction with formaldehyde to synthesize methylene malonates typically involves using an acidic solvent, typically acetic acid, as a means of controlling the reaction parameters. Such processes, while producing methylene malonates, lead to numerous deleterious side reactions and products, including the production of ketals and other latent acid forming species between the acid solvent and the formaldehyde. The impurities can reduce monomer quality, purity and performance as a result of the later conversion of the ketals and the other latent acid forming species to acidic species, which inhibit the polymerization capacity and cure speed of the monomers, among other problems (e.g., decompose the methylene malonate esters).

In certain embodiments, the present invention includes the further step of minimizing the formation of ketals and other deleterious side products.

In one embodiment, this can be achieved by the addition of water and a medium to strong acid (i.e., an acid having a pKa range from about −8.0 to about 5.0), either organic or inorganic, to the reaction mixture to reverse the ketal formation and destroy the ketal prior to distillation or after distillation, but prior to any subsequent distillation. Water may be made present by making a solution of the acid or by direct addition. For example, this may be accomplished by adding 1% water (based on the volume of the reaction or monomer solution) or the addition of 5% sulfuric acid solution.

In another embodiment, this can be achieved by the use of a sterically hindered organic acid to reduce or eliminate ketal formation during the reaction or any subsequent heating operation. Sterically hindered organic acids can include, for example, pivalic acid. The invention is not limited to pivalic acid, however, and may include any suitable sterically hindered organic acid.

In still another embodiment, this can be achieved by the use of high enough molecular weight organic acids that formed ketals do not co-distill with the methylene malonate. High molecular weight organic acids used for this purpose can include, but are not limited to, hexanoic acid, decanoic acid, or octanoic acid, or the like.

In yet another embodiment, as noted above, the reaction may be carried out totally in the absence of any acid solvent or in the presence of a minimal amount thereof. If a minimal amount of the acid solvent is used, the acid solvent is preferably in the range of about 1-5% v/v. An advantage of this condition is the avoidance or minimization of the formation of impurities, e.g., ketals and other latent acid-forming species. Most preferably as to this embodiment, the reaction is conducted in the complete absence of any solvent.

Production of a Vapor Phase

It has been surprisingly discovered that the application of flash vaporization of the reaction complex eliminates or minimizes the formation of undesirable side reaction products and/or unwanted intermediate and product polymer complexes. By comparison, the prior art typically conducted bulk liquid phase reactions for the Knovenagel synthesis of methylene malonates. Such systems have the disadvantage of intimate molecular contact once the methylene malonate forms and before that allows for a multitude of competing reactions to occur based upon the byproducts of the optional acid solvent, the formaldehyde, the product of formaldehyde and water (methylene glycol), the methylene malonate, the created water and any effects of any catalyst system, if present. Even further, the inventors have discovered through NMR studies that methods that utilize a liquid phase Knovenagel reaction do not in fact produce monomer, but rather monomer that almost instantaneously forms a type of oligomeric complex—not likely through the double bond—that must be subsequently "cracked" (i.e., reduced to monomer units) or otherwise reversed. In other words, no exo- or $CH_2$-containing double bonds are detectable following a prior art Knovenagel reaction. It would be preferred to not go through an energy intensive step with prolonged heating times that produces a myriad of potential deleterious products that reduce yields and affect monomer activity and purification methodology.

Without being limited by theory, it is believed that the heat supplied to the cracking step must be sufficient to supply in total four different heat requirements. Firstly, the oligomer mixture must be heated up to a temperature that is hot enough for reaction to occur and also for vaporization of the products to occur. The temperature for vaporization is determined by the pressure that the reaction mixture is at. Secondly, the heat of reaction must be met. Thirdly, any light reaction products must be vaporized. Fourthly heat must be supplied so that the product itself can be vaporized from the liquid phase into the vapor phase. The vaporization of the product is affected by the system pressure also.

At any given location in the cracking reactor, heat must be supplied fast enough so that all four heat load requirements can be met fast enough such that the product itself does not suffer adverse reactions in the liquid phase that lead to impurities that affect the performance of the final product.

Thus one embodiment of the invention provides a process wherein the rate of supply of heat is sufficient to vaporize the product prior to adverse reactions occurring in the liquid phase.

Furthermore, the pressure should not be too high, such that temperature is too high, and the rate of adverse side reactions is faster due to the higher temperature, but the vaporization is limited by mass transfer constraints. In certain types of equipment, there will be a liquid film with a finite residence time. For example, we have shown that a residence time of 20 to 40 seconds with a liquid film can be used to produce product.

Additionally, it must be noted that there can be a difference between the heat transfer medium temperature and the temperature in the regions in the reactive zone or reactive film. In this case, the heat transfer medium may be for example hot oil, and heat travels through the wall of the vessel to the liquid film. The liquid may be mixed or stirred or wiped to generate a thin film in some cases. Depending on the wiping mixing or stirring rate, and the rate of formation of the product and the rate of evaporation of product and light species, the temperature in the film and different regions of the film will be slightly less than that in the heat transfer medium. This is the case of the reaction mixture in indirect contact with the heat transfer medium. The heat transfer medium may be steam, hot oil, pressurized hot water, or other medium retained in a heat exchanger or behind some other heat transfer surface.

In other cases, the heat transfer medium is at the same temperate as the reaction mixture, for example when a hot gas or a hot liquid is used that is heated by the heat transfer medium, and the reaction mixture is in direct contact. This is the case of direct contact with the heat transfer medium.

As such, in this aspect of the invention, flash vaporization, superheat vaporization or any other suitable high-temperature distillation process can be utilized to effectively eliminate or minimize the formation of undesirable polymer complex intermediates and/or products and other deleterious side products. Flash vaporization involves using high temperatures—typically above the boiling point of the methylene malonate at atmospheric pressures or under vacuum—to prevent and minimize such side reactions and/or the formation of such polymer complexes. Specifically, the effect of flash vaporization is to prevent the intimate contact required to accelerate these side reactions and polymer complex formations by simultaneous distillation and condensing of the final products to an ambient temperature or any temperature at which the materials do not react. In one aspect, as in any aspect of vaporization, the reaction product fractions can be isolated and condensed into a stabilized system that inhibits the polymerization and degradation of the monomer product, such as, an acid stabilizer.

To conduct the flash vaporization technique of the invention, the reaction can be conducted in a first reaction vessel. Specifically, the technique may proceed by:

(a) reacting a malonic acid ester with a source of formaldehyde; optionally in the presence of an acidic or basic catalyst; and optionally in the presence of an acidic or non-acidic solvent, to form a reaction complex; and (b) contacting the reaction complex or a portion thereof with an energy transfer means to produce a vapor phase comprising methylene malonate monomer; and (c) isolating the methylene malonate monomer from the vapor phase.

Immediately upon completion of the reaction, e.g., at regular intervals or the like, the reaction complex or a portion thereof is transferred into a flash distillation chamber or another vessel that contains an energy transfer means.

In certain embodiments the reaction complex or a discrete portion thereof is substantially vaporized in less than 15 minutes; less than 10 minutes; less than 1 minute; less than 30 seconds; less than 10 seconds; or less than 1 second of after contact with the energy transfer means. In general, the reaction complex or a portion thereof is substantially vaporized prior to the formation of latent acid forming impurities or irreversible complex impurities.

When discrete portions of the reaction complex are vaporized separately, each portion of reaction complex is substantially vaporized prior to contacting of another portion of reaction complex with the energy transfer means. The contacting and isolating steps can be repeated on discrete portions of the reaction mixture until all of the reaction mixture has been vaporized. In other instances, portions of the reaction mixture can be stored for later use as a heat transfer agent. This process can be run as a batch reaction or as a continuous reaction, in both cases with a continuous flow of ingredients. Surprisingly, the primary product produced via this approach is methylene malonate with the remainder typically unreacted formaldehyde and malonate, both of which can be recovered and recycled.

The energy transfer means is generally a means or an element which is capable of volatilizing a reaction complex, usually by, but not limited to, rapidly heating the reaction complex to temperatures from about 150° C. to about 300° C. Such energy transfer means include, but are not limited to, heat transfer agents, heat transfer surfaces, lasers, and sources of radiation.

In certain embodiments, the energy transfer means is a heat transfer agent.

In other embodiments, the energy transfer means is a heat exchanger.

In still other embodiments, the energy transfer means is a laser.

In yet other embodiments, the energy transfer means is a source of radiation. In particular embodiments, the radiation is microwave radiation.

The energy transfer means utilized rapidly heats the reaction complex, vaporizing the components and sending them through the condenser to be condensed or otherwise isolated Any heat transfer agent which will not result in the production of deleterious side products may be used as will be known by one of skill in the art. In certain embodiments of the invention wherein a heat transfer agent is utilized, the heat transfer agent is one or more metal beads, one or more glass beads, one or more porcelain beads, silica, silicone oil, mineral oil, a petroleum based heat transfer oil or a synthetic chemical based heat transfer oil. In certain embodiments the heat transfer agent is a heated inert gas or a pre-formed portion of reaction complex.

Any heat exchanger which will not result in the production of deleterious side products may be used as will be known by one of skill in the art. In another embodiment of the invention wherein a heat exchanger is used, the heat exchanger is a shell and tube heat exchanger, a plate heat exchanger, and adiabatic wheel heat exchanger, a finned pipe heat exchanger, a plate fin heat exchanger, or a scraped surface heat exchanger.

Any laser or source of radiation which will not result in the production of deleterious side products may be used as will be known by one of skill in the art. In particular embodiments, microwave radiation is utilized though X-ray radiation, gamma ray radiation or beta radiation may be utilized.

A variation of the flash vaporization, referred to herein as the superheat vaporization reaction, is also contemplated whereby the heat transfer media is contained within the reaction mixture. Specifically, the technique may proceed by:

(a) reacting a malonic acid ester with a source of formaldehyde in the presence of heat transfer agent; optionally in the presence of an acidic or basic catalyst; and optionally in the presence of an acidic or non-acidic solvent, to form a reaction complex; and (b) producing a vapor phase comprising methylene malonate monomer from the reaction complex by heating the reaction complex to between about 150° C. and about 300° C.; and (c) isolating the methylene malonate monomer from the vapor phase.

Once the reaction has been allowed to proceed and at least some of the reaction complex has formed, the reaction mixture is heated. Due to the presence of the heat transfer media, the heat transfer media facilitates rapid transfer of heat to the reaction complex, thereby vaporizing the components and sending them through the condenser to be condensed. This process could be run as a batch reaction or as a continuous reaction, in both cases with a continuous flow of ingredients. Surprisingly, the primary product produced via this approach is methylene malonate with the remainder typically unreacted formaldehyde and malonate, both of which can be recovered and recycled.

In certain embodiments of the superheat vaporization, the heat transfer agent is one or more metal beads, one or more glass beads, one or more porcelain beads, silica, silicone oil, mineral oil, a petroleum based heat transfer oil or a synthetic chemical based heat transfer oil. In certain embodiments the heat transfer agent is a heated inert gas or a pre-formed portion of reaction complex.

Recovery

The present invention contemplates any suitable method for recovery of the methylene malonate products from the vapor phase. In certain embodiments of the present invention, the recovery method involves one or more rounds of simple distillation of a condensed vapor phase. In certain other embodiments, the recovery method involves one or more rounds of a rapid distillation of a condensed vapor phase method, e.g., flash distillation or superheat distillation. In still other embodiments, the recovery method involves liquid chromatographic separation of methylene malonate products from a condensed vapor phase. In yet other embodiments, the recovery method involves gas chromatographic separation of vaporized methylene malonate products directly from the vapor phase.

Those having ordinary skill in the art will appreciate that simple distillation methods are well known. Simple distillation is a widely used method for separating the components of a liquid mixture, e.g., reaction mixture of the present invention, and depends upon the differences in the ease of vaporization of the components, i.e., typically, the most volatile components of the liquid mixture will vaporize at the lowest temperature, whereas the least volatile components will vaporize at higher temperatures. The vaporized components pass through a cooled tube or condenser causing the components to condense back into their liquid states and deposit in a collector or equivalent vessel. By separating the distillated into sequentially collected fractions ranging from most volatile to least volatile components, the components can be separated. The process can be repeated on any given fraction(s) to further separate the components.

However, as the composition of the liquid to be separated becomes more complex, the greater will be the difficulty in separating out the different volatile components therein, particularly where there is significant overlap in components having similar volatility characteristics. For instance, in the present invention, the methylene malonate products may have similar volatility characteristics as certain side products that may form, e.g., ketals, which increases the difficulty in separating those particular components.

The present invention also contemplates any scale distillation process, including laboratory scale distillation and industrial distillation processes. The main difference between laboratory scale distillation and industrial distillation is that laboratory scale distillation is often performed batch-wise, whereas industrial distillation often occurs continuously. In batch distillation, the composition of the source material, the vapors of the distilling compounds and the distillate change during the distillation. In batch distillation, a still is charged (supplied) with a batch of feed mixture (e.g., reaction mixture of the present invention), which is then separated into its component fractions which are collected sequentially from most volatile to less volatile, with the bottoms (remaining least or non-volatile fraction) removed at the end. The still can then be recharged and the process repeated. In continuous distillation, the source materials, vapors, and distillate are kept at a constant composition by carefully replenishing the source material and removing fractions from both vapor and liquid in the system. This results in a better control of the separation process. All of these methods are contemplated by the present invention.

The invention further contemplates any known improvements or modifications to simple distillation processes, including improvements to both batch and continuous distillations. For example, one improvement can include making use of a fractionating column on top of the distillation flask. The column improves separation by providing a larger surface area for the vapor and condensate to come into contact. This helps it remain at equilibrium for as long as possible. The column can even consist of small subsystems ("trays" or "dishes") which all contain an enriched, boiling liquid mixture, all with their own vapor-liquid equilibrium.

There are differences between laboratory-scale and industrial-scale fractionating columns, but the principles are the same. Examples of laboratory-scale fractionating columns (in increasing efficiency) include, for example, air condenser, Vigreux column (usually laboratory scale only); packed column (packed with glass beads, metal pieces, or other chemically inert material); and spinning band distillation systems.

Further details regarding distillation processes contemplated by the present invention are as follows.

In simple distillation, the hot vapors produced are immediately channeled into a condenser that cools and condenses the vapors. Therefore, the distillate may not be pure—its composition will be identical to the composition of the vapors at the given temperature and pressure, and can be computed from Raoult's law.

As a result, simple distillation is usually used only to separate liquids whose boiling points differ greatly (e.g., by 25° C.), or to separate liquids from non-volatile solids or oils. For these cases, the vapor pressures of the components are usually sufficiently different that Raoult's law may be neglected due to the insignificant contribution of the less volatile component. In this case, the distillate may be sufficiently pure for its intended purpose. Keeping the above in mind, one of ordinary skill in the art will have sufficient knowledge and understanding as to utilize simple distillation where advantageous and/or desirous in the present invention as a means of separating the methylene malonate products from the reaction mixture.

Another type of general distillation method includes fractional distillation and is contemplated by the present invention. It will be appreciated that in certain situations where the boiling points of certain components in the mixture are sufficiently close to one another that Raoult's law must be taken into consideration. Therefore, fractional distillation must be used in order to sufficiently separate the components by repeated vaporization-condensation cycles within a packed fractionating column. This separation, by successive distillations, is also referred to as rectification.

As the liquid mixture to be purified (e.g., the reaction mixture of the present invention) is heated, its vapors rise into the fractionating column. As it rises, it cools, condensing on the condenser walls and the surfaces of the packing material. Here, the condensate continues to be heated by the rising hot vapors causing it to vaporize once again. However, the composition of the fresh vapors are determined once again by Raoult's law. Each vaporization-condensation cycle (called a theoretical plate) will yield a purer solution of the more volatile component. In actual operation, each cycle at a given temperature does not occur at exactly the same position in the fractionating column. Thus, it will be appreciated that the theoretical plate is thus a concept rather than an accurate description. More theoretical plates lead to better separations. A spinning band distillation system uses a spinning band of Teflon or metal to force the rising vapors into close contact with the descending condensate, thereby increasing the number of theoretical plates.

Another type of distillation method contemplated by the present invention includes vacuum distillation. Some compounds have very high boiling points. To boil such compounds, it may be advantageous to lower the pressure at which such compounds are boiled instead of increasing the temperature. Once the pressure is lowered to the vapor pressure of the compound at the given temperature, boiling and the rest of the distillation process can commence. This technique is referred to as vacuum distillation and it is commonly found in the laboratory in the form of the rotary evaporator. This technique is also very useful for compounds which boil beyond their decomposition temperature at atmospheric pressure and which would therefore be decomposed by any attempt to boil them under atmospheric pressure. One of ordinary skill in the art will have the knowledge and understanding to apply vacuum distillation techniques when advantageous and/or where appropriate to recover the methylene malonate monomer products of the reaction.

In yet another distillation technique, named short path distillation, is a distillation technique that involves the distillate travelling a short distance, often only a few centimeters, and is normally done at reduced pressure. A typical example would be a distillation involving the distillate travelling from one glass bulb to another, without the need for a condenser separating the two chambers. This technique is often used for compounds which are unstable at high temperatures or to purify small amounts of compound. The advantage is that the heating temperature can be considerably lower (at reduced pressure) than the boiling point of the liquid at standard pressure, and the distillate only has to travel a short distance before condensing. A short path ensures that little compound is lost on the sides of the apparatus. The Kugelrohr is a kind of a short path distillation apparatus which often contain multiple chambers to collect distillate fractions. One of ordinary skill in the art will have the knowledge and understanding to apply short path distillation techniques when advantageous and/or where appropriate to recover the methylene malonate monomer products of the reaction.

Other types of known distillation techniques are also contemplated by the present invention, including, for example, the process of reactive distillation. This type of distillation involves using the reaction vessel as the still. In this process, the product is usually significantly lower-boiling than its reactants. As the product is formed from the reactants, it is vaporized and removed from the reaction mixture. This technique is an example of a continuous vs. a batch process; advantages include less downtime to charge the reaction vessel with starting material, and less workup. In addition, the method of pervaporation may be used. This method is for the separation of mixtures of liquids by partial vaporization through a non-porous membrane. Still further, the invention contemplates extractive distillation methods, which are defined as distillations that occur in the presence of a miscible, high boiling, relatively non-volatile component, i.e., the solvent, that forms no azeotrope with the other components in the mixture.

The present invention also contemplates the industrial-scale synthesis of the methylene malonates of the present invention, which can include any suitable scaled-up industrial distillation procedure and/or technology. Such technologies and methods are generally well-known in the art and can be applied and utilized to separate out the methylene malonates of the present invention by those having ordinary skill in the art without an undue amount of experimentation. Large scale industrial distillation applications can include both batch and continuous fractional, vacuum, azeotropic, extractive, and steam distillation methods.

Industrial distillation is typically performed in large, vertical cylindrical columns known as distillation towers or distillation columns with diameters ranging from about 65 centimeters to 16 meters and heights ranging from about 6 meters to 90 meters or more. When the process feed (e.g., a methylene malonate reaction mixture of the invention) has a diverse composition, as in distilling crude oil, liquid outlets at intervals up the column allow for the withdrawal of different fractions or products having different boiling points or boiling ranges. The "lightest" products (those with the lowest boiling point) exit from the top of the columns and the "heaviest" products (those with the highest boiling point) exit from the bottom of the column. One of ordinary skill in the art will have the knowledge and understanding to apply such industrial distillation techniques when advantageous and/or where appropriate to recover the methylene malonate monomer products of the reaction of the invention.

In one preferred embodiment, the present invention contemplates utilizing the technique referred to as flash distillation in the separation of methylene malonate products from the reaction mixture of the invention. It will be appreciated that distillation is a widely used industrial method for separating liquid mixtures and is at the heart of the separation processes in many chemical processes. The most elementary form of the method is simple distillation—as discussed above—in which the liquid is brought to boiling and the vapor formed is separated and condensed to form a product.

The inventors have surprisingly found that the redistillation following the isolation of methylene malonate product from the vapor phase facilitates the elimination or minimization of the unwanted deleterious side products and the formation of undesirable polymer complexes that impinge on the overall quality and reactivity of the methylene malonate monomers.

It is further contemplated that monomer obtained by the methods of the invention may be further redistilled at least once, twice, or thrice or more additional times to further fractionate the methylene malonate monomer product. Preferably, these redistillations should be conducted very quickly following the flash or superheat distillation process, preferably no more than about 24 hours, about 12 hours, about 4 hours, about 2 hours, about 60 minutes, about 45 minutes, about 30 minutes, about 10 minutes, or about 1 minute after production. More preferably, the follow-on distillations occur no more than about 60 minutes after the initial flash or superheat distillation method. The inventors have surprisingly found that the redistillation following the recovery facilitates the elimination or minimization of the unwanted deleterious side products and the formation of undesirable polymer complexes that impinge on the overall quality and reactivity of the methylene malonate monomers.

Yet another type of suitable recovery method can be by sublimation. Some monomers can pass directly from the solid to the gaseous stage without first melting and becoming liquid. These substances are said to be able to sublimate. Substances that sublimate, when mixed with substances that do not sublimate, can be separated by heating the mixture until the substance that can sublime is completely gone. In sublimation, a solid compound evaporates directly to the gas phase without becoming a liquid. In vacuum sublimation, the sample is placed under reduced pressure which permits sublimation at lower temperatures (which can mean less decomposition in a sample). In purification by sublimation, a solid compound is heated and evaporates. The vapors condense on a cold surface to form new crystals. Sublimation can be a suitable means in the present invention to purify samples of methylene malonate monomers, and in particular, those that are first crystallized to a solid. Methods for separation and recovery by sublimation are well-known in the art. A resource for carrying out sublimation recovery can be found, for example, in *Crystallization*, Publ. Butterworth-Heinemann, 2001, By John William Mullin, Chapter 8.3.2, page 363, the relevant contents of which are incorporated herein by reference.

Recrystallization is another suitable means for recovering the monomers of the invention. The general principle is that certain monomer and any impurities therein may be dissolved in a solvent and then cooled to produce a fresh crop of purer crystals of methylene malonate monomers, provided that the impurities are more soluble in the solvent than the main product. This process may be repeated a multitude of times until a pure crystal of the main product may be obtained. The techniques of recrystallization will be well-known in the art, but further details may be found in *Crystallization*, Publ. Butterworth-Heinemann, 2001, By John William Mullin, Chapter 7.1, page 289, the relevant contents of which are incorporated herein by reference.

Any of the recovery techniques described herein may be conducted in isolation or in any combination where suitable.

As mentioned, distillation methods are well-known in the art. Further exemplary methods of distillation contemplated by the present invention, including simple distillation methods, batch and industrial distillation processes, and flash and superheat distillation methods, as well as other mentioned above, can be found, for example, in U.S. Pat. No. 7,771,567 (Salt water distillation system); U.S. Pat. No. 7,649,108 (Process for the distillation of a mixture of isomeric diisocyanatodiphenylmethanes); U.S. Pat. No. 7,610,775 (Distillation process using microchannel technology); U.S. Pat. No. 7,603,889 (System for monitoring and controlling unit operations that include distillation); U.S. Pat. No. 7,305,850 (Distillation process using microchannel technology); U.S. Pat. No. 6,936,140 (Water distillation system); U.S. Pat. No. 6,841,064 (Process for the gentle flash distillation of residual oils); U.S. Pat. No. 6,716,355 (Method for the purification of a liquid by membrane distillation, in particular for the production of desalinated water from seawater or brackish water or process water); U.S. Pat. No. 6,413,415 (Method for high-temperature short-time distillation of residual oils); U.S. Pat. No. 6,291,703 (Preparation of substituted hydroxyhydrocinnamate esters by continuous transesterification using reactive distillation); U.S. Pat. No. 5,284,987 (Preparation of a dimethyltetralin in a distillation reactor); U.S. Pat. No. 5,227,027 (High efficiency water distillation apparatus using a heat pump system and process for use thereof); U.S. Pat. No. 5,064,507 (Distillation process for recovery of high purity phenol); U.S. Pat. No. 4,783,242 (Distillation system and process); U.S. Pat. No. 4,767,503 (Removal of light impurities from caprolactam by distillation with water); H214 (Distillation process for the isolation of 1,1-difluoro(mono- or dihalo) ethoxy-benzeneamines); U.S. Pat. No. 4,584,064 (Device and installations for the distillation by thin layer evaporation particularly of hydrocarbons, and process for operating this device); U.S. Pat. No. 4,450,067 (Distillation-induced extraction process); U.S. Pat. No. 4,440,601 (Method and apparatus for high volume fractional distillation of liquids); U.S. Pat. No. 4,411,740 (Separation of chlorosilanes by extractive distillation); U.S. Pat. No. 4,319,964 (Apparatus for high volume distillation of liquids); U.S. Pat. No. 4,282,071 (Anhydrous separation of volatile aluminum chloride complex from an ethylbenzene production stream by distillation); U.S. Pat. No. 4,282,067 (Apparatus for high volume distillation of liquids); U.S. Pat. No. 4,243,493 (Process for transportation and distillation of petroleum with methanol); U.S. Pat. No. 4,236,975 (Recovery of methyl heptafluorobutyrate from water by distillation); U.S. Pat. No. 4,229,263 (Recovery of methyl heptafluorobutyrate from methanol by distillation); U.S. Pat. No. 4,224,112 (Recovery of 1,1-dihydroheptafluorobutanol from water by distillation); U.S. Pat. No. 4,186,060 (Method and apparatus for high volume distillation of liquids); U.S. Pat. No. 4,186,058 (Method and apparatus for high volume distillation of liquids); U.S. Pat. No. 4,176,012 (Adjacent loop distillation); U.S. Pat. No. 4,148,693 (Horizontal cylindrical distillation apparatus); U.S. Pat. No. 4,140,584 (Distillation plant); U.S. Pat. No. 4,035,243 (Method and apparatus for high volume distillation of liquids); U.S. Pat. No. 4,018,656 (Thermal softening and distillation by regenerative method); U.S. Pat. No. 4,004,984 (Distillation plant); U.S. Pat. No. 4,001,345 (Distillation of methylchloroform); U.S. Pat. No. 3,966,562 (Multi-stage flash distillation plant); U.S. Pat. No. 3,945,891 (Distillation process for purification of triaryl phosphate esters), each of the above of which are incorporated in their entireties by reference herein.

Compositions

The methylene malonate monomers of the invention can be incorporated into any number of compositions and products including but not limited to monomer-based compositions, oligomer-based compositions and polymer based compositions.

In certain embodiments, the invention provides a composition comprising a methylene malonate monomer which is substantially free of acetic acid.

In other embodiments, the invention provides a composition comprising a methylene malonate monomer having specific functional properties without the addition of a stabilizer or other preservative compound.

For example, the compositions of the invention can be analyzed by placing a drop of a monomer composition on a substrate (for example a glass slide or 4"×1" polycarbonate sample). Another glass slide or piece of polycarbonate is pressed on top over the monomer-covered area. The time is then immediately recorded from pressing the top-slide till the two slides are bonded tightly. In such embodiments, said composition of the invention is capable of bonding glass to a substrate in less than about 90 seconds, less than about 60 seconds, less than about 30 seconds or less than about 15 seconds. Similarly, said composition of the invention is capable of bonding polycarbonate to a substrate in less than about 90 seconds, less than about 60 seconds, less than about 45 seconds or less than about 30 seconds.

Alternatively, the compositions of the invention can be analyzed by mixing 0.5 ml of monomer with 0.3 ml of 3% tertiary butyl ammonium fluoride (TBAF) in Dibutyl Phthalate solution. The time is recorded from adding the TBAF solution till the mixture become solid with vigorous stirring or mixing. In such embodiments, said composition solidifies upon addition of 3% tertiary butyl ammonium fluoride (TBAF) in Dibutyl Phthalate solution in less than about 15 seconds, less than about 10 seconds, or less than about 7 seconds.

Alternatively still, the compositions can be analyzed by placing 0.5 ml of monomer into a test tube and cap with a cork stopper and keeping the test tubes containing monomers at 25° C., or in ovens at 55° C. or 82° C. In each case the storage stability test is performed at atmospheric pressure. Time is recorded when the monomer became a gel or solid. In such embodiments, said composition remains stable at 25° C. and at atmospheric pressure for more than 10 days, more than 15 days, more than 20 days, more than 25 days or more than 30 days. Similarly, said composition remains stable at 82° C. and at atmospheric pressure for more than about 2 hours, more than about 3 hours, or more than about 4 hours.

Such monomer-based and oligomer-based compositions include, but are not limited to an adhesive, a coating, a sealant, a composite, or a surfactant.

Such polymer-based compositions include, but are not limited to, a sealant, a thermal barrier coating, a textile fiber, a water-treatment polymer, an ink carrier, a paint carrier, a packaging film, a molding, a medical polymer, a polymer film, a polymer fiber or a polymer sheet.

In each case, the compositions of the invention may be formulated to include one or more materials to extend the shelf-life as well as control the onset of cure of the materials. In certain embodiments, the compositions are formulated such that the composition is stable for at least 1 month, or for at least 2 months, or for at least 3 months, or for at least 4 months, or for at least 5 months, or for at least 5-10 months, or for at least 10-20 months, or for at least 20-30 months. Preferably, the adhesive composition comprising the methylene malonate monomers of the invention, or other commercial compositions or products, are stable for at least one year.

Such formulation materials include acidic stabilizer, volatile acid stabilizers, acidic gases, free radical stabilizers, sequestering agents, cure accelerators and rheology modifiers.

The present invention contemplates any suitable acidic stabilizer known in the art, including, for example, trifluoromethane sulfonic acid, maleic acid, methane sulfonic acid, difluoro acetic acid, trichloroacetic acid, phosphoric acid, dichloroacetic acid, chlorodifluoro or like acid. Acidic stabilizers can include any material which can be added to the monomer or polymer compositions to extend shelf-life, e.g., by up to, for example, 1 year or more. Such acidic stabilizers may have a pKa in the range of, for example, between about −15 to about 5, or between about −15 to about 3, or between about −15 to about 1, or between −2 to about between about −2 to about 2, or between about 2 to about 5, or between about 3 to about 5.

Volatile acid stabilizers include any material which can be added to the monomer or polymer compositions to extend shelf-life and stabilize the vapor phase above the composition upon storage, e.g., acidic gases. Such volatile acid stabilizers may have a boiling point, for example, less than about 200° C.; less than about 170° C.; or less than about 130° C.

Acidic gases include any gaseous material which can be added to the monomer or polymer compositions to extend shelf-life and stabilize the vapor phase above the composition upon storage. Such acid gases can include, but are not limited to, $SO_2$ or $BF_3$.

For each of these acidic stabilizing materials, such acidic stabilizer can be present in a concentration of about 0.1 ppm to about 100 ppm; about 0.1 ppm to about 25 ppm; or about 0.1 ppm to about 15 ppm.

Free radical stabilizers can include any material capable of stabilizing or inhibiting free radical polymerization of the material upon standing. In one embodiment, the free radical stabilizers are phenolic free radical stabilizers such as, HQ (hydroquinone), MEHQ (methyl-hydroquinone), BHT (butylated hydroxtoluene) and BHA (butylated hydroxyanisole). In certain embodiments, the free radical stabilizers are present in a concentration of 0.1 ppm to 10,000 ppm; 0.1 ppm to 3000 ppm; or 0.1 ppm to 1500 ppm. In certain other embodiments, particularly where a free radical or ultraviolet cure will be utilized on the materials of the invention, the free radical stabilizers are present in a concentration of 0.1 ppm to 1000 ppm; 0.1 ppm to 300 ppm; or 0.1 ppm to 150 ppm.

Sequestering agents include any material capable of enhancing the bonding of materials containing acid salts such as paper or wood. Such sequestering agents include, but are not limited to crown ethers, silyl crowns, calixarenes and polyethylene glycols. Sequestering agents also enhance the utility of surface accelerators that are acid salts applied to surfaces to control the rate of cure of the materials.

Cure accelerators include any material capable of speeding the rate of cure of the methylene malonate monomers of the invention. Cure accelerators also include any material capable of speeding the cure through volume of the methylene malonate monomers of the invention. Such cure accelerators include but are not limited to sodium or potassium acetate; acrylic, maleic or other acid salts of sodium, potassium lithium copper and cobalt; salts such as tetrabutyl ammonium fluoride, chloride, or hydroxide; or chemically basic materials such as amines and amides, or salts of polymer bond acids, benzoate salts, 2,4-pentanedionate salts, sorbate salts, or propionate salts. Such cure accelerators can be added directly to the compositions of the invention or applied to the material to be bonded prior to addition of the composition of the invention.

Rheology modifiers include any material which can modify the viscosity of the compositions of the invention as well as thixotropic properties for greater utility in certain applications. Rheology modifiers include, but are not limited to, hydroxyethylcellulose, ethyl hydroxyethylcellulose, methylcellulose, polymeric thickeners, pyrogenic silica or a combination thereof.

In certain embodiments, the compositions of the invention may include tougheners. Such tougheners include, but are not limited to, acrylic rubbers; polyester urethanes; ethylene-vinyl acetates; fluorinated rubbers; isoprene-acrylonitrile polymers; chlorosulfonated polyethylenes; homopolymers of polyvinyl acetate; and reaction products of the combination of ethylene, methyl acrylate and monomers having carboxylic acid cure sites, which once formed are then substantially free of processing aids and anti-oxidants; and combinations thereof. In certain embodiments, the tougheners include those disclosed in U.S. Pat. No. 4,440,910 (O'Connor), directed to rubber toughened cyanoacrylate compositions through the use of certain organic polymers as toughening additives that are elastomeric, i.e., rubbery, in nature, such as acrylic rubbers; polyester urethanes; ethylene-vinyl acetates; fluorinated rubbers; isoprene-acrylonitrile polymers; chlorosulfonated polyethylenes; and homopolymers of polyvinyl acetate. In certain embodiments, the toughener is an elastomeric polymer which is a copolymer of methyl acrylate and ethylene, manufactured by DuPont, under the name of VAMAC, such as VAMAC N123 and VAMAC B-124. VAMAC N123 and VAMAC B-124 are reported by DuPont to be a master batch of ethylene/acrylic elastomer. In other embodiments, the toughener may be the DuPont materials called VAMAC B-124, N123, VAMAC G, VAMAC VMX 1012 or VCD 6200. In other instances, the toughener may be a rubber toughening component having (a) reaction products of the combination of ethylene, methyl acrylate and monomers having carboxylic acid cure sites, (b) dipolymers of ethylene and methyl acrylate, and combinations of (a) and (b), which once the reaction products and/or dipolymers are formed are then substantially free of processing aids, such as the release agents octadecyl amine (reported by DuPont to be available commercially from Akzo Nobel under the tradename ARMEEN 18D), complex organic phosphate esters (reported by DuPont to be available commercially from R.T. Vanderbilt Co., Inc. under the tradename VANFRE VAM), stearic acid and/or polyethylene glycol ether wax, and anti-oxidants, such as substituted diphenyl amine (reported by DuPont to be available commercially from Uniroyal Chemical under the tradename NAUGARD 445). Commercial examples of such rubber tougheners include VAMAC VMX 1012 and VCD 6200 rubbers, and these may be used too.

The methylene malonate-containing compositions of the invention may also optionally include other additives, such as plasticizing agents, thixotropic agents, natural or synthetic rubbers, filler agents, and reinforcing agents, etc. Such additives are well known to those skilled in the art.

The methylene malonate-containing compositions of the invention may optionally include at least one plasticizing agent that imparts flexibility to the polymer formed from the methylene malonate monomer. The plasticizing agent preferably contains little or no moisture and should not significantly affect the stability or polymerization of the monomer. Such plasticizers are useful in polymerized compositions to be used in any application in which flexibility of the adhesive or polymer product is desirable.

Examples of suitable plasticizers include, without limitation, acetyl tributyl citrate, dimethyl sebacate, triethyl phosphate, tri(2-ethylhexyl)phosphate, tri(p-cresyl)phosphate, glyceryl triacetate, glyceryl tributyrate, diethyl sebacate, dioctyl adipate, isopropyl myristate, butyl stearate, lauric acid, trioctyl trimellitate, dioctyl glutarate, and mixtures thereof. Preferred plasticizers are tributyl citrate and acetyl tributyl citrate. In embodiments, suitable plasticizers include polymeric plasticizers, such as polyethylene glycol (PEG) esters and capped PEG esters or ethers, polyester glutarates and polyester adipates.

The addition of plasticizing agents in amounts less than about 60 weight %, or less than about 50 weight %, or less than about 30 weight %, or less than about 10 weight %, or less than about 5 weight %, or less than about 1 weight % or less, provides increased film strength (e.g., toughness) of the polymerized monomer over polymerized monomers not having plasticizing agents.

The methylene malonate-containing compositions of the invention may also optionally include at least one thixotropic agent, i.e., the property of exhibiting a high fluidity during deformation by force of a sprayer, roller or trowel, but losing the fluidity when left at rest. Suitable thixotropic agents are known to the skilled artisan and include, but are not limited to, silica gels such as those treated with a silyl isocyanate. Examples of suitable thixotropic agents are disclosed in, for example, U.S. Pat. No. 4,720,513 or 4,510,273, the disclosures of which are hereby incorporated in their entireties.

The methylene malonate-containing compositions of the invention may also optionally include at least one natural or synthetic rubber to impart impact resistance, which is preferable especially for industrial compositions of the present invention. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties.

The methylene malonate-containing compositions of the invention may also optionally comprise one or more other reinforcing agents (e.g., fibrous reinforcements) other than natural or synthetic rubber to impart impact resistance and/or to impart structural strength or to provide shape or form. Examples of such agents are well known in the art. Examples of suitable fibrous reinforcement include PGA microfibrils, collagen microfibrils, cellulosic microfibrils, and olefinic microfibrils. The compositions may also contain colorants such as dyes, pigments, and pigment dyes. Examples of suitable colorants include 6-hydroxy-5-[(4-sulfophenyl)axo]-2-naphthalene-sulfonic acid (FD+C Yellow No. 6); 9-(o-carboxyphenyl)-6-hydroxy-2,4,5,7-tetraiodo-3H-xanthen-3-one monohydrate (FD+C Red No. 3); and 2-(1,3-dihydro-3-oxo-5-sulfo-2H-indol-2-ylidene)-2,3-dihydro-3-oxo-1H-indole-5-sulfonic acid (FD+C Blue No. 2), wherein the suitable colorant should not destabilize the monomer.

The methylene malonate-containing compositions of the invention may also optionally include at least one thickening agent. Suitable thickeners include, for example, polycyanoacrylates, polylactic acid, poly-1,4-dioxa-2-one, polyoxalates, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene. Examples of alkyl methacrylates and acrylates are poly(2-ethylhexyl methacrylate) and poly(2-ethylhexyl acrylate), also poly(butylmethacrylate) and poly(butylacrylate), also copolymers of various acrylate and methacrylate monomers, such as poly(butylmethacrylate-co-methylacrylate).

To improve the cohesive strength of adhesives formed from the methylene malonate-containing compositions of this invention, difunctional monomeric cross-linking agents may be added to the monomer compositions of this invention. Such crosslinking agents are known. U.S. Pat. No. 3,940,362 to Overhults, which is hereby incorporated in its entirety by reference, discloses such crosslinking agents.

Other compositions and additives contemplated by the present invention, including additional stabilizers, accelerators, plasticizers, fillers, opacifiers, inhibitors, thixotropy conferring agents, dyes, fluorescence markers, thermal degradation reducers, adhesion promoters, thermal resistance conferring agents and combinations thereof, and the like, some of which are exemplified by U.S. Pat. Nos. 5,624,669; 5,582,834; 5,575,997; 5,514,371; 5,514,372; 5,312,864 and 5,259,835, the disclosures of all of which are hereby incorporated in their entirety by reference.

Depending on whether the composition is a monomer-based composition (e.g., inks, adhesives, coatings, sealants or reactive molding) or a polymer-based composition (e.g., fibers, films, sheets, medical polymers, composite polymers and surfactants), one having ordinary skill in the art will have the knowledge and skill by which to formulate such compositions and/or products without undue experimentation having suitable amounts, levels and combinations of the above types of additives and components.

Oligomeric Complex Products

The inventors have surprisingly discovered that the reaction of malonic acid esters with a source of formaldehyde results in what is believed to be, without being limited by theory or mechanism, an oligomeric complex. The inventors have further discovered that certain oligomeric complexes are capable of being efficiently vaporized or "cracked" into high purity monomers of methylene malonate by rapid vaporization as described herein.

As such, the invention provides an oligomeric complex prepared by reacting a malonic acid ester with a source of formaldehyde; optionally in the presence of heat transfer agent; optionally in the presence of an acidic or basic catalyst; and optionally in the presence of an acidic or non-acidic solvent.

The invention further provides an oligomeric complex prepared by reacting a malonic acid ester with a source of formaldehyde in a substantial absence of acidic solvent; optionally in the presence of heat transfer agent; optionally in the presence of an acidic or basic catalyst; and optionally in the presence of a non-acidic solvent. In certain embodiments, the substantial absence of acidic solvent represents less than 1.0%, less than 0.5%, less than 0.2% or less than 0.1% by weight acidic solvent as compared to the total composition of the reaction mixture.

In a particular embodiment, the invention provides an oligomeric complex which has a GC/MS profile which shows greater than 80% concentration of a methylene malonate monomer. It is believed that such oligomeric complexes comprise between 2 and 12 units of methylene malonate monomers.

Similarly, the invention provides oligomeric complex having a MALDI-TOF analysis spectrum comprising peaks at: 131, 153, 176, 192, 194, 470, 472, 675, and 758.

In another embodiment, the invention provides oligomeric complex having a proton NMR spectrum in $CDCl_3$ at 400 MHz: comprising the following peaks: a singlet at 4.66 ppm and narrow peaks located between 4.32-3.8 ppm.

In still another embodiment, the invention provides an oligomeric complex having the following physiochemical properties:
1.) a GC/MS profile which shows greater than 80% concentration of a methylene malonate monomer;
2.) a MALDI-TOF analysis spectrum comprising peaks at: 131, 153, 176, 192, 194, 470, 472, 675, and 758; and
3.) a proton NMR spectrum in $CDCl_3$ at 400 MHz comprising the following peaks: a singlet at 4.66 ppm and narrow peaks located between 4.32-3.8 ppm.

In a specific aspect, the invention provides oligomeric complex prepared by reacting a malonic acid ester with a source of formaldehyde; optionally in the presence of heat transfer agent; optionally in the presence of an acidic or basic catalyst; and optionally in the presence of an acidic or non-acidic solvent and having one or more of the following physiochemical properties:
1.) a GC/MS profile which shows greater than 80% concentration of a methylene malonate monomer;
2.) a MALDI-TOF analysis spectrum comprising peaks at: 131, 153, 176, 192, 194, 470, 472, 675, and 758; or
3.) a proton NMR spectrum in $CDCl_3$ at 400 MHz: comprising the following peaks: a singlet at 4.66 ppm and narrow peaks located between 4.32-3.8 ppm.

In another specific aspect, the invention provides oligomeric complex prepared by reacting a malonic acid ester with a source of formaldehyde; optionally in the presence of heat transfer agent; optionally in the presence of an acidic or basic catalyst; and optionally in the presence of an acidic or non-acidic solvent and having the following physiochemical properties:
1.) a GC/MS profile which shows greater than 80% concentration of a methylene malonate monomer;
2.) a MALDI-TOF analysis spectrum comprising peaks at: 131, 153, 176, 192, 194, 470, 472, 675, and 758; and
3.) a proton NMR spectrum in $CDCl_3$ at 400 MHz: comprising the following peaks: a singlet at 4.66 ppm and narrow peaks located between 4.32-3.8 ppm.

In each case, the oligomeric complex of the invention results in a weight loss of less than 20% below 218° C. as measured by thermogravimetric analysis.

EXAMPLES

The structures, materials, compositions, and methods described herein are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

The following examples illustrate various exemplary embodiments of the methods described in this disclosure.

Analytical Methods

The structures of monomers of this invention were confirmed using one or more of the following procedures.

NMR

Routine one-dimensional NMR spectroscopy was performed on either a 400 MHz Varian® spectrometer or a 400

MHz Bruker® spectrometer. The samples were dissolved in deuterated solvents. Chemical shifts were recorded on the ppm scale and were referenced to the appropriate solvent signals, such as 2.49 ppm for DMSO-d6, 1.93 ppm for CD3CN, 3.30 ppm for CD3OD, 5.32 ppm for CD2Cl2 and 7.26 ppm for $CDCl_3$ for 1H spectra.

GC/MS

Electron impact mass spectra (EI-MS) were obtained with a Hewlett Packard 5970 mass spectrometer equipped Hewlett Packard 5890 Gas Chromatograph with. The ion source was maintained at 270° C.

Abbreviations and Acronyms

A comprehensive list of the abbreviations used by organic chemists of ordinary skill in the art appears in The ACS Style Guide (third edition) or the Guidelines for Authors for the Journal of Organic Chemistry. The abbreviations contained in said lists, and all abbreviations utilized by organic chemists of ordinary skill in the art are hereby incorporated by reference. For purposes of this invention, the chemical elements are identified in accordance with the Periodic Table of the Elements, CAS version, Handbook of Chemistry and Physics, 67th Ed., 1986-87.

More specifically, when the following abbreviations are used throughout this disclosure, they have the following meanings.

atm atmosphere
br s broad singlet
C Celsius
d doublet
dd doublet of doublets
MM methylene malonate
HQ hydroquinone
GC-MS Gas Chromatography-Mass Spectroscopy
g gram
h hour, hours
$^1$H NMR proton nuclear magnetic resonance
J coupling constant (NMR spectroscopy)
L liter
M mol·$L^{-1}$ (molar)
m multiplet
MHz megahertz
min minute, minutes
mL milliliter
mM millimolar
mol mole
MS mass spectrum, mass spectroscopy
m/z mass-to-charge ratio
N equivalents·$L^{-1}$ (normal)
NMR Nuclear Magnetic Resonance
pH negative logarithm of hydrogen ion concentration
q quartet
rt room temperature
s singlet
t triplet
RB, RBF round bottom flask Example 1

Addition to Energy Transfer Means with Catalyst

In a one-liter 3-neck round bottom flask (equipped with a condenser), 160 g diethyl malonate (1 mol), 60 g of paraformaldehyde (2 mol), 15 g silica and 2 g of zinc acetate dihydrate were heated to 110 C. The reaction exotherms to 130° C. and then was cooled to 60° C.

The resulting mixture was flash vaporized by slow addition to mineral oil (20 g) at 215° C. under a slow sweep of nitrogen. Distillation receiver was cooled to 0° C.

The distillate (crude monomer) was dried with sodium sulfate (5 g) and was stabilized with 1000 ppm sulfuric acid and hydroquinone. Yield=132 g for a 76% yield.

Figure 5:
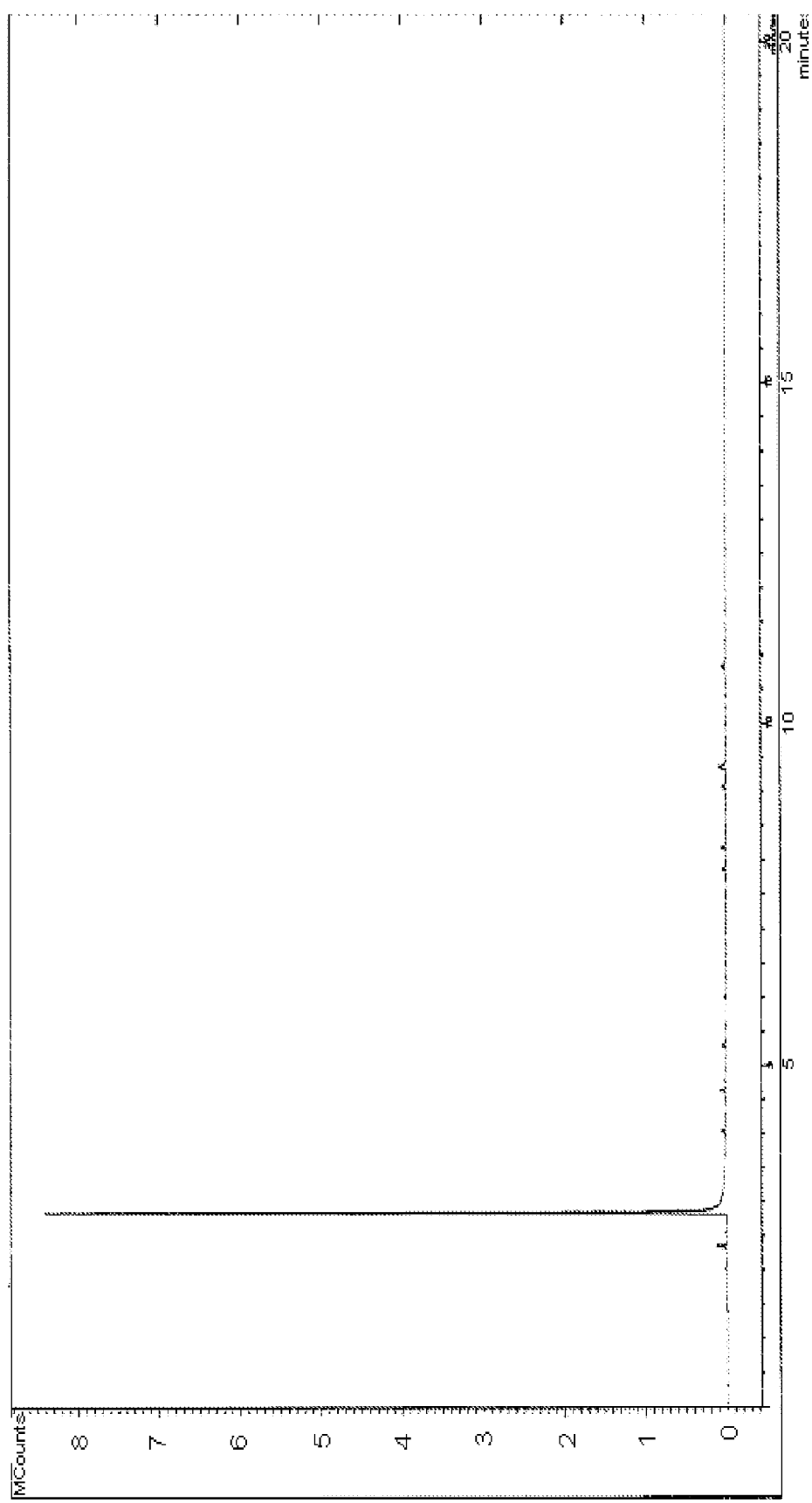
FIG. 5 depicts a GC-MS spectrum of crude Diethylmethylene Malonate produced by flash distillation method using 1 M % Zn(OAc)₂ Dihydrate.
Figure 6:
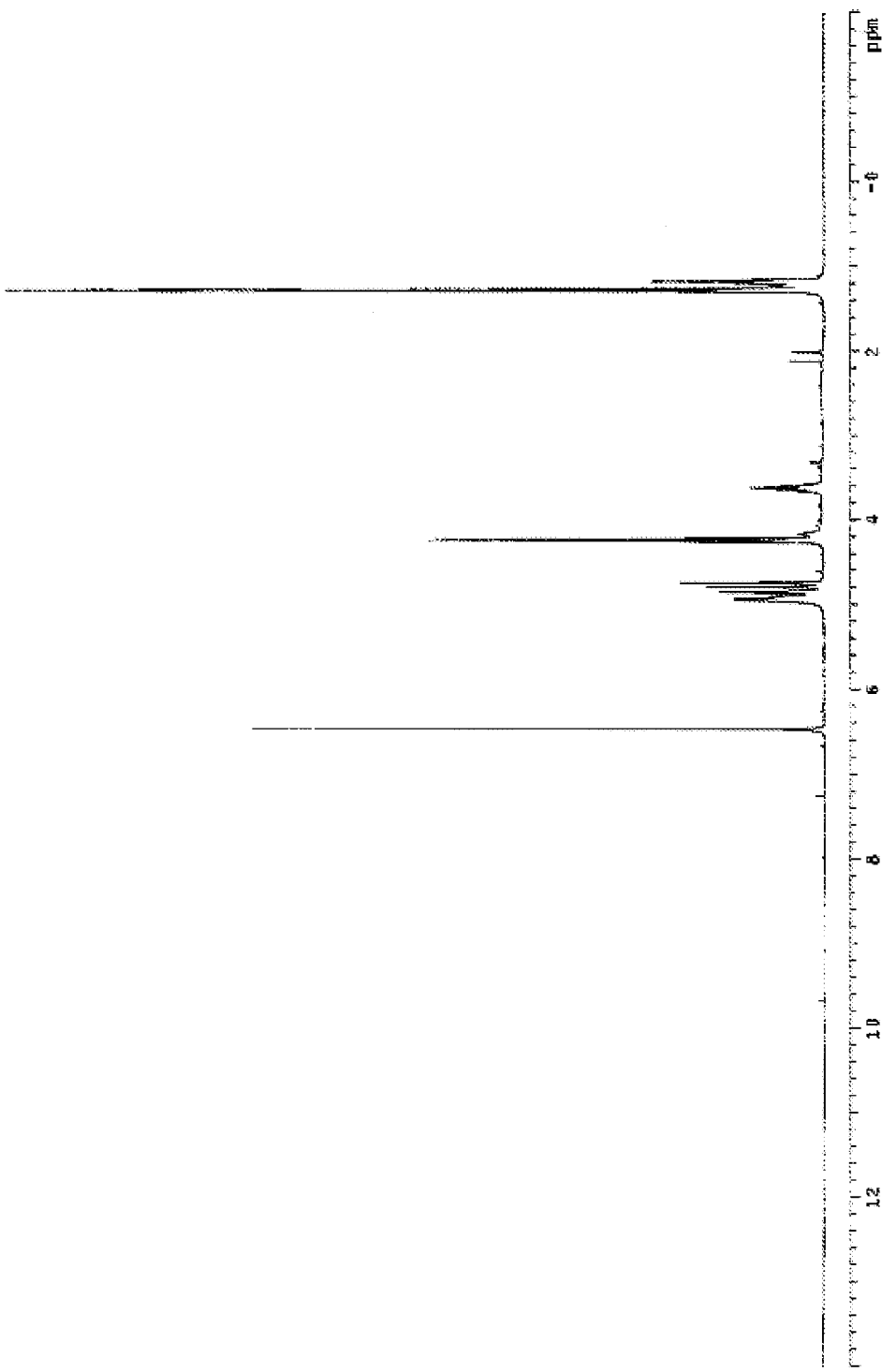
FIG. 6 depicts an NMR spectrum of crude Diethylmethylene Malonate produced by flash distillation method using 1 M % Zn(OAc)₂ Dihydrate.

The spectra presented in FIGS. 5-6 are representative for this crude material

The crude monomer (with 1000 ppm of HQ and 1000 ppm of sulfuric acid) was further fractionally distilled with a stainless steel packed column under reduced vacuum.

Pure monomer was collected at 55° C. with 1.1 mm Hg of vacuum. The pure monomer is stabilized with 1000 ppm of HQ and 10-50 ppm of chlorodifluoroacetic acid.

Figure 7:
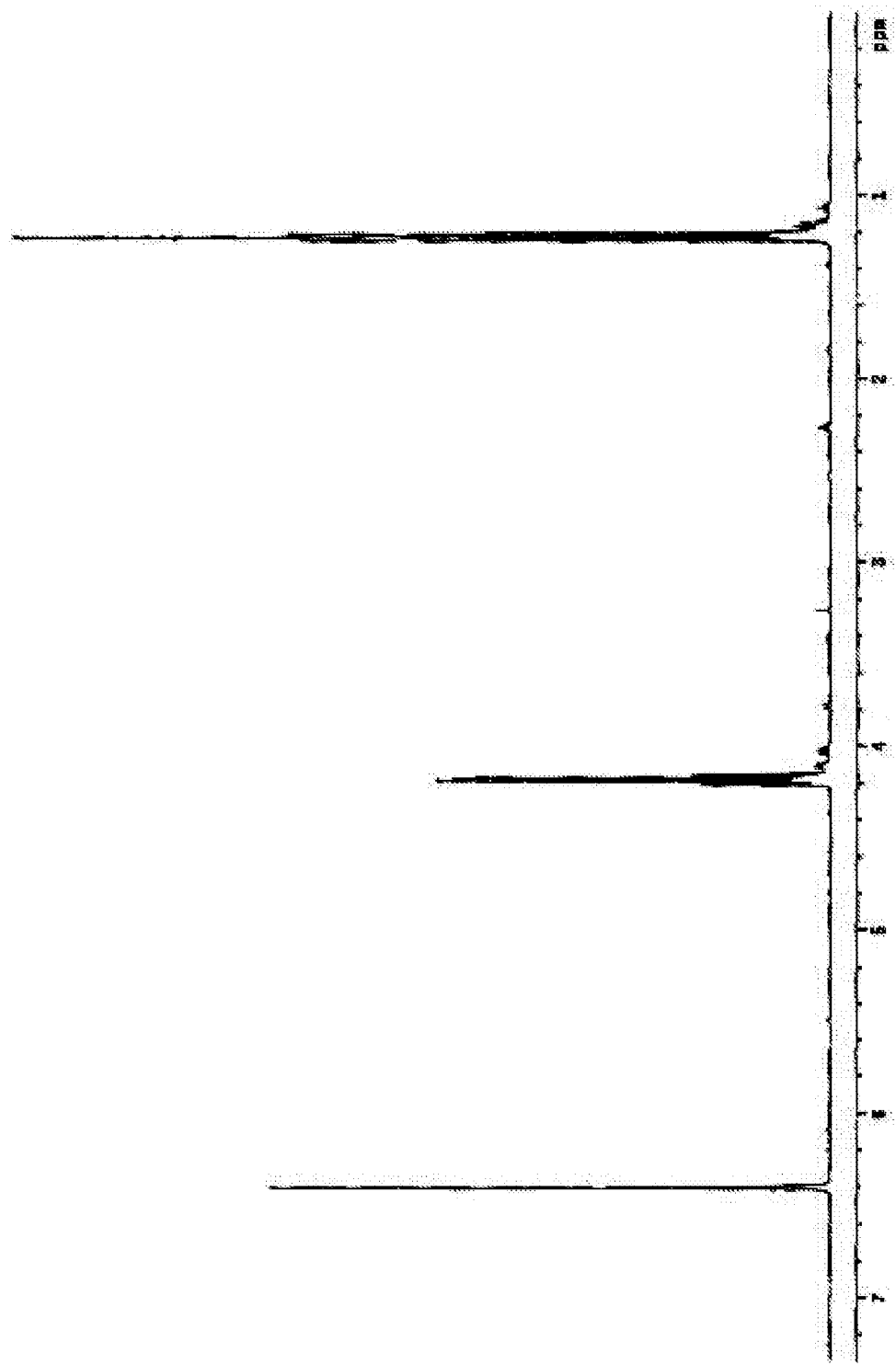
FIG. 7 depicts an NMR spectrum of pure Diethylmethylene Malonate produced by flash distillation method using 1 M % Zn(OAc)₂ Dihydrate.

The spectra presented in FIG. 7 is representative for this pure material

Example 2

Addition to Energy Transfer Means without Catalyst

Diethyl malonate (1 mol, 160 g), 60 g of paraformaldehyde (2 mol), were mixed and flash vaporized by slow addition to mineral oil (20 g) at 215° C. under a slow sweep of nitrogen. The distillation receiver was cooled to 0° C.

The distillate (crude monomer) was dried with sodium sulfate (5 g) and stabilized with 1000 ppm sulfuric acid and hydroquinone.

Yield=107 g for a qualitative yield of 37% with the remaining 25% being recyclable unreacted DEM for a real yield of 51%. Purity by GCMS=60% DEMM and 40% DEM plus minor impurities.

The crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum.

Purity by GCMS=99%. $^1$H-NMR (400 MHz, $CDCl_3$) δ 6.45 (s, 2H), 4.22 (q, 4H), 1.24 (t, 6H). GC-MS (m/z): calc. 172, 145, 127, 99, 55.

The pure Monomer was stabilized with 1000 ppm of HQ and 10-50 ppm of chlorodifluoroacetic acid.

Example 3

Slurry Heating with Heat Transfer Material Using Zn-Acetate Dihydrate Catalyst

Diethylmalonate (1 mole, 160 gm), Paraformaldehyde (1.5 moles, 45 gm), Silica Gel (30 gm) and Zn-Acetate Dihydrate (1 mole %, 2.2 gm) catalyst were placed in a 3 neck RBF and heated to 70° C. to initiate the reaction.

After 5 minutes the reaction temperature was raised up to 130° C. The exothermic nature was observed during 110-120° C. The heating mantle was removed during this period to avoid extreme heating. The reaction temperature was controlled by blowing $N_2$ through the reaction mixture The reaction was allowed to heat up to 200° C. and the crude product was collected in a receiver under reduced temperature.

Sulfuric acid (100 ppm) and Hydroquinone (1000 ppm) were used to stabilize the crude monomer. The colorless Methylene Malonate was recovered in a yield of 91%. GC/NMR Analysis of Crude:

a) 91% Methylene Malonate
b) 1% DEM
c) 2% Diethylmethyl Malonate d) 1% Mono-ol (Eventually convert to product at high temp).
e) 2% Diol
f) 2% Unknown with molar mass 212.

Figure 8:
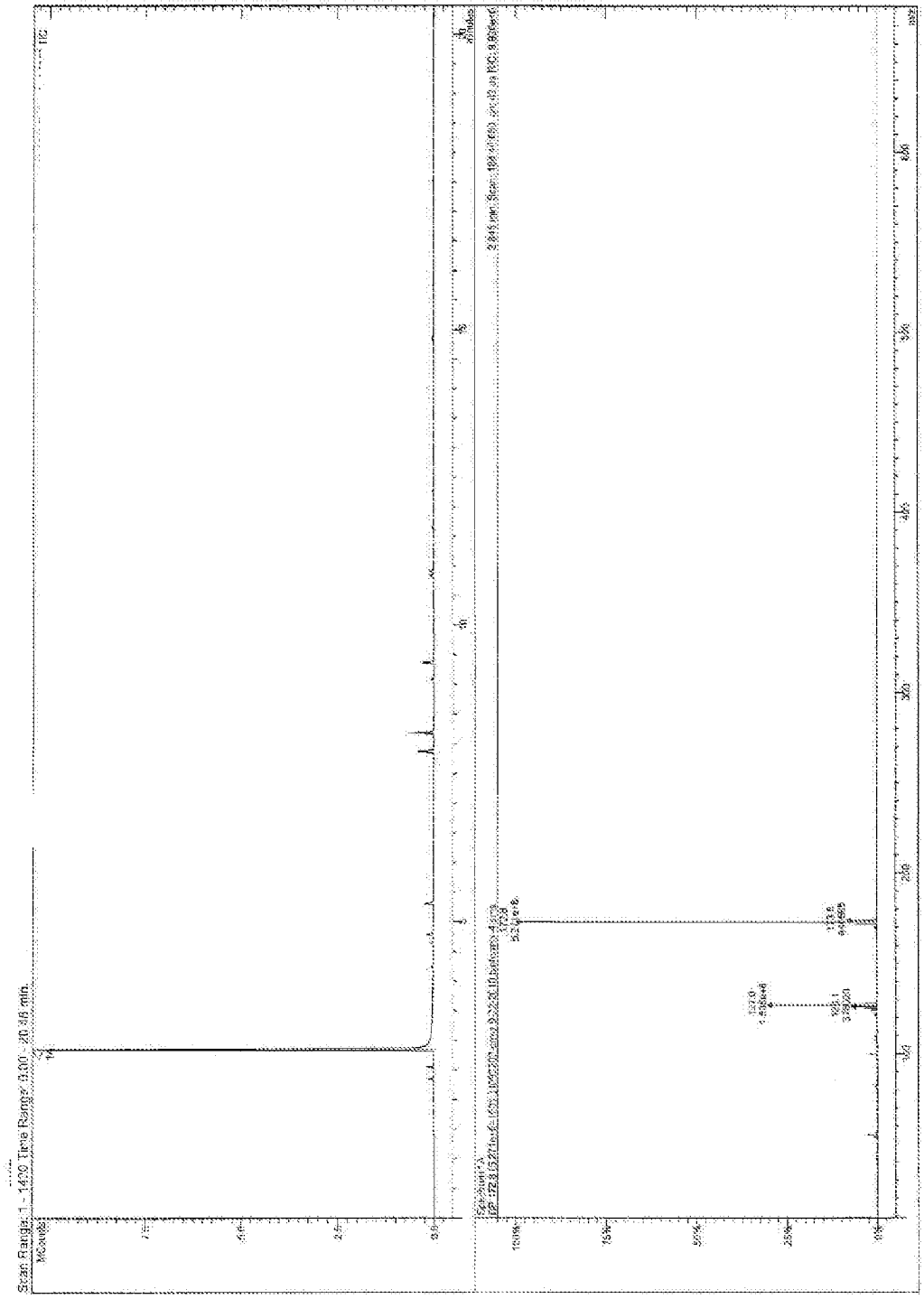
FIG. 8 depicts a GC-MS spectrum of crude Diethylmethylene Malonate produced by superheat distillation method using 1 M % Zn(OAc)₂ Dihydrate.
Figure 9:
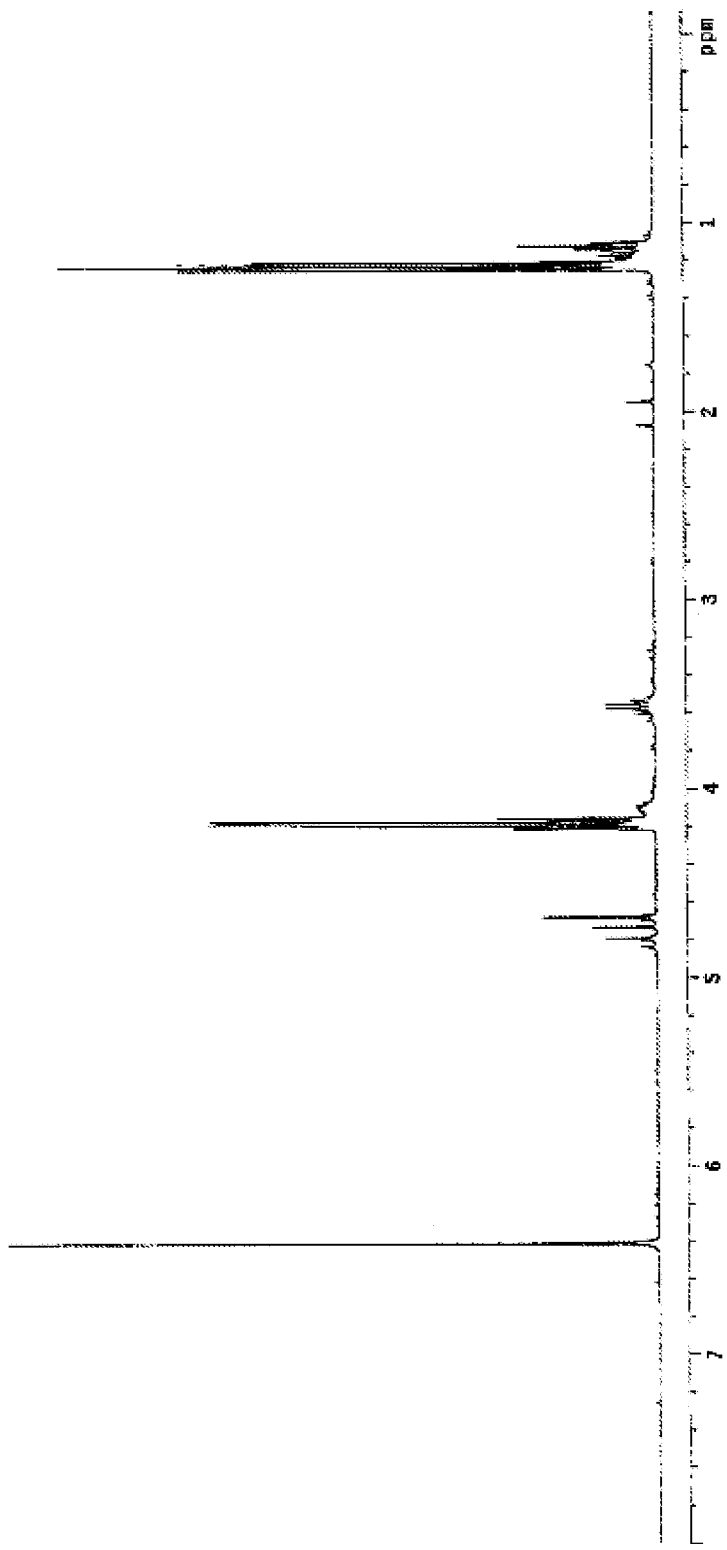
FIG. 9 depicts an NMR spectrum of crude Diethylmethylene Malonate produced by superheat distillation method using 1 M % Zn(OAc)₂ Dihydrate.

The spectra presented in FIGS. 8-9 are representative for this crude material

Pure Methylene Malonate product was collected by fractional distillation at about 2.5 mm and a temperature of 60° C. and stabilized with strong acid and other traditional stabilizers in the collection flasks such that the final concentration was about (10 ppm) sulfuric acid.

The purified yield of Methylene Malonate was ~65%.
GC Analysis (m/z): 172, 143, 127, 99, 72, 55, 29
NMR Analysis (CDCl$_3$, δ ppm): 6.35 (Singlet), 4.15 (Quartet), 1.18 (Triplet)
Purity: a) 99% Methylene Malonate
b) 0.5% DEM
c) 0.5% Diethylmethyl Malonate Note: After collecting ~90% product from the reaction mixture, the product was very thick and started polymerizing inside the flask. Overheating must be avoided because at higher temperature (>240° C.) the Diethylmethyl malonate was formed at a higher percentage with respect to lower temperature.

Figure 10:
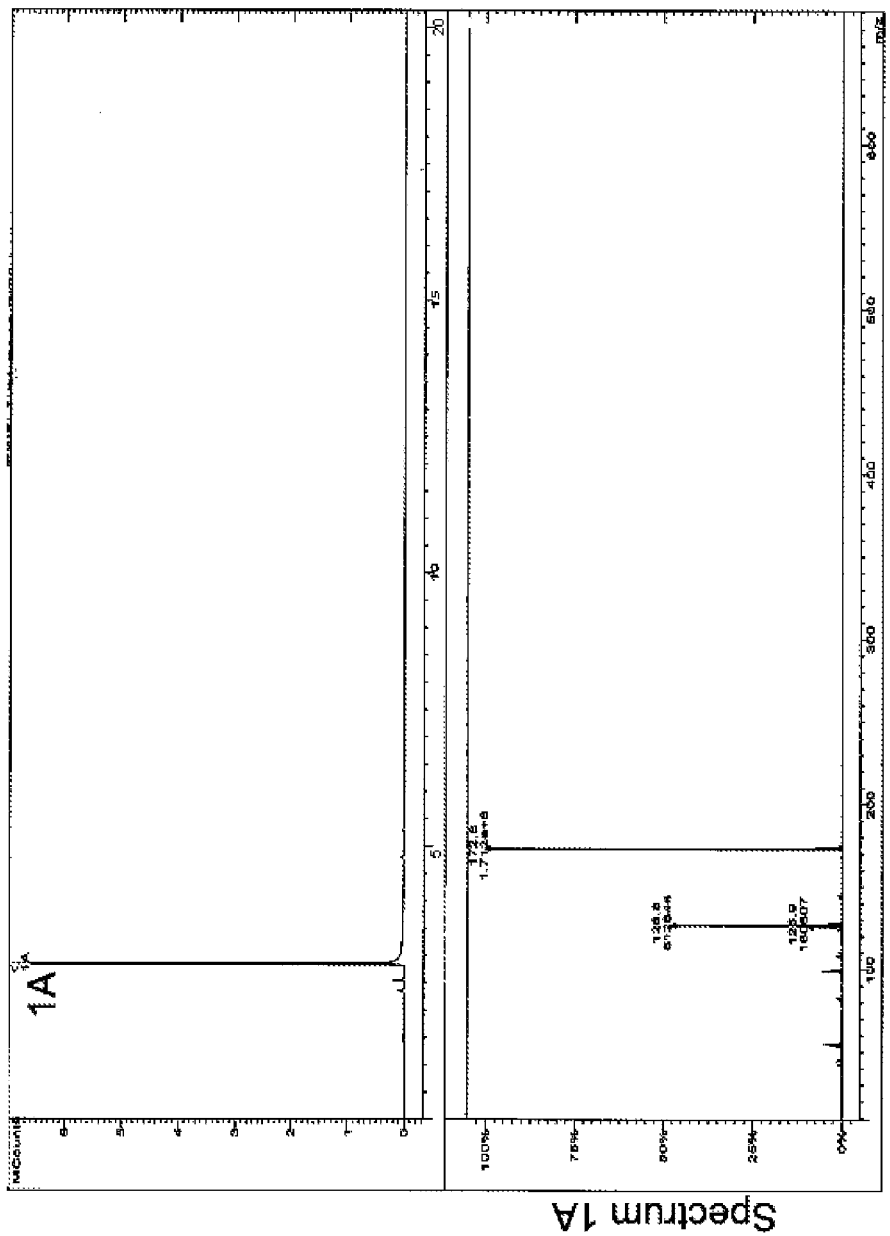
FIG. 10 depicts a GC-MS spectrum of pure Diethylmethylene Malonate produced by superheat distillation method using 1 M % Zn(OAc)₂ Dihydrate.
Figure 11:
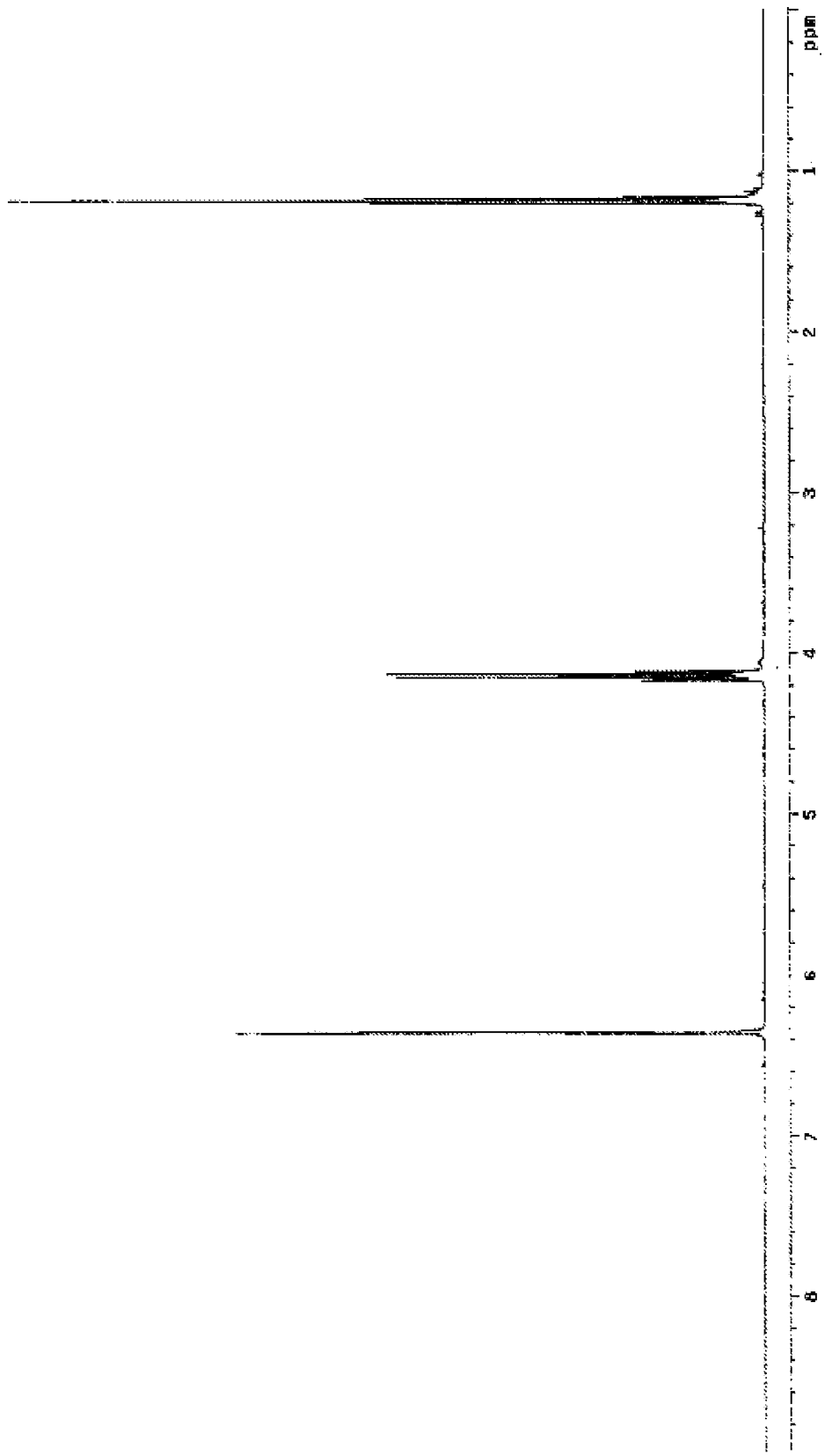
FIG. 11 depicts an NMR spectrum of pure Diethylmethylene Malonate produced by superheat distillation method using 1 M % Zn(OAc)₂ Dihydrate.

The spectra presented in FIGS. 10-11 are representative for this pure material

Example 4

Slurry Heating with Heat Transfer Material Synthesis and Characterization of Ditert.Butyl-2-Methylenemalonate Using Zn(OAc)$_2$, 2H$_2$O as a Catalyst Materials.
Toluene, Paraformaldehyde, Zn(OAc)$_2$, 2H$_2$O were purchased from Acros Organics and used as received. Ditert.butyl malonate was purchased from Alfa Aesar and used as received.

Experimental Procedure
A 3-neck RBF, with a mechanical stirrer inside, was first dried to make it moisture free, fitted with thermocouple and the Dean Stark apparatus connected with a condenser.
1) The reaction solvent, 100 mL of Toluene was then transferred to the RBF. 54 gm of Ditert.butyllmalonate (DTBM) (0.25 moles), 2.2 gm of Zn(OAc)$_2$ dihydrate (0.01 moles), 15 gm (0.5 moles) of Paraformaldehyde were all added to the reaction medium sequentially.
2) The initial color of the reaction mixture was milky white. The reaction mixture was then heated to 65° C. for 30 mins.
3) After heating for 30 mins the reaction temperature was raised to 100° C. and maintained for another 30 mins.
4) The reaction mixture became transparent after 10 minutes, indicating the complete conversion of starting material which was also indicated by GC.
5) After the complete conversion of starting material, the intermediate product was distilled off along with water and toluene fractions.
6) The reaction temperature was then raised to 110° C. with constant flow of N$_2$ through the reaction mixture. Initial water formation was observed and collected inside a flask.
7) After collection of 5-6 ml of water/Toluene mixture, the temperature was raised up to 140° C. where mostly Toluene was collected along with very little amount of Ditert butyl 2-methylene malonate.
8) The temperature was further increased to 180° C. where collection started for the pure Ditert.butyl 2-methylene malonate started coming.
9) Most Ditert.butyl 2-methylene malonate was collected within the temperature range of 180-200° C. with constant blowing of N$_2$.
10) 28.5 gms of pure Ditert.butyl 2-methylene malonate was collected with an overall yield of ~50%.
11) The purity of monomer was confirmed by GC/MS and $^1$H NMR.
12) The monomer was stabilized with 100 ppm of HQ with 1000 ppm of chlorodifluoro acetic acid.
NMR DATA: 1H NMR (CDCl3, 400 MHz, d): 6.45 (2H, singlet), 1.22 (9H, singlet).
Purity: 98%, 2% solvent toluene
GC/MS (m/z)=173, 117, 57, 41

Figure 12:
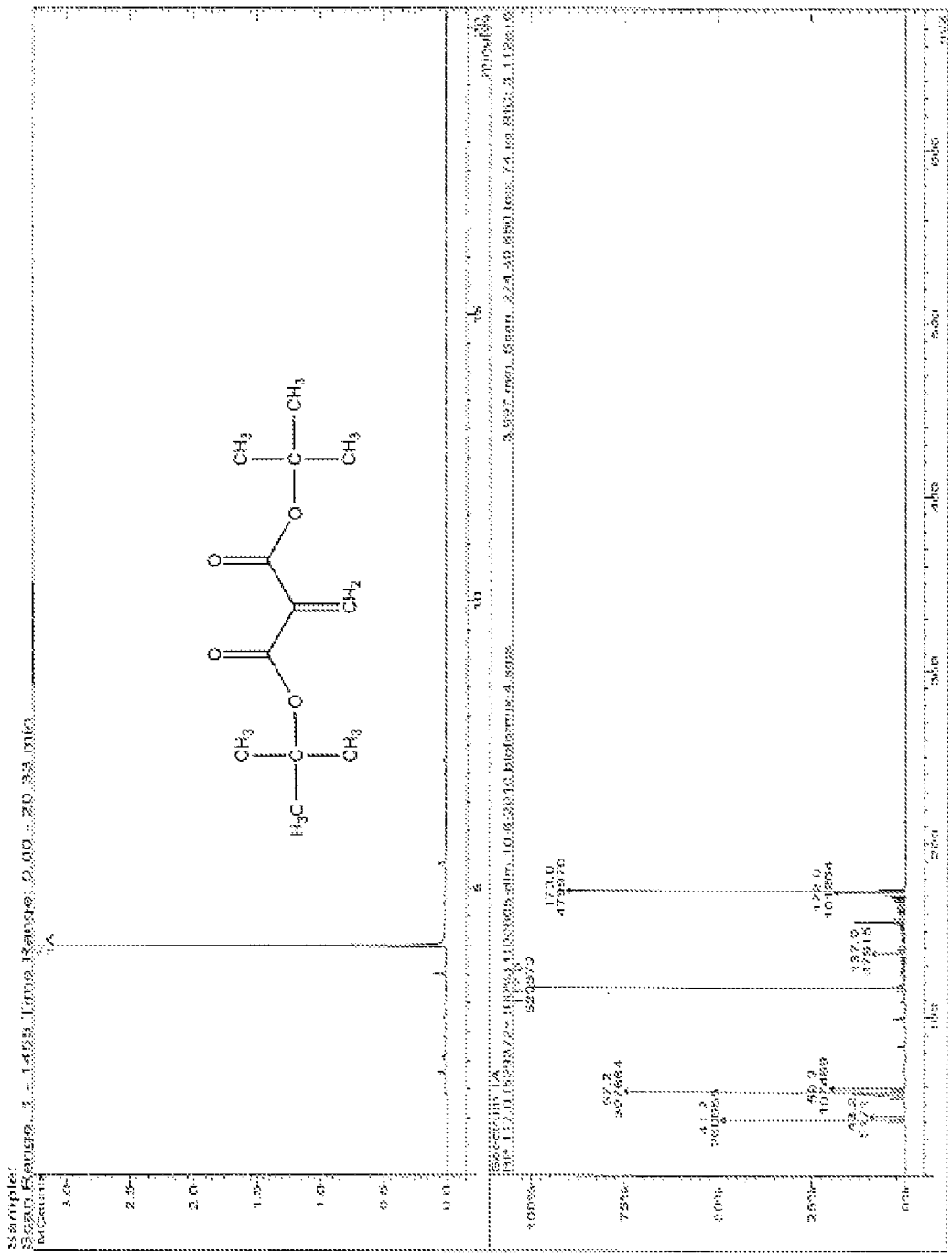
FIG. 12 depicts a GC-MS spectrum of pure Di-(tert-butyl)-methylene Malonate produced by superheat distillation method using Zn(OAc)₂ Dihydrate.
Figure 13:
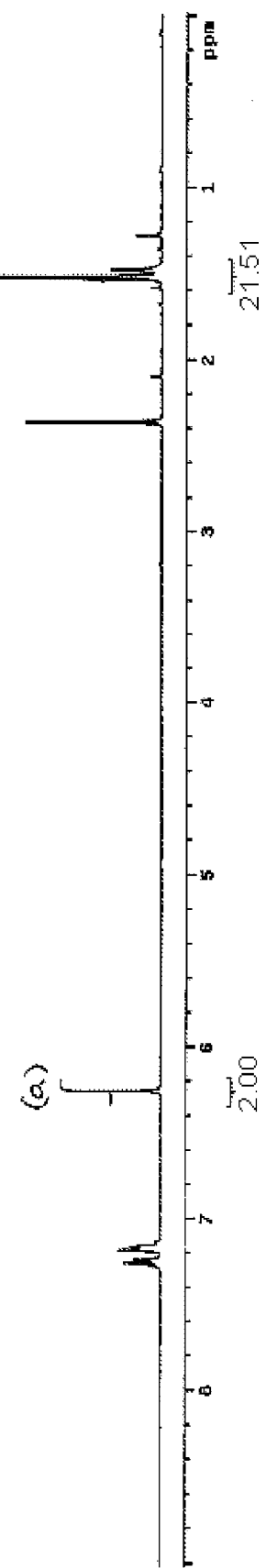
FIG. 13 depicts an NMR spectrum of pure Di-(tert-butyl)-methylene Malonate produced by superheat distillation method using Zn(OAc)₂ Dihydrate.

The spectra presented in FIGS. 12-13 are representative for this pure material

Example 5

Four (4)—Stage Process to Form Diethyl Methylene Malonate Monomer

Stage 1: Condensation Reaction
(1) Combining reaction components in a 3 liter flask (equipped with reflux condenser, thermometer and mechanical stirrer) to form a reaction mixture, said reaction components comprising diethylmalonate (1.6 kg, 10 mol), paraformaldehyde (600 g, 20 mol) and zinc acetate dihydrate (4 g), wherein the diethylmalonate and the paraformaldehyde are combined in a molar ratio of 1:2.
(2) Heating the reaction mixture to about 70° C. and allow reaction temperature to exothermically rise to about 130° C. for about 5 minutes, thereby forming a reaction complex that comprises specific oligomeric-sized molecules from which methylene malonate monomers may be "cracked" or otherwise derived therefrom.
(3) Optionally cooling reaction mixture to room temperature.
(4) Optionally analyzing reaction mixture by GCMS, HNMR or CNMR.

Stage 2: Flash Distillation to "Crack" Reaction Complex to Form Monomer Product
(5) Prepare a 3-neck 1-liter RB flask with an additional funnel, a stillhead, a condenser and a chilled (15-20° C.) receiving flask and fill the addition funnel with reaction complex (1.9 kg). Contacting the reaction complex with a "cracking fluid" (e.g., 25-50 mL of mineral oil or reaction complex for the distillation of a 2 liter volume of reaction complex) or an equivalent type of heat transfer means (which can be the flask glassware itself or other materials as defined herein) to the RB flask and pre-heat the cracking fluid to between about 150-300° C. Distilling reaction complex by adding the reaction complex to the cracking fluid (or equivalent heat transfer means) while maintaining RB flask temperature above between about 150-300° C. and collecting distillate. The threshold temperature at which DEMM monomer begins to be formed, i.e., "cracked" or formed from the reaction complex, is about 150° C. Best results are observed where flask is maintained at about 250° C.
(6) Add to the distillate 50 ppm methane sulfonic acid and 50 ppm of chlorodifluoroacetic acid to stabilize the DEMM monomer in the distillate;
(7) Optionally analyzing distillate by GCMS, HNMR or CNMR to estimate purity of the DEMM monomer;

Stage 3: Washing Stage (8) Optionally washing distillate with water (2×500 mL) by stirring distillate vigorously for 20 minutes and allow to settle for 20 minutes. Separate lower organic layers (which contains product) and repeat. Dry organic layer with MgSO$_4$ (50 g). Filter to remove MgSO$_4$.

(9) Add to the organic layer 50 ppm methane sulfonic acid and 50 ppm of chlorodifluoroacetic acid to stabilize the DEMM monomer;

(10) Optionally analyze by GCMS, HNMR or CNMR and estimate purity of DEMM monomer;

Stage 4: Fractional Distillation

(11) Add to the DEMM monomer 2000 ppm hydroquinone, 1000 ppm P$_2$O$_5$ and 50 ppm of chlorodifluoroacetic acid. Obtain fractional distillation apparatus comprised of a single neck 500 mL round bottom flask, a 20" Monel packed column (porous stainless steel packing), and fractional distillation stillhead designed for controllable reflux return. The receiver flask is cooled with dry ice/acetone and there is a dry ice/acetone cold trap between the still and the vacuum pump. Vacuum is applied with typical vacuums of 1-2 mm Hg and significant degassing is observed. Low boilers can be seen at this point collecting in the receiver flask and cold trap. Add water-washed distillate to round bottom flask.

(12) Heat the still pot to 120° C. Additional low boilers collect in the receiver as well as in the cold trap. Distillation pressure increases to 3-5 mm Hg. The polymethylene glycols start depolymerizing and formaldehyde starts emanating from the vacuum pump in the exhaust as temperature increases. As the collection of the low boiling by-products slows down, the contents of the still pot turns cloudy. The monomeric formaldehyde continues to form until the cloudiness disappears. Throughout this stage head temperature rises from 20° C. to 40° C. The pressure slowly comes down from 3 mm Hg to less than 1 mm Hg. At this point the temperature is increased to 130° C., the pressure continues to go down slowly (0.5 mm Hg-0.7 mm Hg) and the head temperature rises to 50° C.-55° C. The receiver flask is replaced and product is then collected. Distillation pot temperature is slowly increased incrementally to 150° C. with product collected between head temperatures of 50° C.-60° C.

(13) Raise pot temperature to 100-115° C., with vacuum at 0.5 mmHg, head temperature at 32° C., collect distillates of high purity DEMM monomer.

(14) Add to the organic layer 50 ppm methane sulfonic acid and 50 ppm of chlorodifluoroacetic acid to stabilize the DEMM monomer.

(15) Optionally analyze by GCMS, HNMR or CNMR and estimate purity of DEMM monomer.

Example 6

Large Scale Preparation of Diethyl Methylene Malonate Oligomeric Complex Using Fresh Formaldehyde 1. Paraformaldehyde 550 g (18.33 mol), Diethyl Malonate 1600 g (10 mol) and Zinc acetate 2 g (0.01 mol) were mixed together at 70° C.
2. The reaction system was allowed to exotherm to 135° C. and forms a crude reaction complex
3. The system was allowed to cool to 90° C.
4. GCMS samples of compositions were then prepared in 0.1% solution of ethyl acetate and NMR samples were prepared by dissolving compositions in CDCl$_3$ solvent.
5. The crude reaction complex is then added slowly to a heated surface (190° C.) under vacuum (50-150 mmHg) to produce crude monomer and other byproducts which are then distilled to produce Diethyl Methylene Malonate.

| Reaction Complex Yield Calculation Reactant | MW (g/mol) | Moles | Amount (g) |
|---|---|---|---|
| DEM | 160 | 10 | 1600 |
| Formaldehyde | 30 | 18.33 | 550 |
| Reaction Complex (g) | 2150 | | |
| % DEM from NMR | 5% | | |
| Unreacted DEM (g) | 107 | | |
| Oligomeric Complex (g) | 2042 | | |
| Reacted DEM (g) | 1493 | | |
| Theoretical DEMM (g) | 1604 | | |
| Unreacted Paraformaldehyde (g) | 438 | | |
| Product collected (g) | 1473 | | |
| % DEMM from NMR | 82% | | |
| DEMM collected (g) | 1208 | | |
| % Yield before distillation | 75% | | |

Example 7

Representative Process for Forming Dimethyl Methylene Malonate Monomers

In this Example, dimethyl methylene malonate was synthesized via a modified Knoevenagel Condensation reaction with 50% yield. This process, which improves significantly on prior Methylene Malonate synthesis, entails a Knoevenagel reaction between dimethyl malonate, paraformaldehyde and zinc acetate dihydrate as catalyst. The first step in this reaction yields a reaction complex which may contain, among other things, an oligomeric product that may consist of alternating units of methylene malonate and formaldehyde. A novel depolymerization cracking process then gives dimethyl methylene malonate (DMMM).

The overall reaction scheme below outlines the synthetic route used to synthesize DEMM. Dimethyl malonate was reacted with paraformaldehyde in the presence of zinc acetate dihydrate as catalyst at 105° C. for 30 minutes. The immediate product of this reaction is, without wishing to be bound by any theory or mechanism, an oligomeric material with repeating units comprising of alternating dimethyl malonate and formaldehyde. This oligomeric material is then thermally depolymerized or "cracked" to DMMM by addition to a hot surface set from 190° to 270° C. (or otherwise contacting with a means to heat or otherwise transfer sufficient energy to the reaction complex or oligomeric material to achieve the cracking of the oligomeric material to form the DMMM). The resulting crude DMMM monomer is then fractionally distilled to afford pure dimethyl methylene malonate. The reaction scheme is shown below:

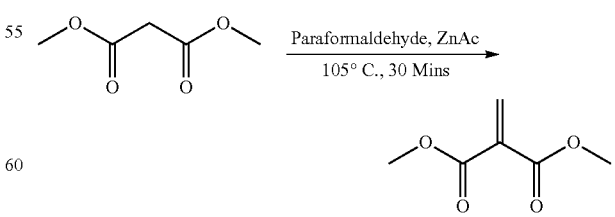

Figure 14:
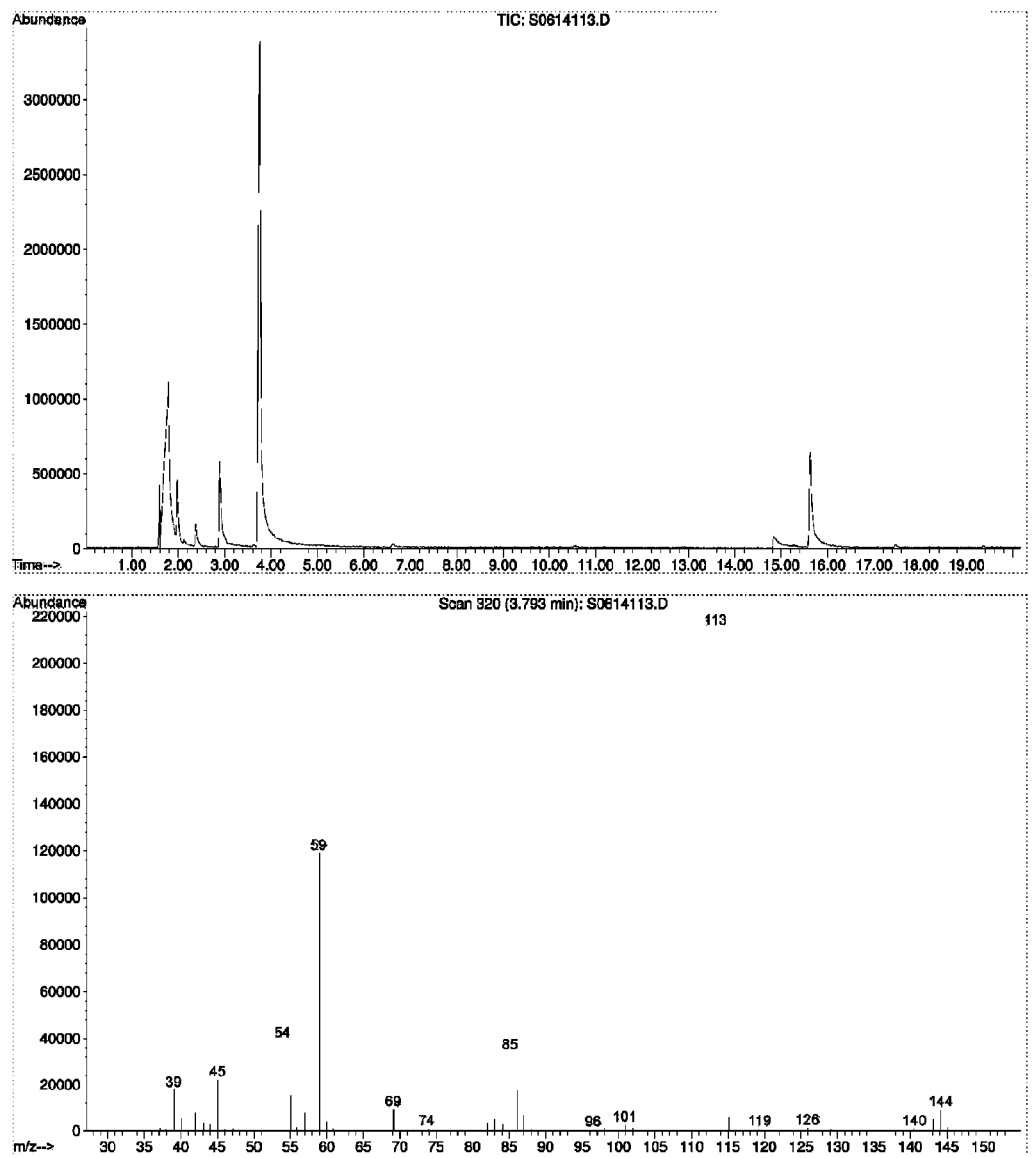
FIG. 14 depicts GC spectra for dimethyl methylene malonate oligomeric product formed in the reaction complex as a result of the condensation reaction outlined in Example 6.

The specific process proceeded as follows:

A 3-neck 500 mL round bottom flask was charged with 200 g (1.5 mol) dimethyl malonate (DMM), 96 g (3.2) paraformaldehyde, and 0.3 g (0.0015 mol) Zn acetatdihydrate. A reflux condenser, a thermocouple and a stopper were then attached to the flask. The thermocouple was then set to 105° C. and the contents of the flask were heated. After approximately 15 minutes the reaction exothermed to 130° C. with a concurrent clarification of the mixture to opaque, viscous slurry. The reaction was run for an additional 15 minutes after which time it was allowed to cool to 90° C. The warm reaction complex was then placed in a 250 mL addition funnel which was attached to a 3-neck 250 mL round bottom flask, seated in a heating mantle. The GC spectra shown in FIG. 14 is representative of the reaction complex material.

Figure 15:
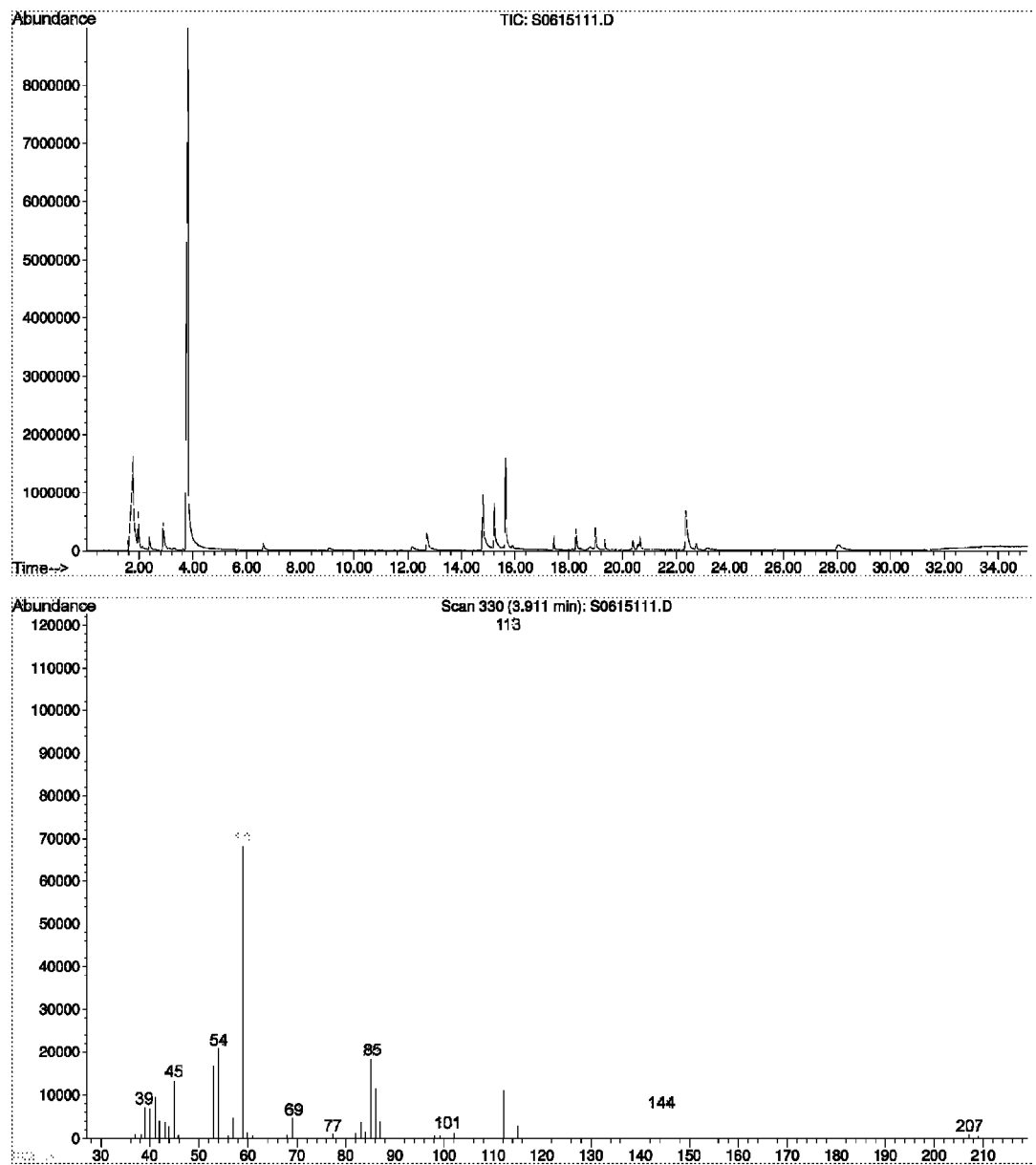
FIG. 15 depicts GC spectra for dimethyl methylene malonate crude ("cracked") product prior to fractional distillation in accordance with the process of Example 6.
Figure 16:
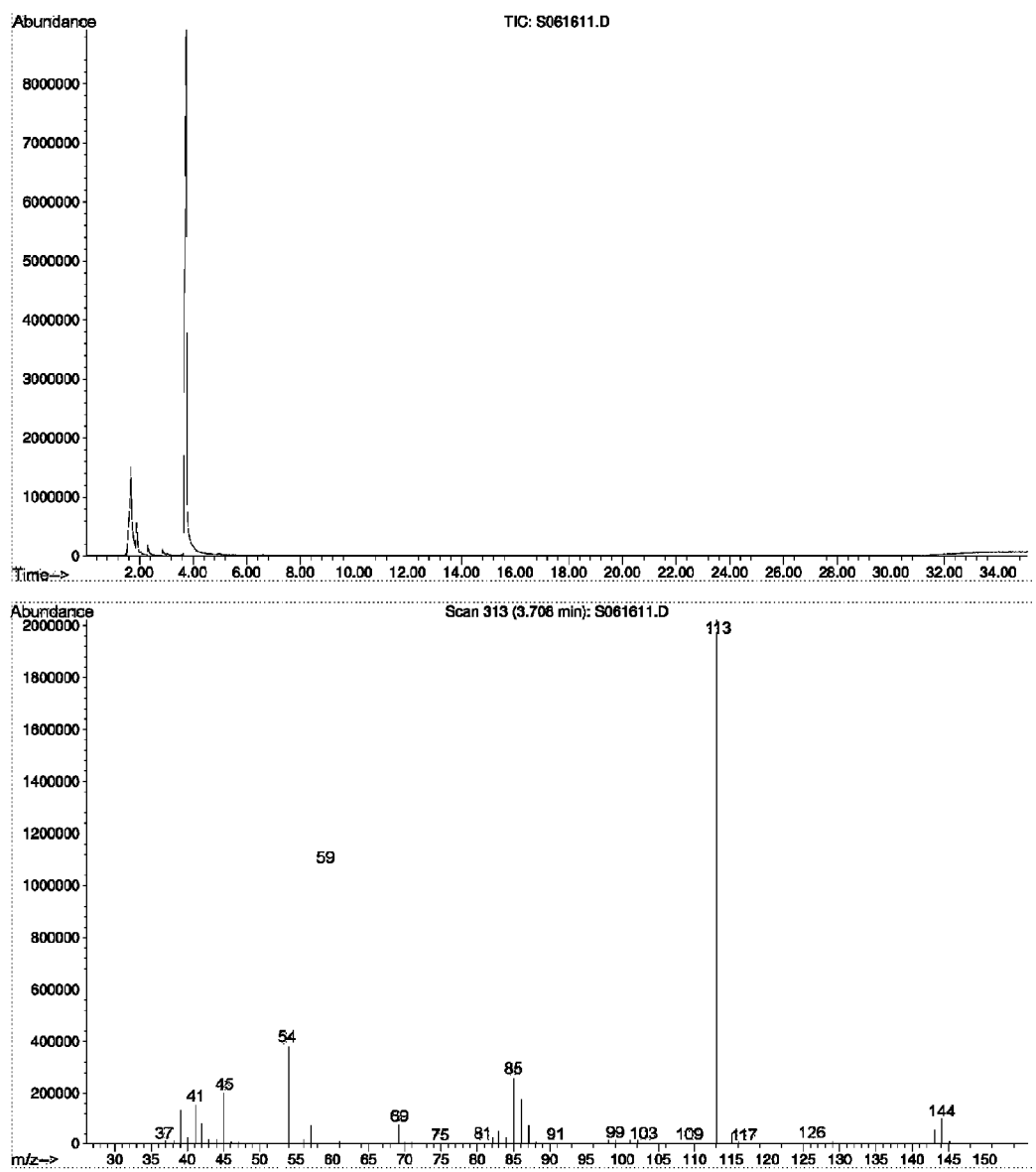
FIG. 16 depicts GC spectra for dimethyl methylene malonate product after fractional distillation in accordance with the process of Example 6.
Figure 17:
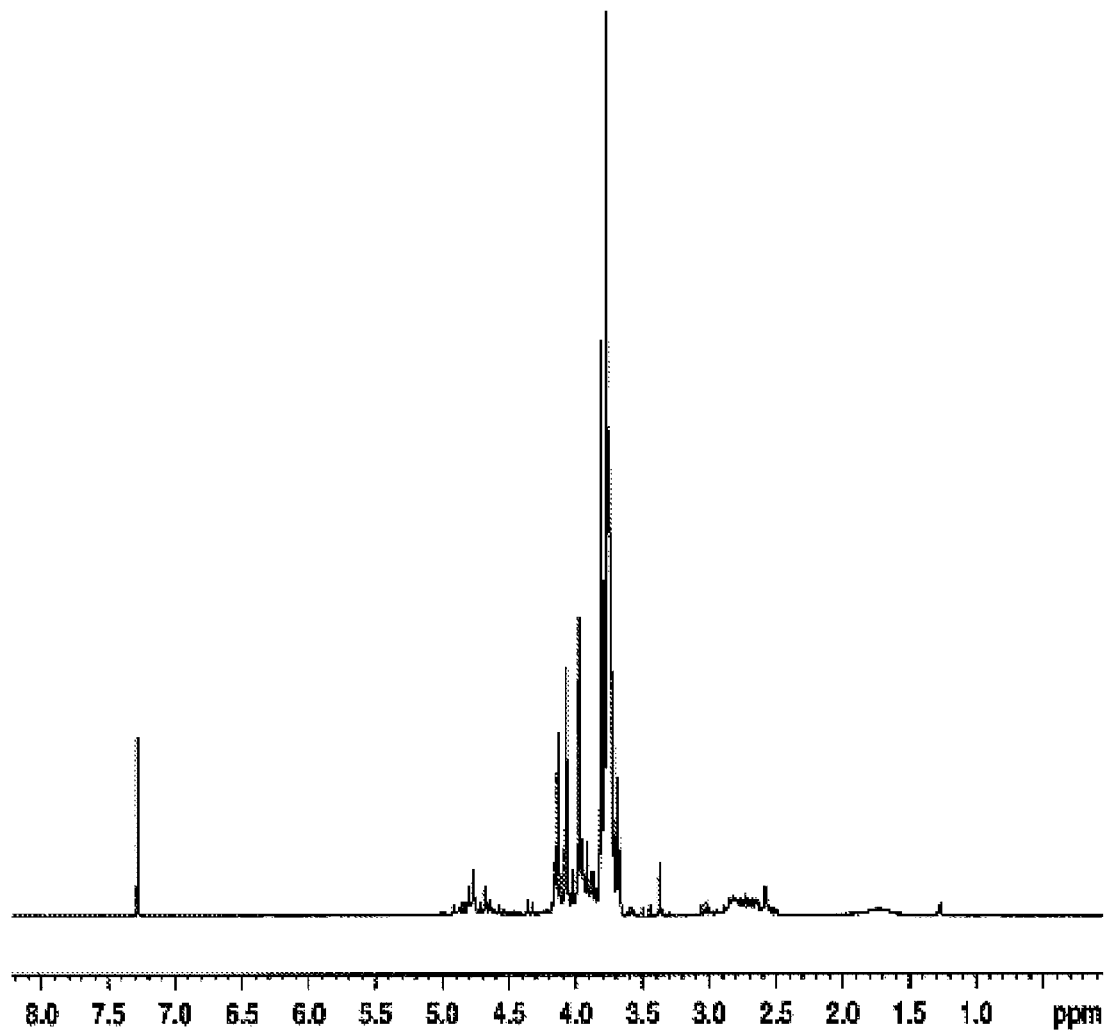
FIG. 17 depicts the ¹H NMR spectra of DMMM oligomeric product in CDCl₃ formed in accordance with the process of Example 6.
Figure 18:
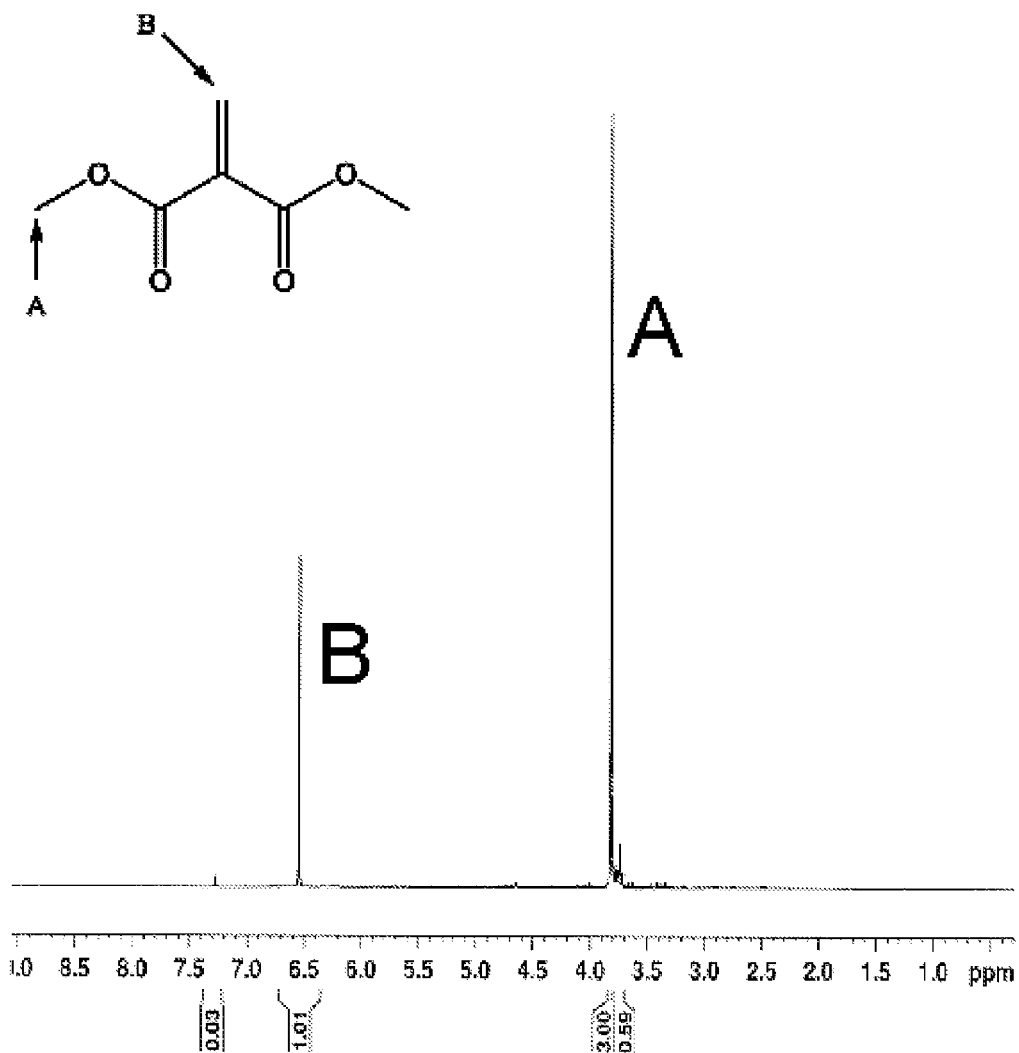
FIG. 18 depicts the ¹H NMR spectra of crude DMMM in CDCl₃ formed in accordance with the process of Example 6.
Figure 19:
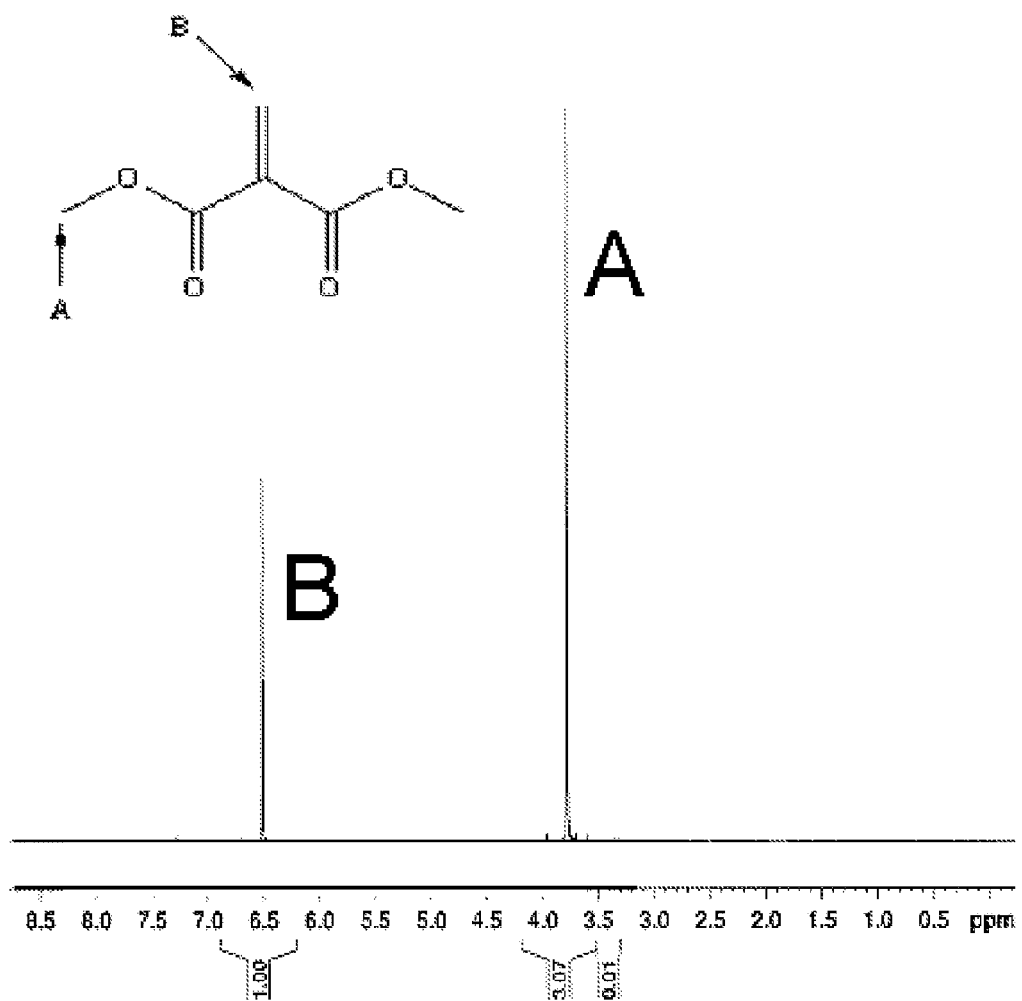
FIG. 19 depicts the ¹H NMR spectra of 99% DMMM in CDCl₃ formed in accordance with the process of Example 6.
Figure 20:
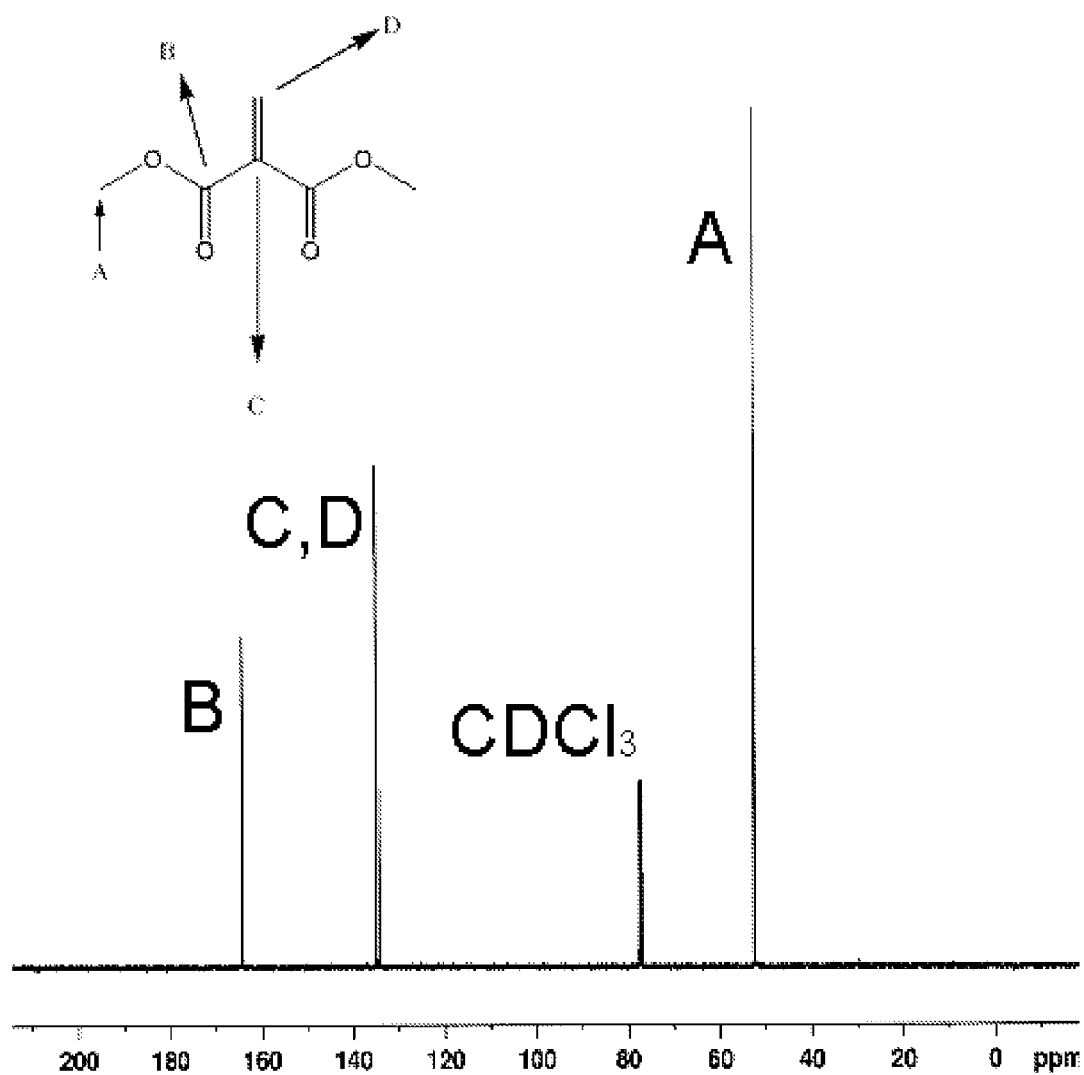
FIG. 20 depicts the ¹H NMR spectra of 99% DMMM in CDCl₃ formed in accordance with the process of Example 6.
Figure 21:
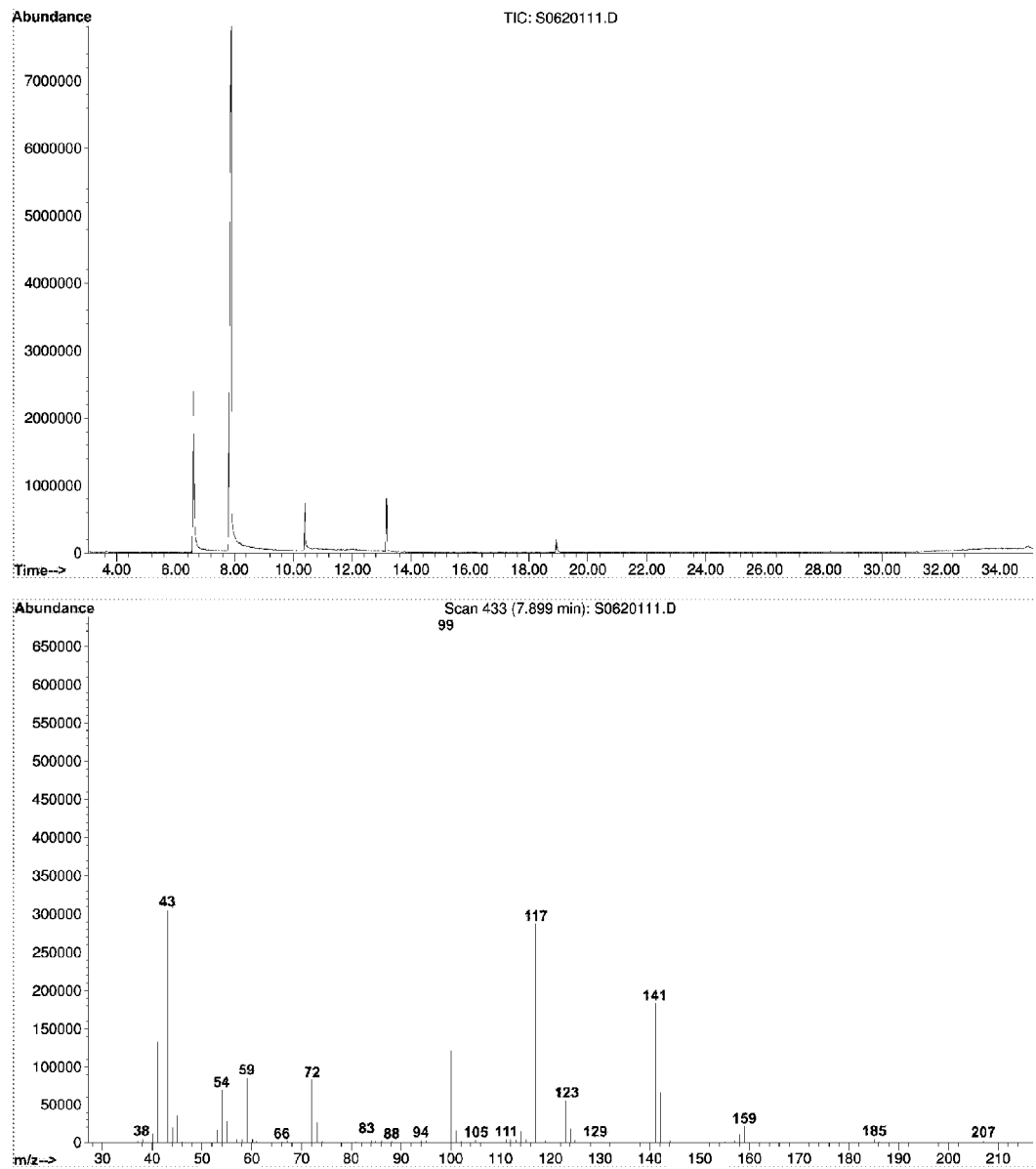
FIG. 21 depicts GC spectra for diisopropyl methylene malonate (DIPMM) oligomeric product formed in the reaction complex as a result of the condensation reaction outlined in Example 7.
Figure 22:
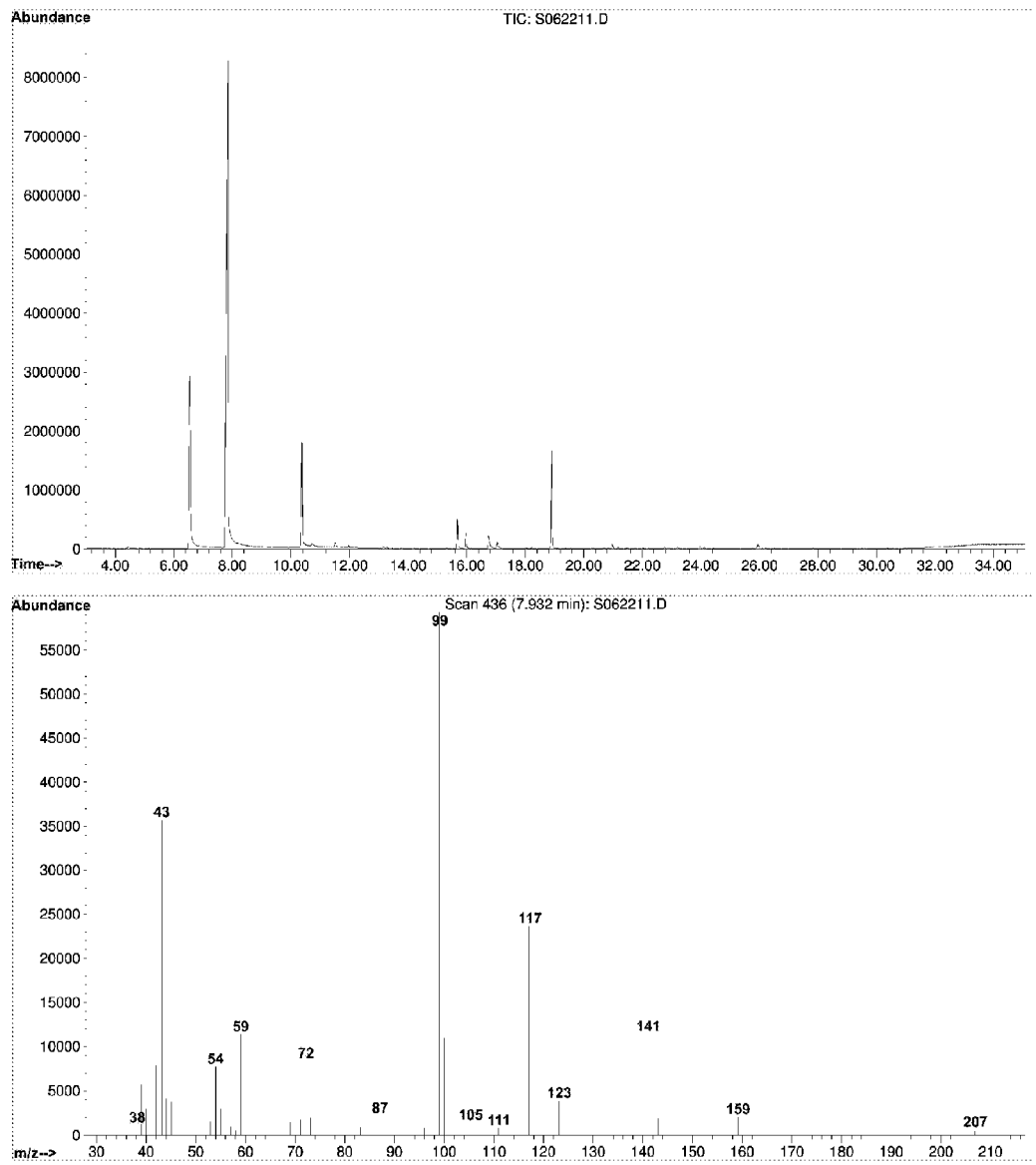
FIG. 22 depicts GC spectra for diisopropyl methylene malonate (DIPMM) crude ("cracked") product prior to fractional distillation in accordance with the process of Example 7.
Figure 23:
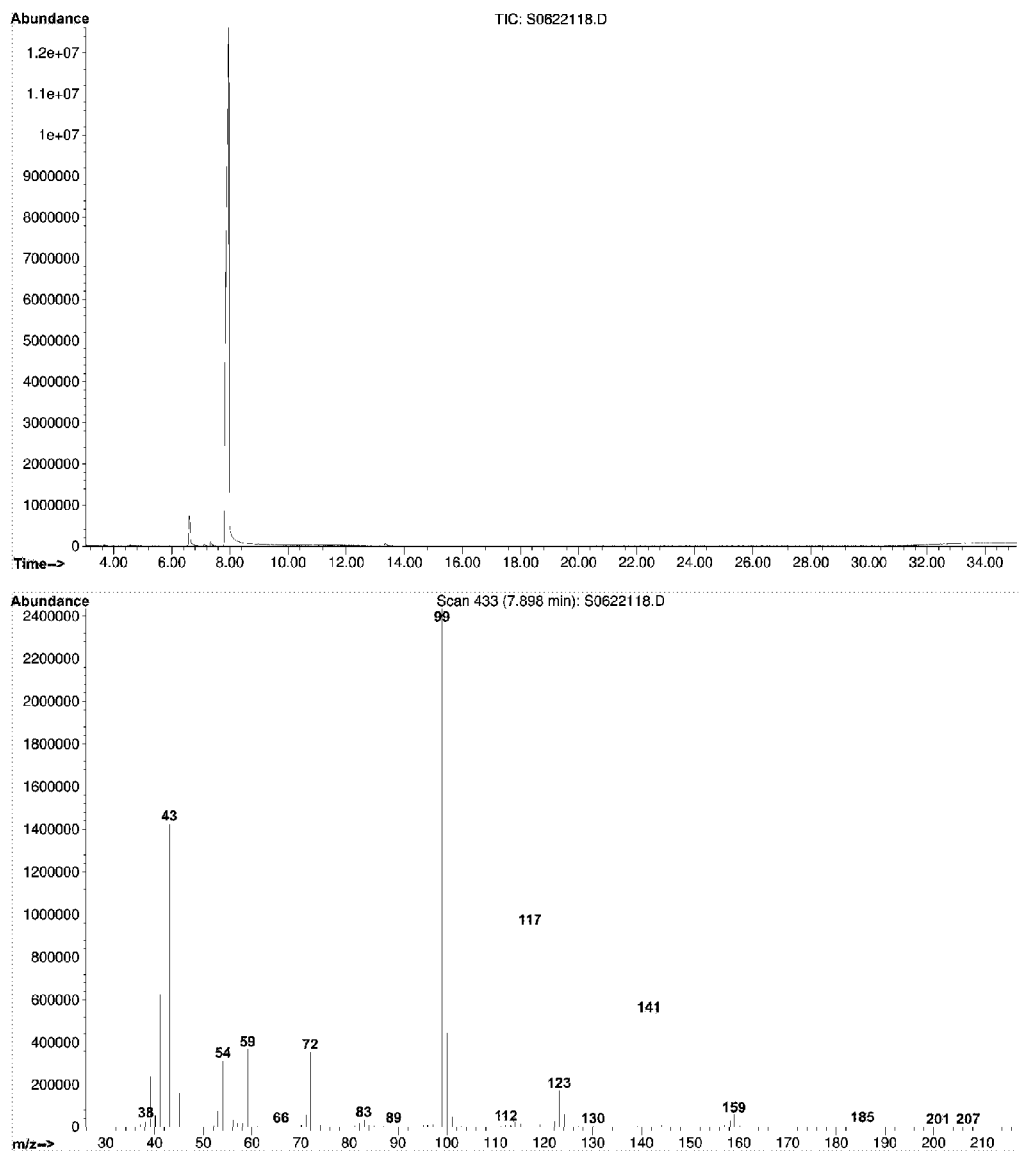
FIG. 23 GC depicts GC spectra for diisopropyl methylene malonate (DIPMM) product after fractional distillation in accordance with the process of Example 7.
Figure 24:
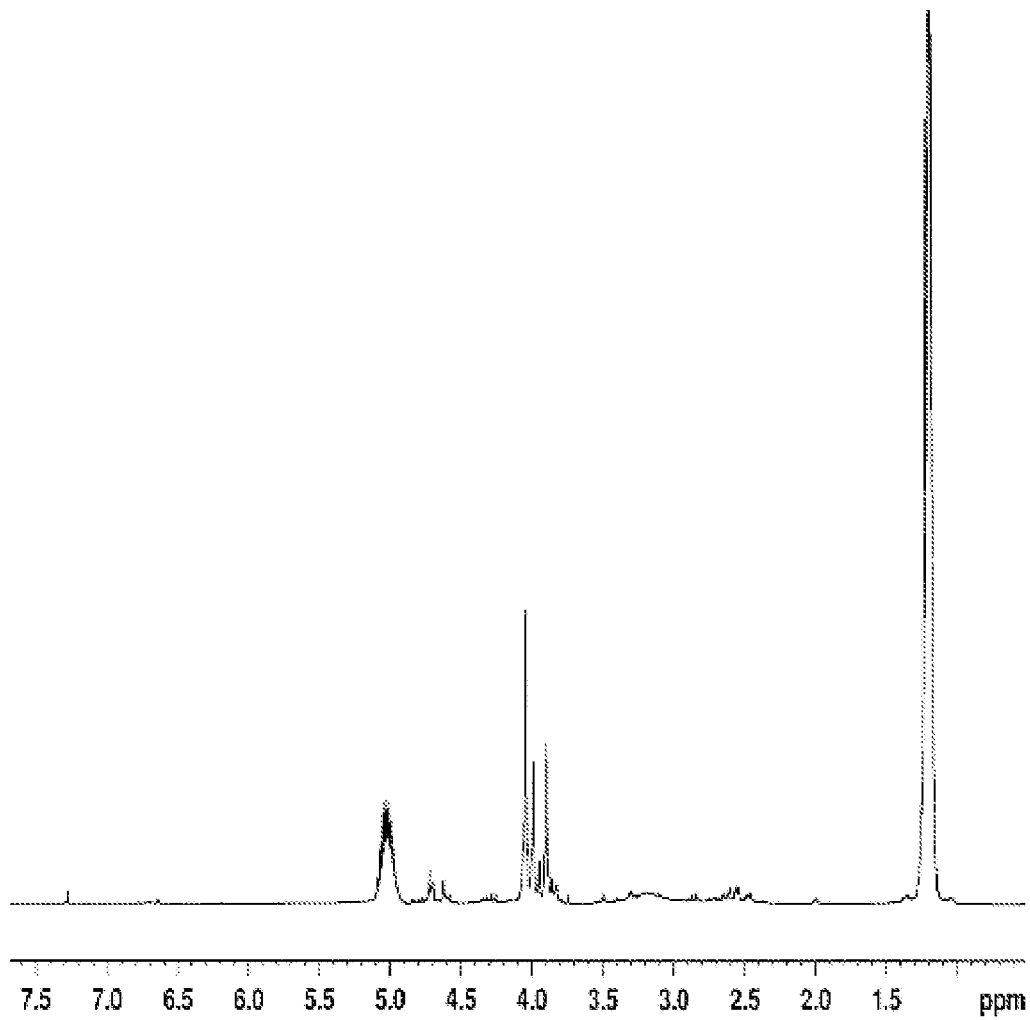
FIG. 24 depicts the $^1$H NMR spectra of DIPMM oligomeric product in CDCl$_3$ formed in accordance with the process of Example 7.
Figure 25:
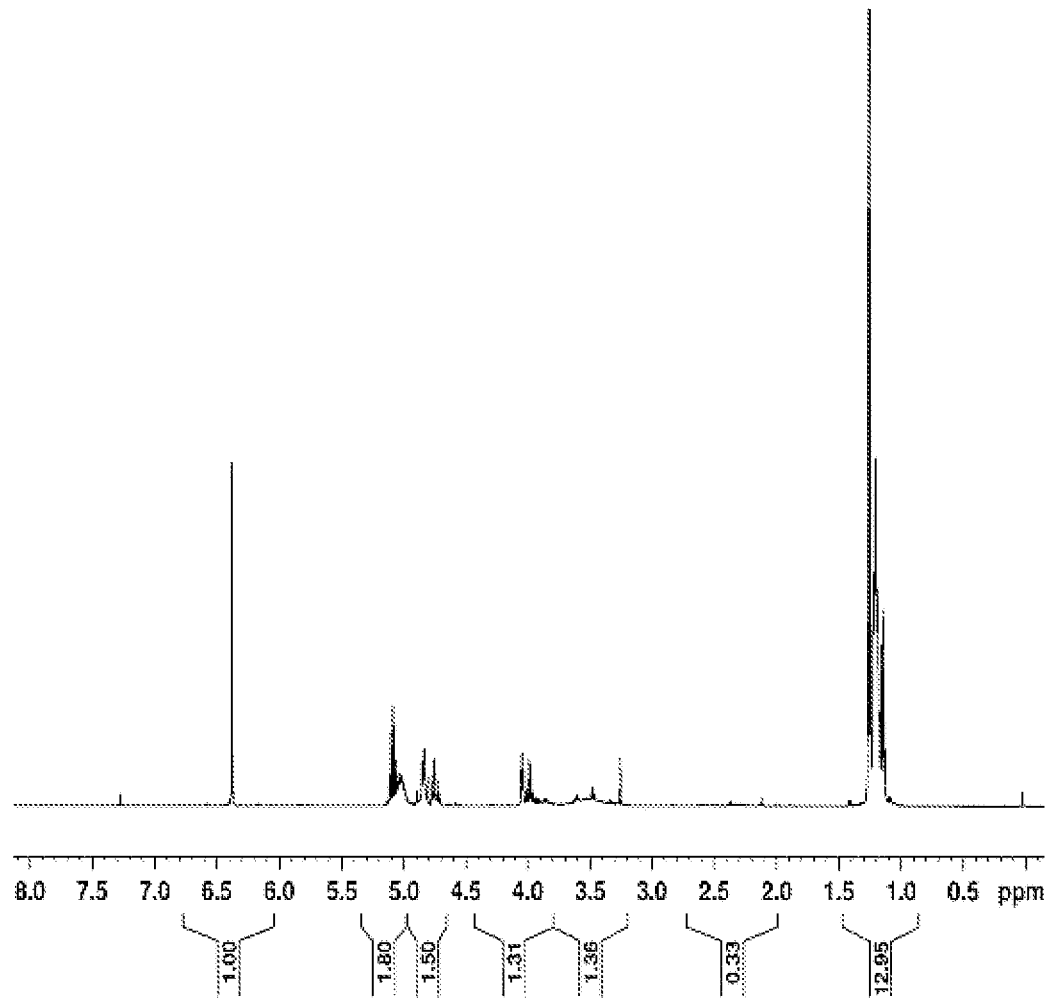
FIG. 25 depicts the $^1$H NMR spectra of crude DIPMM in CDCl$_3$ formed in accordance with the process of Example 7.
Figure 26:
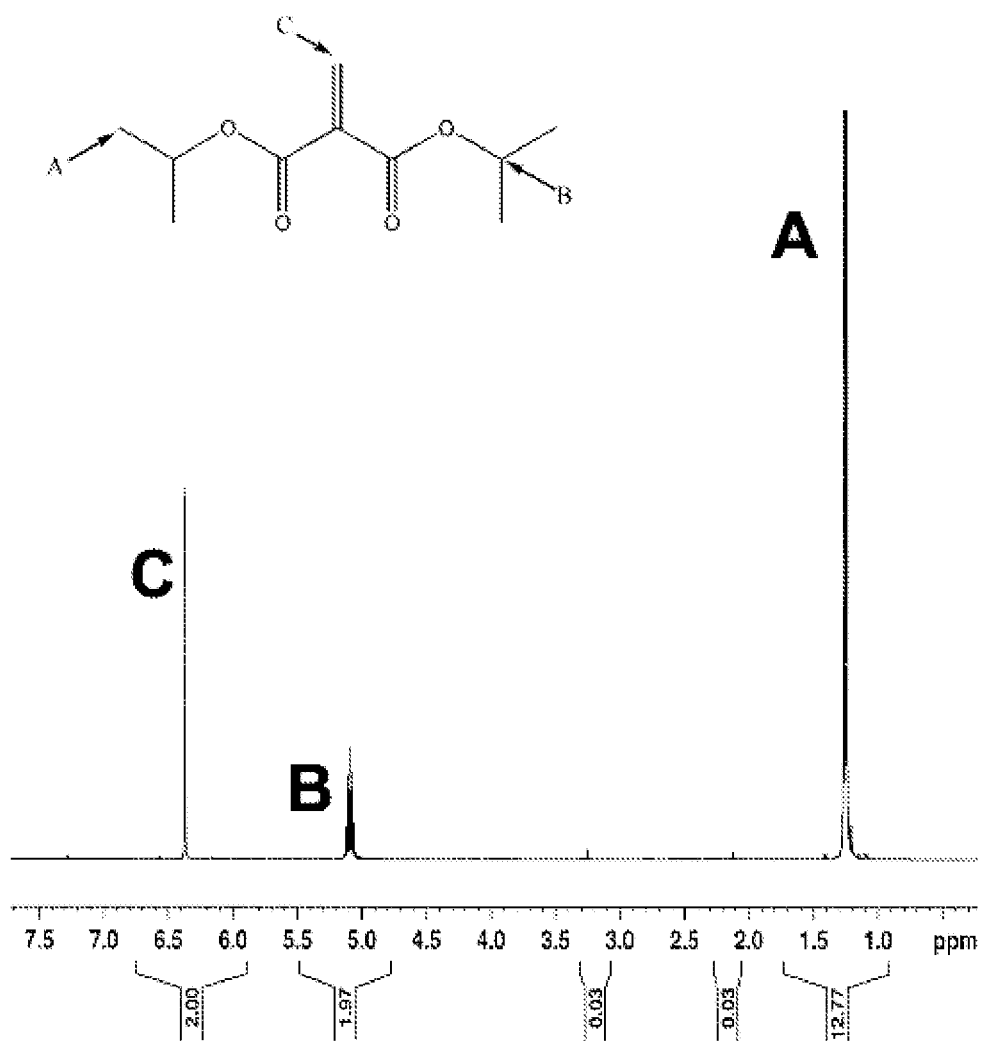
FIG. 26 depicts the $^1$H NMR spectra of 97% DIPMM in CDCl$_3$ formed in accordance with the process of Example 7.
Figure 27:
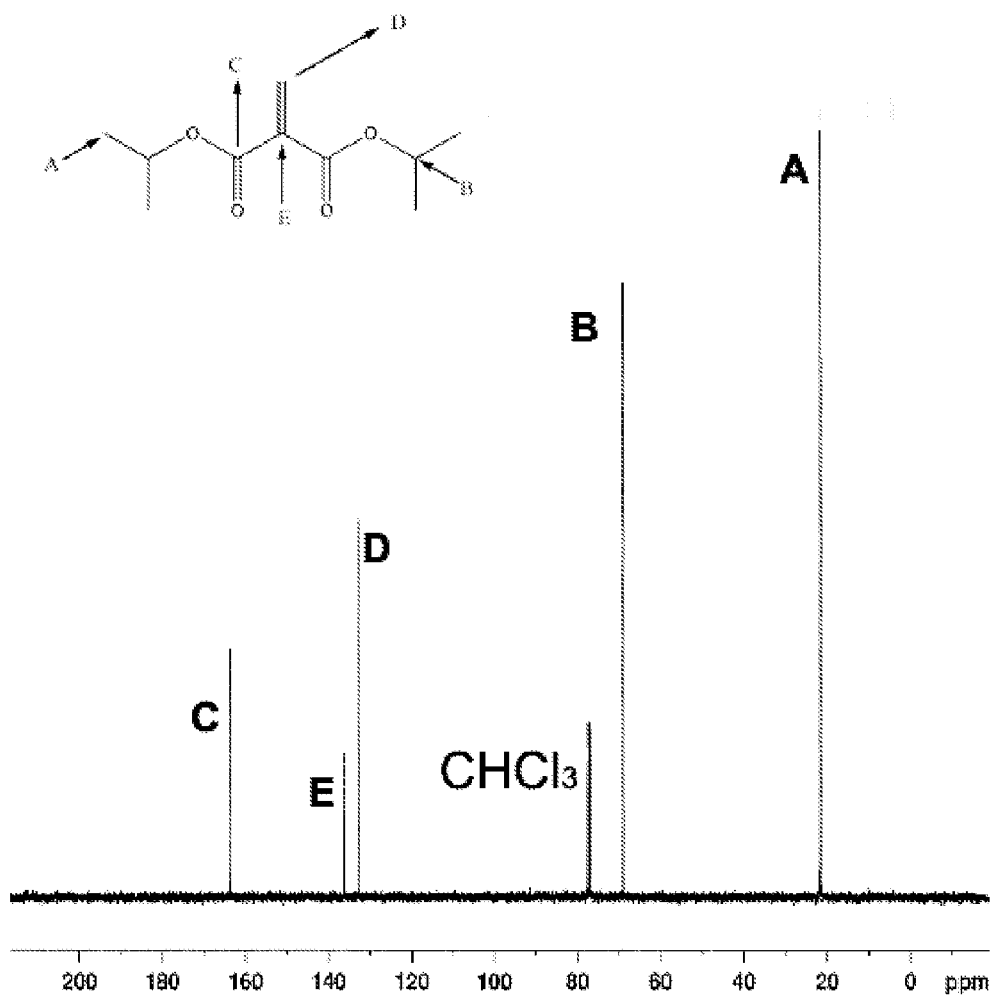
FIG. 27 depicts the $^1$H NMR spectra of 97% DIPMM in CDCl$_3$ formed in accordance with the process of Example 7.
Figure 28:
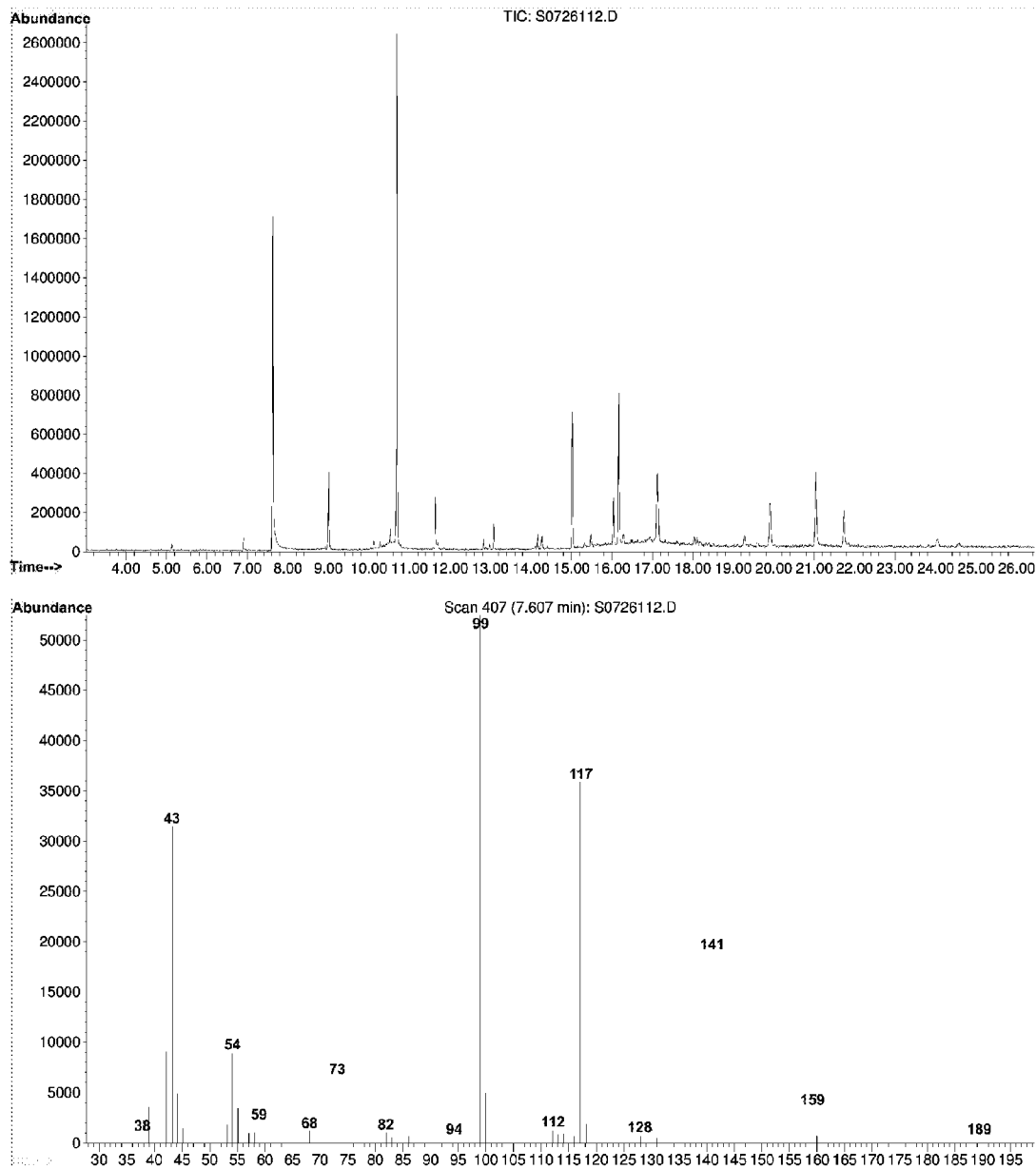
FIG. 28 depicts GC spectra for di-n-propyl methylene malonate (DNPMM) oligomeric product formed in the reaction complex as a result of the condensation reaction outlined in Example 8.
Figure 29:
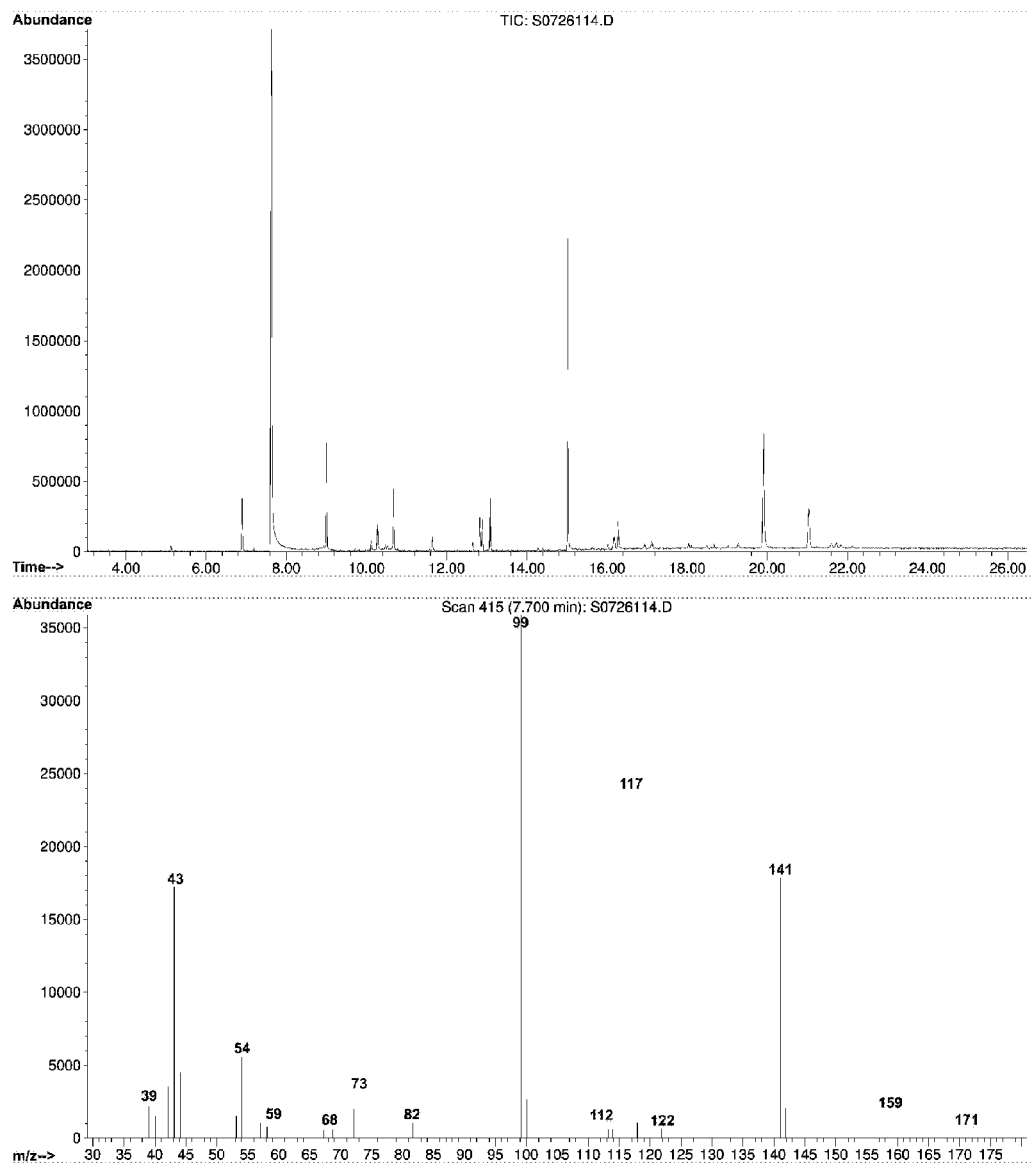
FIG. 29 depicts GC spectra for di-n-propyl methylene malonate (DNPMM) crude ("cracked") product prior to fractional distillation in accordance with the process of Example 8.
Figure 30:
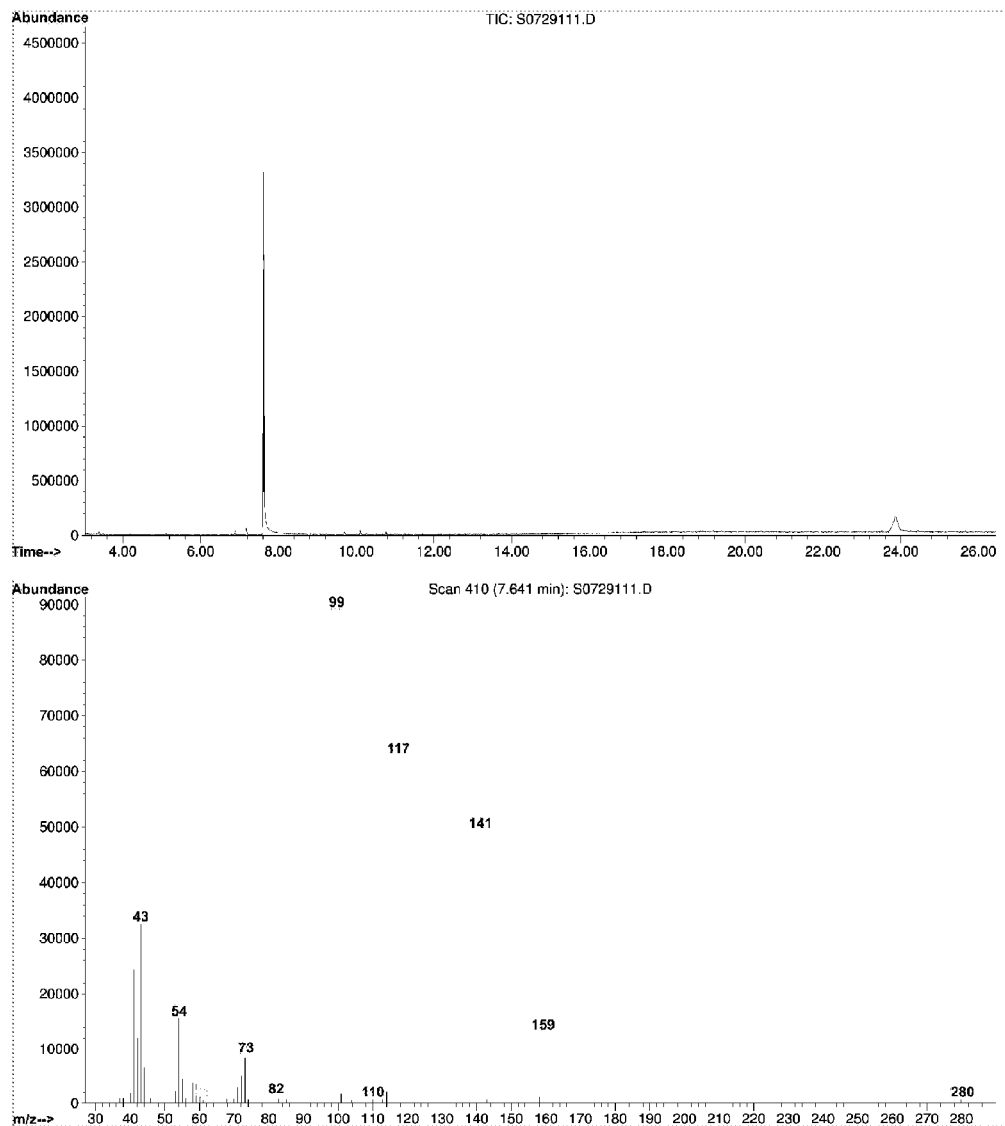
FIG. 30 depicts GC spectra for di-n-propyl methylene malonate (DNPMM) product after fractional distillation in accordance with the process of Example 8.
Figure 31:
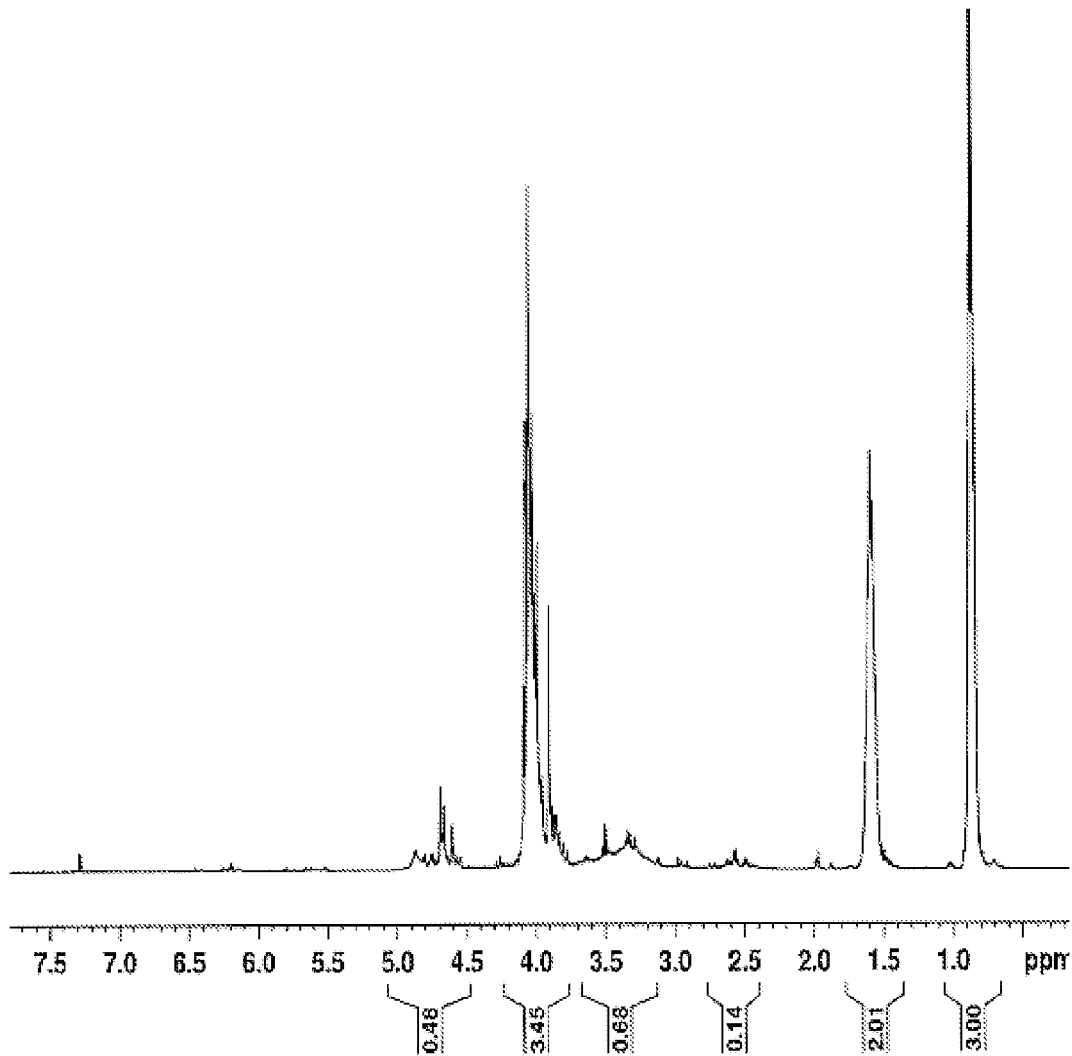
FIG. 31 depicts the $^1$H NMR spectra of DNPMM oligomeric product in CDCl$_3$ formed in accordance with the process of Example 8.
Figure 32:
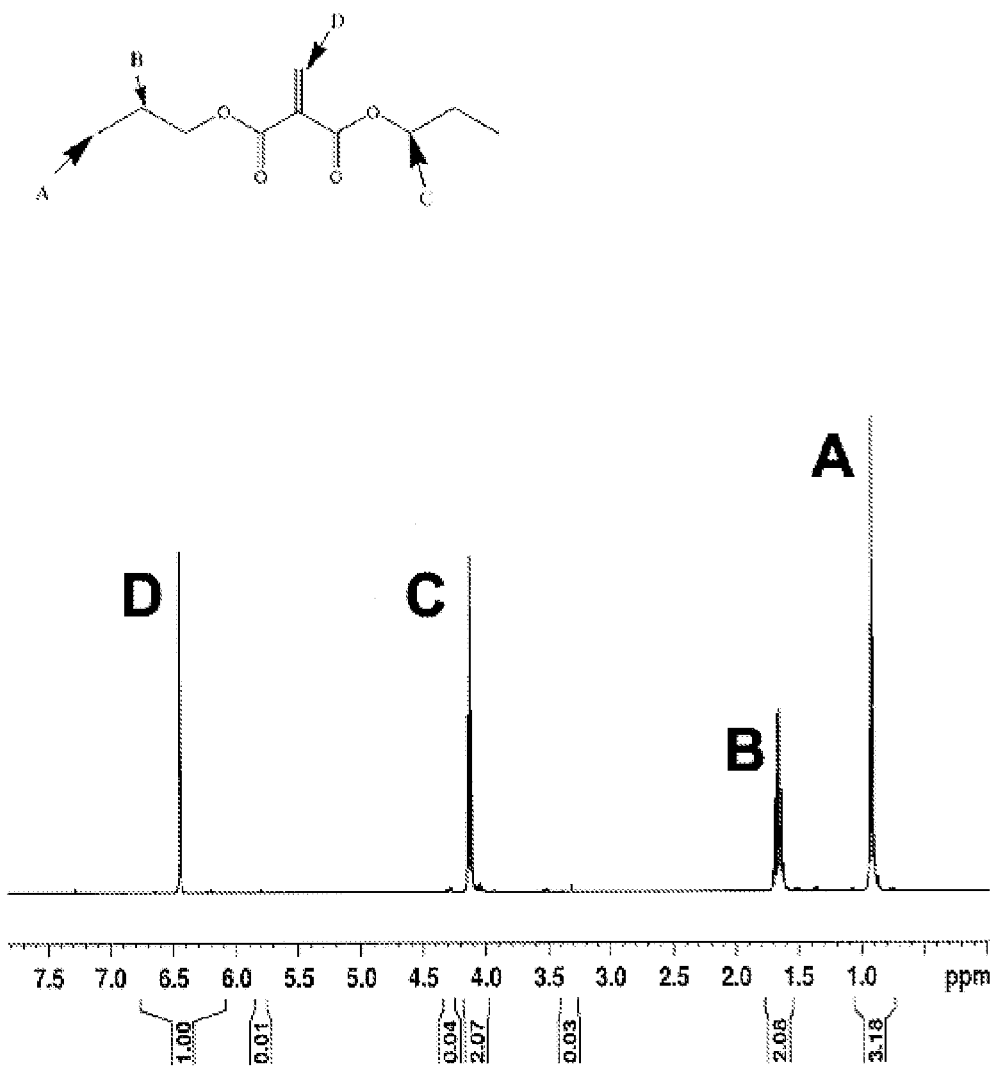
FIG. 32 depicts the $^1$H NMR spectra of DNPMM in CDCl$_3$ formed in accordance with the process of Example 8.
Figure 33:
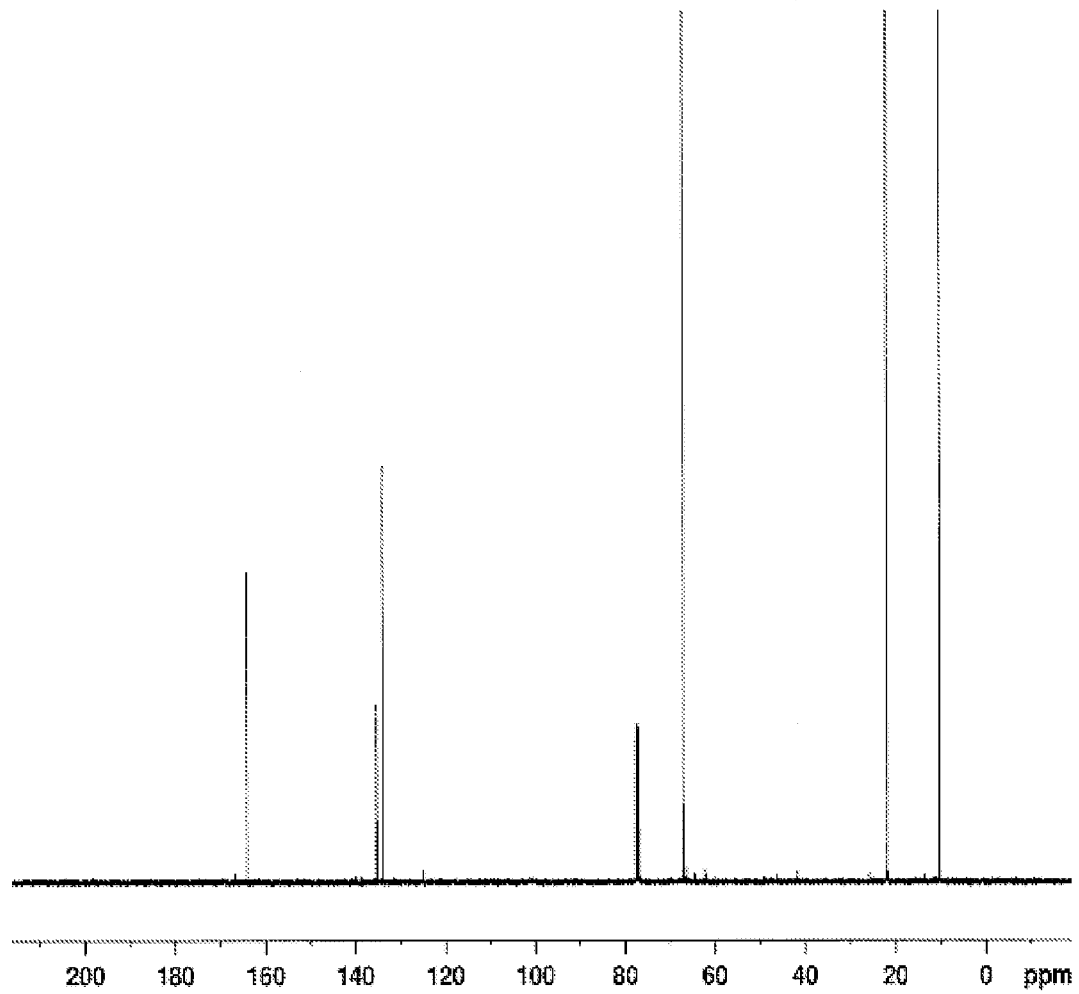
FIG. 33 depicts the $^1$H NMR spectra of 99% DNPMM in CDCl$_3$ formed in accordance with the process of Example 8.

To this flask was attached a thermocouple on one neck while a Claisen adapter, condenser, vacuum adapter and 500 mL round bottom flask was attached to the other. The 250 mL round bottom flask was then heated to 190° C. while under ~3 mmHg vacuum. After the temperature stabilized, DMMM reaction complex was then slowly added. Without being bound by any theory or mechanism, the oligomeric complex contained in the reaction complex depolymerized or "cracked" in the heated flask to form impure dimethyl methylene malonate. The resulting monomer was distilled and collected in the receiving 250 mL round bottom flask. The crude distillate was then added to a 3-neck 500 mL round bottom flask. The GC spectra shown in FIG. 15 is representative of the crude DMMM formed at this stage. Two grams of phosphorus pentoxide and one gram of hydroquinone were added and the crude monomer was fractionally distilled under reduced pressure to yield 99% pure monomer. For this process, the set temperature was 65° C., the head temperature was 32° C., and the vacuum pressure was less than 5 mm Hg. The GC spectra shown in FIG. 16 is representative of the fractionally distilled DMMM.

The spectra shown in FIGS. 14-20 are representative results of this process.

The yields expressed herein, are examples of unoptimized processes and are not representative of the potential of this process. The difference between the yields at cracking versus the gravimetric yields at the end of fractional distillation highlight the difficulty in separating the desired product from closely boiling impurities. This difficulty highlights the necessity of separating materials as soon as possible in a continuous process. As such, the inventors are not limited by the yields observed herein.

Example 8

Representative Process for Forming Di-Isopropyl Methylene Malonate Monomers

In this Example, Diisopropyl Methylene Malonate (DIPMM) was synthesized via a modified Knoevenagel Condensation reaction with 55% yield. This process, which improves significantly on prior Methylene Malonate synthesis, entails a neat Knoevenagel reaction between diisopropyl malonate, paraformaldehyde and zinc acetate dihydrate as catalyst. The first step in this reaction yields a reaction complex which may comprise an oligomeric product that may consist of alternating units of Methylene Malonate and Formaldehyde. A novel depolymerization cracking process then gives Diisopropyl Methylene Malonate.

The overall reaction scheme below outlines the synthetic route used to synthesize DIPMM. Diisopropyl malonate was reacted with paraformaldehyde in the presence of zinc acetate dihydrate as catalyst at 90° C. for 15 minutes. Without wishing to be bound by theory, the immediate product of this reaction is an oligomeric material with repeating units that may consist of alternating diisopropyl malonate and formaldehyde. This intermediate material is then thermally depolymerized to DIPMM by addition to a hot surface set between 190° to 270° C. The resulting crude DIPMM monomer is then fractionally distilled to afford pure DIPMM. The reaction scheme is shown below:

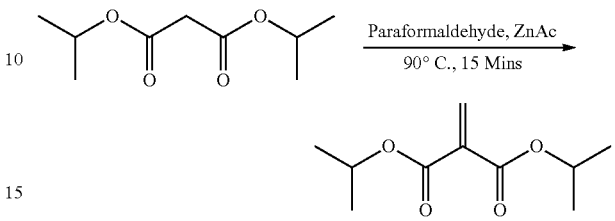

The specific process proceeded as follows:

Knoevenagel Condensation Reagents for DIPMM Synthesis:

| | Temp/ °C. | DIPM/ g | Zn/ g | Paraform/ g | Crude % yield GC-MS | % Distillation yield GC-MS |
|---|---|---|---|---|---|---|
| First Run | 105 | 100 | 0.06 | 33 | 43 | 10 |
| Second Run | 130 | 200 | 0.02 | 66 | 40 | 10 |
| Third Run | 90 | 200 | 0.23 | 64 | 72 | 15 |

A 3-neck 500 mL round bottom flask was charged with 200 g (1.06 mol) diisopropyl malonate (DIPM), 63 g (2.12) paraformaldehyde, and 0.23 g (0.0011 mol) zinc acetate dihydrate. A reflux condenser, a thermocouple and a stopper were then attached to the flask. The thermocouple was then set to 90° C. and the contents of the flask were heated. After approximately 15 minutes the reaction exothermed to 130° C. with a concurrent clarification of the mixture to opaque, viscous slurry. The reaction was run for an additional 5 minutes. The DIPMM reaction complex/oligomeric complex was then cooled to room temperature and then washed with 800 mL of cold water. The fractions were separated using a separatory funnel. The reaction complex was then placed in a 250 mL addition funnel which was attached to a 3-neck 250 mL round bottom flask, seated in a heating mantle. To this flask was attached a thermocouple on one neck and a Claisen adapter, condenser, vacuum adapter and 250 mL round bottom flask on the other. The 250 mL round bottom flask was then heated to 200° C. while under vacuum (<5 mmHg). After the temperature stabilized, the DIPMM reaction complex/oligomer was then slowly added. The oligomer depolymerized or "cracked" in the heated flask to form crude diisopropyl methylene malonate. The resulting monomer was distilled and collected in the receiving 250 mL round bottom flask. The crude distillate was then added to a 3-neck 500 mL round bottom flask. Two grams of phosphorus pentoxide and one gram of hydroquinone were added and the crude monomer was fractionally distilled under reduced pressure to yield 97% pure monomer.

Pot and Head Temperatures for Crude DIPMM Fractional Distillation:

| Set Temp./ °C. | Head Temp./ °C. | Vacuum pressure/ mmHg | % DIPMM by GC-MS |
|---|---|---|---|
| 130 | 52 | 2 | 90 |
| 133 | 55 | 4 | 94 |
| 140 | 60 | 4 | 95 |
| 140 | 60 | 4 | 97 |

Pot and head temperatures for crude DIPMM fractional distillation

The spectra shown in FIGS. 21-27 are representative results of this process.

The yields expressed herein, are examples of unoptimized processes and are not representative of the potential of this process. The difference between the yields at cracking versus the gravimetric yields at the end of fractional distillation highlight the difficulty in separating the desired product from closely boiling impurities. This difficulty highlights the necessity of separating materials as soon as possible in a continuous process. As such, the inventors are not limited by the yields observed herein.

Example 9

Representative Process for Forming Di-n-Propyl Methylene Malonate Monomers

In this Example, di-n-propyl methylene malonate (DNPMM) was synthesized via a modified Knoevenagel condensation reaction with 23% gravimetric yield. This process, which improves significantly on prior Methylene Malonate synthesis, entails a neat Knoevenagel reaction between di-n-propyl malonate, paraformaldehyde and zinc acetate dihydrate as catalyst. The first step in this reaction yields a reaction complex that may comprise an oligomeric product that may consist of alternating units of methylene malonate and formaldehyde. A novel depolymerization cracking process then gives di-n-propyl methylene malonate.

The overall reaction scheme below outlines the synthetic route used to synthesize DNPMM. Di-n-propyl malonate was reacted with paraformaldehyde in the presence of zinc acetate dihydrate as catalyst at 90° C. for 15 minutes. The immediate product of this reaction is an oligomeric material with repeat units that may consist of alternating di-n-propyl malonate and formaldehyde. This intermediate material is then thermally depolymerized to DNPMM by addition to a hot surface set between 190 and 270° C. The resulting crude DNPMM monomer is then fractionally distilled to afford pure Di-n-propyl methylene malonate. The reaction scheme is depicted as follows:

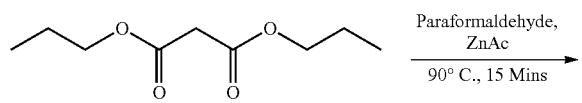

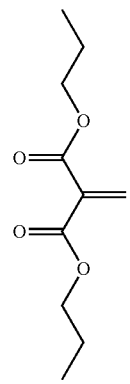

The specific process proceeded as follows:

Knoevenagel Condensation Reagents for DNPMM Synthesis:

| | Temp/ °C. | DNPM/ g | Zn/ g | Paraform/ g | Crude % yield GC-MS | % Distillation yield GC-MS |
|---|---|---|---|---|---|---|
| First Run | 90 | 175 | 2 | 56 | 18 | 4 |
| Second Run | 100 | 113 | 1.3 | 36 | 18 | 4 |

A 3-neck 500 mL round bottom flask was charged with 175 g (0.93 mol) Di-n-propyl malonate (DNPM), 56 g (1.8 mol) paraformaldehyde, and 2 g (0.0091 mol) zinc acetate dihydrate. A reflux condenser, a thermocouple and a stopper were then attached to the flask. The thermocouple was then set to 90° C. and the contents of the flask were heated. After approximately 15 minutes the reaction exothermed to 96° C. with a concurrent clarification of the mixture to an opaque, viscous slurry. The reaction was run for an additional 5 minutes. The DNPMM reaction complex/oligomer was then cooled to room temperature and then washed with 200 mL of cold water. The fractions were separated using a separatory funnel. The reaction complex/oligomeric material was then placed in a 250 mL addition funnel which was attached to a 3-neck 250 mL round bottom flask, seated in a heating mantle. To this flask was attached a thermocouple on one neck and a Claisen adapter, condenser, vacuum adapter and 250 mL round bottom flask on the other. The 250 mL round bottom flask was then heated to 200° C. while under vacuum (<5 mmHg). After the temperature stabilized, DNPMM reaction complex/oligomer was then slowly added. The oligomer depolymerized or "cracked" in the heated flask to form impure di-n-propyl methylene malonate. The resulting monomer was distilled and collected in the receiving 250 mL round bottom flask. The crude distillate was then added to a 3-neck 250 mL round bottom flask. Two grams of phosphorus pentoxide and one gram of Hydroquinone were added and the crude monomer was fractionally distilled under reduced pressure to yield 95% pure monomer.

Pot and Head Temperatures for Crude DNPMM Fractional Distillation:

| Set Temperature/ °C. | Head Temperature/ °C. | Vacuum pressure/ mmHg | % DIPMM by GC-MS |
|---|---|---|---|
| 130 | 59 | 3 | 65 |
| 144 | 80 | 4 | 88 |
| 144 | 80 | 4 | 90 |
| 160 | 85 | 5 | 95 |

The spectra shown in FIGS. 28-33 are representative results of this process.

The yields expressed herein, are examples of unoptimized processes and are not representative of the potential of this process. The difference between the yields at cracking versus the gravimetric yields at the end of fractional distillation highlight the difficulty in separating the desired product from closely boiling impurities. This difficulty highlights the necessity of separating materials as soon as possible in a continuous process. As such, the inventors are not limited by the yields observed herein.

Example 10

Additional Monomers

The following monomers were also prepared using the methods described herein by altering the starting materials.

| Starting Material | Starting Material Structure | Product Structure | Reaction Conditions | GC-MS Peaks (M/z) |
|---|---|---|---|---|
| Ethyl Allyl Malonate | [structure] | [structure] | Mol ratio of Malonate:Paraformaldehyde: Catalyst 1:2:0.001 Reaction Temperature 75-130° C. Reaction Pressure 760 mmHg Reaction Time 15-45 minutes | 41, 54, 72, 82, 99, 110, 128, 139, 156 |
| Ethyly Pyran Malonate | [structure] | [structure] | Mol ratio of Malonate:Paraformaldehyde: Catalyst 1:2:0.001 Reaction Temperature 75-130° C. Reaction Pressure 760 mmHg Reaction Time 15-45 minutes | 41, 67, 85, 98, 127, 197 |
| Tert-Butyl Ethyl Malonate | [structure] | [structure] | Mol ratio of Malonate:Paraformaldehyde: Catalyst 1:2:0.001 Reaction Temperature 75-130° C. Reaction Pressure 760 mmHg Reaction Time 15-45 minutes | 39, 57, 72, 99, 127, 145, 185 |

| Starting Material | Starting Material Structure | Product Structure | Reaction Conditions | GC-MS Peaks (M/z) |
|---|---|---|---|---|
| Ethyl cyclohexyl Malonate | | | Mol ratio of Malonate:Paraformaldehyde: Catalyst 1:2:0.001 Reaction Temperature 75-130° C. Reaction Pressure 760 mmHg Reaction Time 15-45 minutes | 41, 55, 67, 81, 96, 127, 145, 195 |
| Hexacloro Malonate | | | Mol ratio of Malonate:Paraformaldehyde: Catalyst 1:2:0.001 Reaction Temperature 75-130° C. Reaction Pressure 760 mmHg Reaction Time 15-45 minutes | 42, 69, 82, 95, 105, 117, 131, 193, 181, 193, 229, 259, 287 |
| Dibenzyl Malonate | | | Mol ratio of Malonate:Paraformaldehyde: Catalyst 1:2:0.001 Reaction Temperature 75-130° C. Reaction Pressure 760 mmHg Reaction Time 15-45 minutes | 35, 44, 65, 77, 91, 99, 107, 205, 267, 278 |

Comparative Example A

Comparative Analysis of the Inventive Process with Two Prior Art Processes

In this Example, the present invention is compared to the processes described in Eck et al. (U.S. Pat. No. 3,758,550) and Bachman et al. (U.S. Pat. No. 2,313,501) to show that the reaction complex of the present invention comprises a unique oligomeric complex as compared to the reaction processes of Eck and Bachman, i.e., Eck and Bachman do not produce the unique oligomeric complex of the invention. The present invention "cracks" its unique oligomeric complex using a rapid separation process (e.g., rapid, high-heat "flash" vaporization) to form the methylene malonate monomers of the invention.

Eck Process:

The Eck process was repeated based on Eck's own disclosure, as follows:

1. Diethyl malonate 80 g (0.5 mol), paraformaldehyde 30 g (1 mol), acetic acid 200 g, zinc acetate 6 g and acetic anhydride 51 g (0.5 mol) were stirred at 0° C. for one hour.
2. Mixture was stirred at room temperature for one hour then heated and stirred at 95° C. for 5 hours.

3. Acetic acid solvent was distilled off at 10 mm Hg vacuum and a temperature of 35° C.
4. A gel-like compound was heated at 300° C. under 10 mm Hg vacuum to get 45 g crude Diethyl methylene malonate with purity of 75% (GCMS), overall gravimetric yield is 40% (refer to diethyl malonate).

Bachman Process:
The Bachman process was repeated based on Bachman's own disclosure, as follows:
1. Paraformaldehyde 30 g (1 mol), acetic acid 200 g, copper acetate 5 g and potassium acetate 5 g were stirred at 90° C. for one hour.
2. Diethyl malonate 80 g (0.5 mol) was then added dropwise to the solution.
3. Mixture was stirred and heated at 90° C. for two hours.
4. Fractional distillations were used to obtain 33 g Diethyl methylene malonate. (40% gravimetric yield refers to diethyl malonate).

Inventive Process:
The inventive process was conducted, as follows:
1. Paraformaldehyde 168 g (5.6 mol), Diethyl Malonate 500 g (3.1 mol) and Zinc acetate 0.6 g (0.0027 mol) were mixed together at 70° C.
2. The reaction system then exotherms to 125° C. and forms the crude composition.
3. The reaction system is allowed to cool to 90° C.
4. The crude composition (90% purity of monomer according to GCMS profile) is then added slowly to a heated surface (190° C.) under vacuum (<5 mmHg) to produce crude monomer and other byproducts which were then distilled to produce diethyl methylene malonate (80% yield based on GC/MS profile and NMR) with a purity 85%.
5. The crude distillate is then fractionally distilled to give 99% pure diethyl methylene malonate with an overall gravimetric yield is ~60%

GC/MS Study of Intermediate Compositions
The composition from the inventive method has GCMS profiles that show more than 80% of diethyl methylene malonate (DEMM), with very little other impurities. Compositions from Eck and Bachman methods have GCMS profiles that show less than 20% of DEMM monomer, with much more impurities NMR Study of Intermediate Compositions
The Proton NMR ($^1$H) of the intermediate composition (after the condensation reaction) from the inventive process has shown significant differences in the chemical shifts as compared to Bachman and Eck process. The reaction product from the inventive method shows a distinct singlet with a chemical shift of 3.97 ppm, which indicates the presence of —$CH_2$ group adjacent to the oxygen atom. The peak at 3.97 ppm for product produced through the Bachman and Eck processes, though, are much smaller than the inventive process (~40% less). Moreover, the peaks in the 4.64 ppm-4.53 ppm region for Bachman and Eck products are much more complex than product from the inventive process. Also, the peaks of Bachman and Eck process are significantly broader than the peaks observed for the composition produced from the inventive process, which clearly indicates the inventive process has low molecular weight intermediate composition as compared to other two methods.

Figure 34:
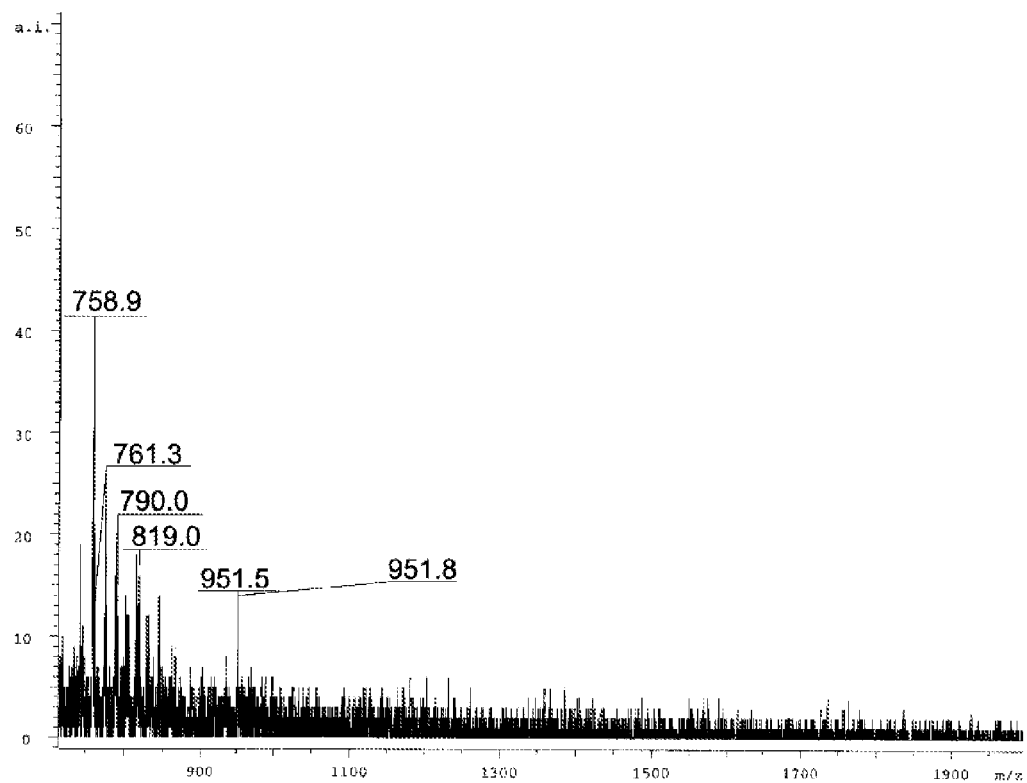
FIG. 34 depicts MALDI-TOF spectrum of the Eck process using an excess of acetic acid as solvent, according to Comparative Example A.
Figure 35:
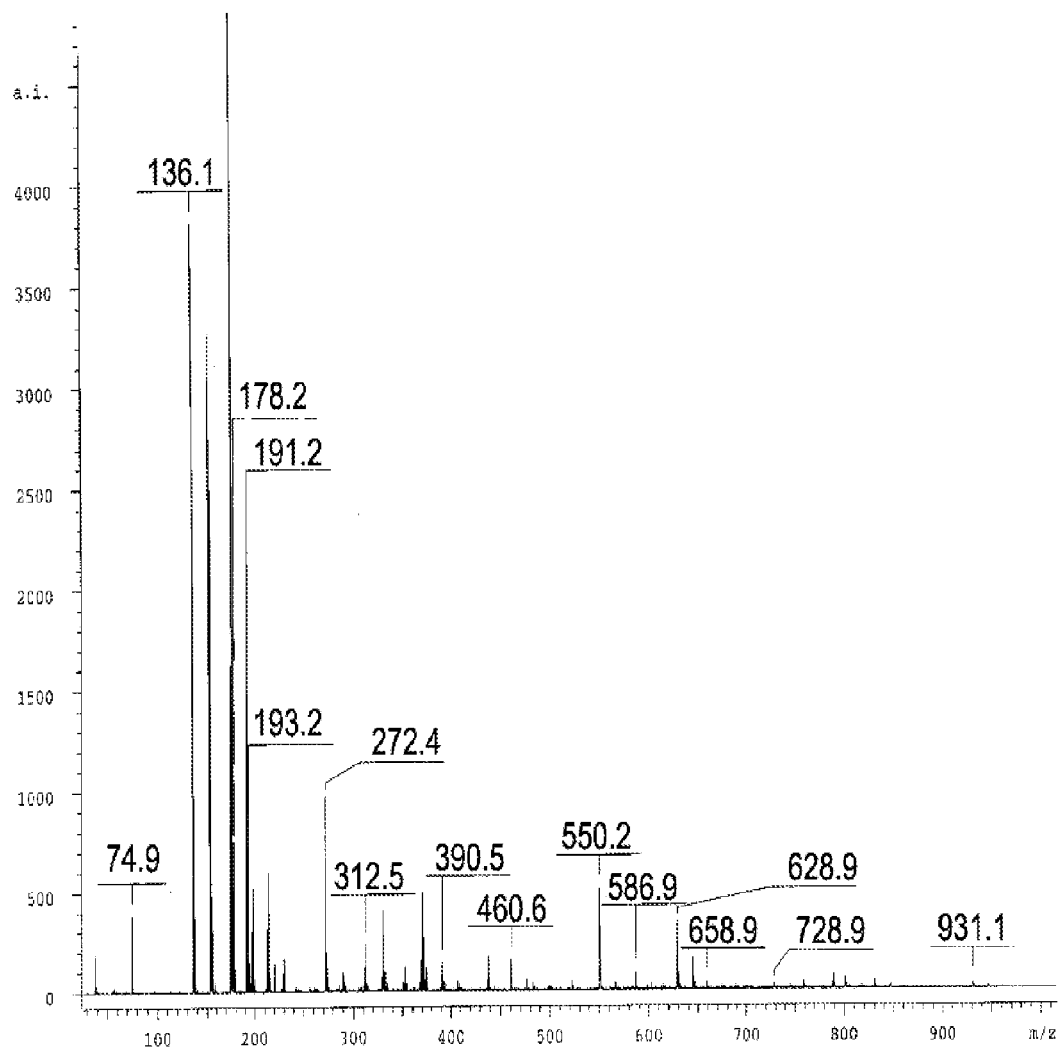
FIG. 35 depicts MALDI-TOF spectrum of the Bachman process using minimal acetic acid as solvent according to Comparative Example A.
Figure 36:
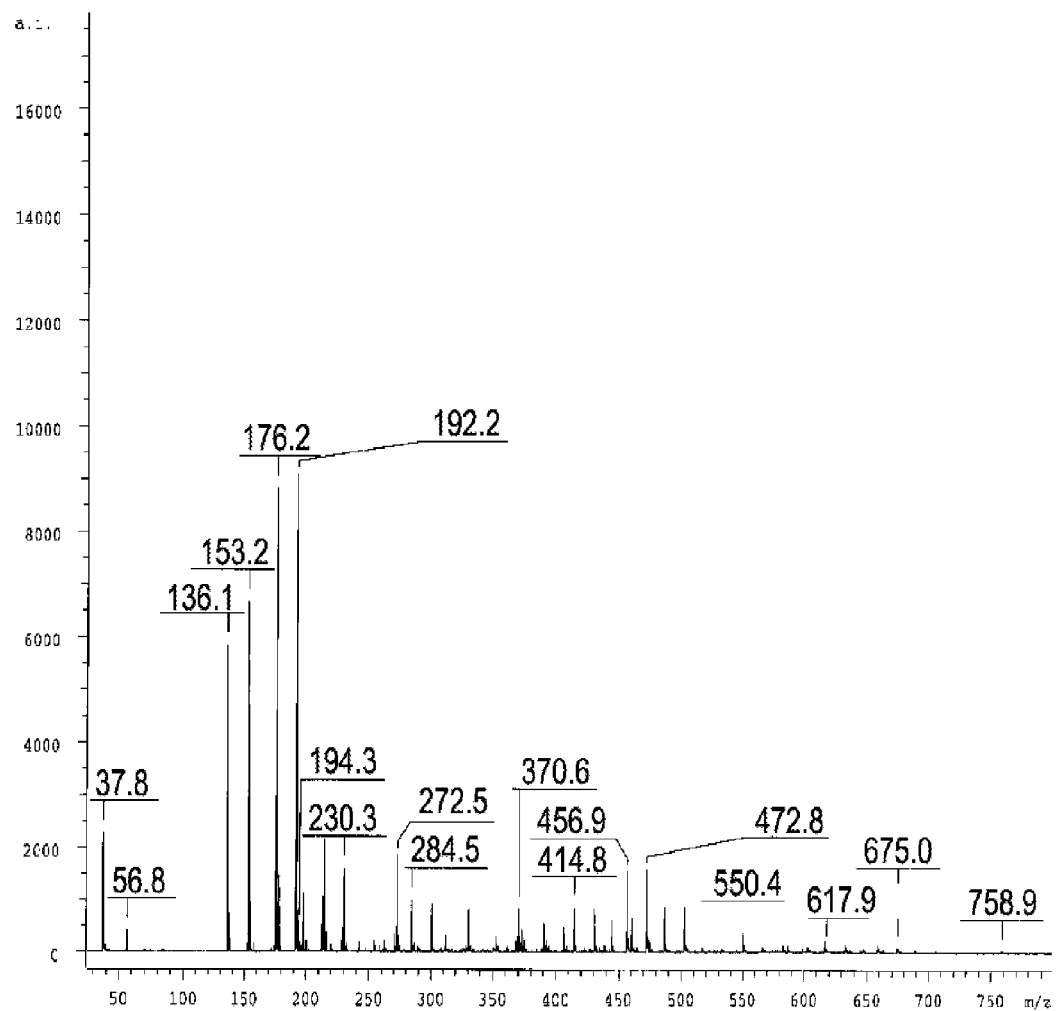
FIG. 36 depicts MALDI-TOF spectrum of the inventive process without a solvent according to Comparative Example A.

MALDI-TOF Analysis of Intermediate Compositions
Matrix Assisted Laser Desorption Time of Flight (MALDI-TOF) technique was used to qualitatively compare the product formed from the prior arts processes and our solventless condensation procedure. The products formed by the inventive method, Eck and Bachman can be seen in FIGS. 34, 35, and 35, respectively. The unique "fingerprint" of the inventive process spectrum is evidence of the unique oligomeric reaction complex formed by the invention, which is not formed by Eck and Bachman.

Comparison of Reaction Conditions
Both the Bachman and Eck processes were carried out in presence of low catalyst (0.1 mole %) as well as high catalyst (10 mole %) concentration

|  | Invention Condensation | Bachman Condensation | | ECK Condensation | |
|---|---|---|---|---|---|
|  |  | Low Cat | High Cat | Low | High |
| Catalyst Conc. (mole %) | 0.1 | 0.1 | 10 | 0.1 | 10 |
| DEM:Paraform | 1:1.8 | 1:2 | 1:2 | 1:2 | 1:2 |
| Temperature (° C.) | 70-125 (Exotherm) | 90 | 90 | 95 | 95 |
| Catalyst | Zn-Acetate | K-Acetate | K-Acetate | Zn-Acetate | Zn-Acetate |
| Co-catalyst | Not Used | Cu-Acetate | Cu-Acetate | Not Used | |
| Solvent | Not Used | Acetic Acid | Acetic Acid | Acetic Acid | Acetic Acid |
| Co-solvent | Not Used | Not Used | Not Used | Acetic Anhyd. | Acetic Anhyd. |
| Time (Hrs) | 0.5 | 1 | 1 | 5 | 5 |
| Polymerization Inhibitor | Not Used | MEHQ/HQ | MEHQ/HQ | Not Used | Not Used |

Characterization of Intermediate/Oligomeric Complex Compositions

|  | Invention | Bachman Intermediate Composition | | ECK Intermediate Composition | |
|---|---|---|---|---|---|
|  | Oligomeric Complex | Low Cat | High Cat | Low Cat | High Cat |
| GC/MS Profile DEMM (%) | >80 | <20 | <10 | <10 | <10 |
| NMR Analysis (ppm) | 4.66, 4.32-3.8 | Broad Peaks (4.7, 4.53-4.64, 4.32-4.14) | Same as low cat | Broad Peaks Similar to Bachman process | Same as low cat |
| MALDI-TOF Analysis Major peaks | 131, 153, 176, 192, 194, 370, 472, 675, 758 | 136, 178, 191, 193, 272 |  | 758, 761, 790, 819, 915 |  |
| Thermal Analysis (TGA) (° C.) | 218 | 205 |  | 228 |  |
| Consistency | Liquid not Gel | Gel after removing solvent |  | Gel after removing solvent |  |

POT "Cracked" Monomer Comparison

|  | Invention Process | Bachman Process | | ECK Process | |
|---|---|---|---|---|---|
|  |  | Low Cat | High Cat | Low Cat | High Cat |
| Pyrolysis Temp. (° C.) | 170-270 | 300 | 300 | 300 | 300 |
| Vacuum (mm) | 1 | 1 | 1 | 1 | 1 |
| GC/MS Profile purity | 80 | 76 | N/A | 75 | 51 |

-continued

| | Invention Process | Bachman Process | | ECK Process | |
|---|---|---|---|---|---|
| | | Low Cat | High Cat | Low Cat | High Cat |
| NMR Purity | 85 | | | | |
| Glass Fixture Time (Sec) | 2-3 | 90 | N/A | 120 | 180 |
| TAD (Sec) | 5-6 | 12 | N/A | 90 (gel) | 20 (gel) |
| DEMM Yield % | 70 | 35 | N/A | 40 | 43 |
| Stability at 25 (° C.) | Stable for month | 10 mins | N/A | 20 hrs | 10 hrs |

The flash vaporization of the process of the invention is not applicable to the Bachman process as the basic catalysts are carried over and instantly solidify the crude monomer.

DEMM yield calculated by (Purity %×weight of distillate) compared to initial DEM amount.

Flashed "Cracked Monomer" Comparison

| | Invention Process | Bachman Process | | ECK Process | |
|---|---|---|---|---|---|
| | | Low Cat | High Cat | Low Cat | High Cat |
| Pyrolysis Temp. (° C.) | 170-270 | 170 | 170 | 170 | 170 |
| Vacuum (mm) | 1 mm | 1 | 1 | 1 | 1 |
| GC/MS Profile purity | 80 | N/A | N/A | 28 | 51 |
| NMR Purity | 85 | | | | |
| Glass Fixture Time | 2-3 (Sec) | N/A | N/A | 15 (Mins) | 20 (Mins) |
| TAD (Sec) | 5-6 | N/A | N/A | 90 (gel) | 20 (gel) |
| DEMM Yield % | 70 | N/A | N/A | 30 | 45 |
| Stability at 25 (° C.) | Stable for up to month | N/A | N/A | 2 days | 2 days |

Final Fractional Distillation

| | Invention Process | Bachman Process | Eck Process |
|---|---|---|---|
| No. of Distillation to obtain 99% purity | 1 | 4 | N/A |
| Pot Temp. (° C.) | 80-90 | 80-90 | Not Used |
| Head Temp. (° C.) | 60 | 60 | Not Used |
| Vacuum | 1 mm | 1 mm | Not Used |
| Stabilizer during distn. | $P_2O_5$ + MEHQ/HQ | Not Used | Not Used |
| | | | Not Used |
| GC/MS Profile Purity | 99% | 99% | |
| | | | Not Used |
| NMR Purity | 99% | 99% | |
| | | | Not Used |
| TAD (Sec) | 1 | 3 | |
| | | | Not Used |
| Glass Fixing Time (Sec) | 1 | 10 | Not Used |
| Self life without stabilizer | Stable up to 6. months | Solidified within 24 hrs | Not Used |
| Stabilizer Package | Methanesulfonic acid + MEHQ/HQ | Not Used | Not used |

Overall Process Yield:

| | Invention Process | Bachman Process | Eck Process |
|---|---|---|---|
| Yield (%) | 65-70 | 40 | 43% |

DEMM yield calculated by (Purity %×weight of distillate), refer to DEM.

Note: Eck did not report the fractional distillation of DEMM/purity of DEMM/performance of DEMM

REFERENCES CITES

The following documents may be cited or referenced herein, each of which are incorporated by reference herein and may be employed in the practice of the invention.

Patent Literature (1) U.S. Pat. No. 2,313,501;
(2) U.S. Pat. No. 2,330,033;
(3) U.S. Pat. No. 3,197,318;
(4) U.S. Pat. No. 3,221,745;
(5) U.S. Pat. No. 3,523,097;
(6) U.S. Pat. No. 3,557,185;
(7) U.S. Pat. No. 3,758,550;
(8) U.S. Pat. No. 3,975,422;
(9) U.S. Pat. No. 4,049,698;
(10) U.S. Pat. No. 4,056,543;
(11) U.S. Pat. No. 4,160,864;
(12) U.S. Pat. No. 4,931,584;
(13) U.S. Pat. No. 5,142,098;
(14) U.S. Pat. No. 5,550,172;
(15) U.S. Pat. No. 6,106,807;
(16) U.S. Pat. No. 6,211,273;
(17) U.S. Pat. No. 6,245,933;
(18) U.S. Pat. No. 6,420,468;
(19) U.S. Pat. No. 6,440,461;
(20) U.S. Pat. No. 6,512,023;
(21) U.S. Pat. No. 6,610,078;
(22) U.S. Pat. No. 6,699,928;
(23) U.S. Pat. No. 6,750,298; and
(24) 2004/0076601.

Non-Patent Literature

M. Ware et al.: "DBU: An Efficient Catalyst for Knoeveganel Condensation under Solvent-free Condition," Bulletin of the Catalysis Society of India, (2007), Vol. 6, pp. 104-106

V. G. Nenajdenko et al.: "Reaction of 2-Methylene-1,3-Dicarbonyl Compounds Containing a $CF_3$-Group with 1,3-Dienes," Tetrahedron, (2000), Vol. 56, pp. 6549-6556

J. S. Yadav et al.,: "Phosphane-Catalyzed Knoevenagel Condensation: a Facile Synthesis of α-Cyanoacrylates and α-Cyanoacrylonitriles," Eur. J. Org. Chem. (2004), pp. 546-551

B. C. Ranu et al.: "Ionic Liquid as Catalyst and Reaction Medium—a Simple, Efficient and Green Procedure for Knoevenagel Condensation of Aliphatic and Aromatic Carbonyl Compounds Using a Task-Specific Basic Ionic Liquid," Euro. J. Org. Chem., (2006), pp. 3767-3770

H. A. Oskooie et al.: "On Water: an Efficient Knoevenagel Condensation using 12-Tungstophosphoric Acid as a Reusable Green Catalyst," Synthetic Communications, (2006), Vol. 36, pp. 2819-2823

H. Jiang et al.: "Inorganic Zinc Salts Catalyzed Knoevenagel Condensation at Room Temperature without Solvent," Preparative Biochemistry & Biotechnology, (2009), Vol. 39, pp. 194-200

B. M. Reddy et al.: "An Easy-to-use Heterogeneous Promoted Zirconia Catalyst for Knoevenagel Condensation in liquid Phase under Solvent-Free Conditions," Journal of Molecular Catalysis A: Chemical, (2006), Vol. 258, pp. 302-307

D. H. Jung et al.: "New and General Methods for the Synthesis of Arylmethylene Bis(3-Hydroxy-2-Cyclohexene-1-Ones) and Xanthenediones by EDDA and In(OTf)$_3$-Catalyzed One-Pot Domino Knoevenagel/Michael or Koevenagel/Michael/Cyclodehydration Reactions," Bull. Korean Chem. Soc. (2009) Vol. 30, No. 9, pp. 1989-1995

P. Klemarczyk: "Adhesion Studies of Mixtures of Ethyl Cyanoacrylate with a Difunctional Cyanoacrylate Monomer and with other Electron-deficient Olefins," J. Adhesion, (1999), Vol. 69, pp. 293-306

P. Klemarwczyk: "A General Synthesis of 1,1 Disubstituted Electron Deficient Olefins and their Polymer Properties," Polymer, (1998), Vol. 39, No. 1, pp. 173-181

C. Gill et al.: "Knoevenagel Condensation in Neutral Media: A simple and efficient protocol for the Synthesis of Electrophillic alkenes Catalyzed by Anhydrous Ferric Sulphate with Remarkable Reusability," Department of Chemistry, Dr. Babasaheb Ambedkar Marathwada University, Aurangabad 431 004 (MS), India, (n/a), pp. n/a P. Ballesteros et al.: "DI-tert-Butyl Methylenemalonate [Propanedioic Acid, Methylene-, bis(1,1-dimethylethyl)ester]," Organic Syntheses. Coll. (1990), Vol. 7, p. 142; (1986) Vol. 64, p. 63

A. M. Vetrova et al.: "Improvement of the Thermal Stability of Cyanoacrylate Adhesives," Polymer Science, Series D, (2009), Vol. 2, No. 1, pp. 27-30

A. C. Cope: "Condensation Reactions. I. The Condensation of Ketones with Cyanoacetic Esters and the Mechanism of the Knoevenagel Reaction," Condensation of Ketones with Cyanoacetic Esters, (1937), Vol. 59, pp. 2327-2330

G. Lai et al.: "Ionic Liquid Functionalized Silica Gel: Novel Catalyst and Fixed Solvent," Tetrahedron Letters (2006), Vol. 47, pp. 6951-6953

J. R. Harjani et al.: "Lewis Acidic Ionic Liquids for the Synthesis of Electrophilic Alkenes via the Knoevenagel Condensation," Tetrahedron Letters, (2002), Vol. 43, pp. 1127-1130

P. Ballesteros et al.: "Synthesis of DI-tert-Butyl Methylenemalonate, a Sterically Hindered 1,1-Dicarbonyl Alkene," J. Org. Chem., (1983), Vol. 48, pp. 3603-3605

T. Doi et al.: "Synthesis of Dimethyl gloiosiphne A by Way of Palladium-Catalyzed Domino Cyclization," J. Org. Chem., (2007), Vol. 72, pp. 3667-3671

What is claimed is:

1. A method of making a methylene malonate monomer comprising:
   a) reacting a malonic acid ester with a source of formaldehyde; optionally in the presence of an acidic or basic catalyst; and in the absence of solvent, to form a reaction complex;
   b) contacting the reaction complex or a portion thereof with an energy transfer means at a temperature of about 130° to about 300° to produce a vapor phase comprising methylene malonate monomer wherein the reaction complex or the portion thereof is substantially vaporized in less than 1 minute; and
   c) isolating the methylene malonate monomer from the vapor phase.

2. The method according to claim 1, wherein the reaction complex or the portion thereof is substantially vaporized in less than 10 seconds.

3. The method according to claim 1, wherein the reaction complex of the portion thereof is substantially vaporized prior to the formation of latent acid forming impurities or irreversible complex impurities.

4. The method according to claim 1, comprising repeating steps (b) and (c) on additional portions of the reaction complex, wherein each portion of the reaction complex is substantially vaporized in step (b) prior to the contacting of another portion of the reaction complex with the energy transfer means.

5. The method according to claim 1, wherein the reaction complex is vaporized continuously upon formation in step (a).

6. The method according to claim 1, wherein the energy transfer means is at least one member of the group consisting of: a heat exchanger, a laser, a source of radiation and microwave radiation.

7. The method of according to claim 1 wherein the energy transfer means comprises a heated inert gas, one or more metal articles, one or more glass articles, one or more porcelain articles, sand, silica, silicone oil, mineral oil, a petroleum-based heat transfer oil, a synthetic chemical-based heat transfer oil, or a pre-formed portion of the reaction complex.

8. The method according to claim 1, wherein in (a) reacting the malonic acid ester with the source of formaldehyde is performed at about 60° C. to about 130° C.

9. The method according to claim 1, wherein in (c) isolating the methylene malonate monomer is achieved by a separation technique selected from condensation, simple distillation, fractional distillation, flash distillation, steam distillation, vacuum distillation, short path distillation, thin-film distillation, reactive distillation, pervaporation, extractive evaporation, flash evaporation, rotary evaporation, gas chromatography or liquid chromatography.

10. The method according to 1 further comprising the step of (d) redistilling the methylene malonate monomer under reduced pressure within about 60 minutes of isolation.

11. The method according to 1 further comprising the step of inactivating the catalyst prior to producing the vapor phase.

12. The method according to 1 further comprising the step of minimizing recovery of volatile latent acid forming impurities.

13. The method according to claim 1 wherein the reacting step (a) is performed in the presence of a basic catalyst selected from potassium acetate, sodium acetate, zinc acetate, zinc diacetate dehydrate, aluminum acetate, calcium acetate, magnesium acetate, magnesium oxide, copper acetate, lithium acetate, aluminum oxide, zinc oxide or any combination thereof.

14. The method according to claim 1 wherein the malonic acid ester has the formula:

$$R-O-C(O)-CH2-C(O)-O-R'$$

wherein R and R' are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl-($C_1$-$C_{15}$ alkyl), heteroaryl or heteroaryl-($C_1$-$C_{15}$ alkyl), or alkoxy-($C_1$-$C_{15}$ alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester; or wherein R and R' are taken together with the atoms to which they are bound to form a 5-7 membered heterocyclic ring which may be optionally substituted by $C_1$-$C_{15}$ alkyl, halo-$C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

15. The method according to claim 1 wherein the reaction complex comprises one or more oligomeric complexes capable of forming the methylene malonate monomer as a result of conducting step (b).

16. The method according to claim 15 wherein the one or more oligomeric complexes independently comprise between 2 and 12 units of methylene malonate monomer.

17. The method according to claim 15 wherein the oligomeric complex comprises at least one of the following physiochemical properties:
  (b) a MALDI-TOF analysis spectrum comprising peaks at: 131, 153, 176, 192, 194, 470, 472, 675, and 758; or
  (c) a proton NMR spectrum in $CDCl_3$ at 400 MHz comprising the following peaks: a singlet at 4.66 ppm and narrow peaks located between 4.32-3.8 ppm.

18. The method according to claim 15 wherein the oligomeric complex results in a weight loss of less than 20% below 218° C. as measured by thermogravimetric analysis.

* * * * *